(12) United States Patent
Heinelt et al.

(10) Patent No.: US 8,198,272 B2
(45) Date of Patent: Jun. 12, 2012

(54) TRIAZOLIUM SALTS AS PAR1 INHIBITORS, PRODUCTION THEREOF, AND USE AS MEDICAMENTS

(75) Inventors: Uwe Heinelt, Frankfurt am Main (DE); Volkmar Wehner, Frankfurt am Main (DE); Matthias Herrmann, Frankfurt am Main (DE); Karl Schoenafinger, Alzenau (DE); Henning Steinhagen, Sulzbach (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/851,219

(22) Filed: Aug. 5, 2010

(65) Prior Publication Data

US 2011/0034452 A1   Feb. 10, 2011

Related U.S. Application Data

(63) Continuation of application No. PCT/EP2009/000407, filed on Jan. 23, 2009.

(30) Foreign Application Priority Data

Feb. 5, 2008 (EP) .................................. 08290114

(51) Int. Cl.
*C07D 487/04* (2006.01)
*C07D 413/10* (2006.01)
*A61K 31/5025* (2006.01)
*A61K 31/5355* (2006.01)
*A61P 7/00* (2006.01)
*A61P 9/10* (2006.01)
*A61P 29/00* (2006.01)
*A61P 37/08* (2006.01)
*A61P 3/14* (2006.01)

(52) U.S. Cl. ..................... 514/233.2; 514/248; 544/118; 544/236

(58) Field of Classification Search .................. 544/236, 544/118; 514/248, 233.2
See application file for complete search history.

(56) References Cited

U.S. PATENT DOCUMENTS

| | | | |
|---|---|---|---|
| 4,578,464 A | 3/1986 | Cregge et al. | |
| 6,063,847 A | 5/2000 | Chackalamannil et al. | |
| 7,375,236 B2 | 5/2008 | Shimomura et al. | |
| 2004/0152736 A1 | 8/2004 | Chackalamannil et al. | |
| 2004/0242659 A1 | 12/2004 | Tasaka et al. | |
| 2005/0197370 A1 | 9/2005 | Bossenmaier et al. | |
| 2011/0034451 A1 | 2/2011 | Heinelt et al. | |
| 2011/0034456 A1 | 2/2011 | Heinelt et al. | |
| 2011/0034461 A1 | 2/2011 | Heinelt et al. | |
| 2011/0034467 A1 | 2/2011 | Rohrig et al. | |
| 2011/0034468 A1* | 2/2011 | Huang et al. | 514/248 |
| 2011/0034506 A1* | 2/2011 | Sun | 514/303 |

FOREIGN PATENT DOCUMENTS

| | | |
|---|---|---|
| EP | 1391451 | 2/2004 |
| EP | 1391452 | 2/2004 |
| EP | 1394152 | 3/2004 |
| EP | 1813282 | 8/2007 |
| WO | WO 03/089428 | 10/2003 |
| WO | WO 2004/078721 | 9/2004 |
| WO | WO 2007/075567 | 7/2007 |

OTHER PUBLICATIONS

International Search Report for WO2009/097971 dated Aug. 13, 2009.
Notice of Allowance for U.S. Appl. No. 12/851,189 dated Aug. 12, 2011.
European Heart Journal, vol. 28, Suppl. 1, (2007), pp. 3-250.
Ahn, et al., Binding of a Thrombin Receptor Tethered Ligand Analogue to Human Platelet Thrombin Receptor, Molecular Pharmacology, vol. 51, pp. 350-356, (1997).
Brass, S., et al., Platelets and Proteases, Nature, vol. 413, (2001), pp. 26-27.
Chackalamannil, et al., Thrombin Receptor (PAR-1) Antagonists as Novel Antithrombotic Agents, Expert Opin. Ther. Patents, (2006), vol. 16, No. 4, pp. 493-505.
Cristau, et al., Les Tribromures De Phosphoniums. Agents de Bromation de Substrats Organiques, Phosphorus and Sulfur. (1985), vol. 25, pp. 357-367.
Hollenberg, et al., International Union of Pharmacology, XXVIII, Proteinase-Activated Receptors, Pharmacological Reviews, vol. 54, No. 2, pp. 203-217, (2002). Horie, T., et al., Studies on Pyridazine Derivatives, V. 1) Syntheses of 5-Substituted Derivatives of 3-Amino-6-Alkoxypyridazine 2-Oxide, Chem. Pharm. Bull., vol. 11, No. 9, pp. 1157-1167, (1963).

(Continued)

*Primary Examiner* — James O Wilson
*Assistant Examiner* — Cecilia M Jaisle
(74) *Attorney, Agent, or Firm* — Kelly L. Bender

(57) ABSTRACT

The invention relates to novel compounds of formula I

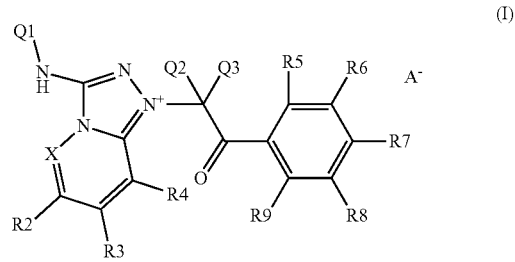

where X, A⁻, Q1, Q2, Q3, R2, R3, R4, R5, R6, R7, R8 and R9 are each as defined below. The compounds of formula I have antithrombotic activity and inhibit especially protease-activated receptor 1 (PAR1). The invention further relates to a process for preparing the compound of formula I and to the use thereof as a medicament.

6 Claims, No Drawings

OTHER PUBLICATIONS

Suzuki, K., et al., Reductive Pinacol-Type Rearrangement of Chiral A-Mesyloxy Ketones Promoted by Organoaluminum Compounds, Tetrahedron Letter, vol. 25, No. 34, pp. 3715-3718, (1984).

Welch, J. T., et al., The synthesis and Biological Activity of Pentafluorosulfanyl Analogs of Fluoxetine, Fenfluramine, and Norfenfluramine, Bioorganic and Medicinal Chemistry, vol. 15, (2007), pp. 6659-6666.

Abstract Selected for ESC 2007 Sep. 1-5, 2007, Vienna—Austria, European Heart Journal, (2007), vol. 28 (Abstract Supplement), iii-vi.

* cited by examiner

TRIAZOLIUM SALTS AS PAR1 INHIBITORS, PRODUCTION THEREOF, AND USE AS MEDICAMENTS

FIELD OF THE INVENTION

The invention relates to novel compounds of the formula I

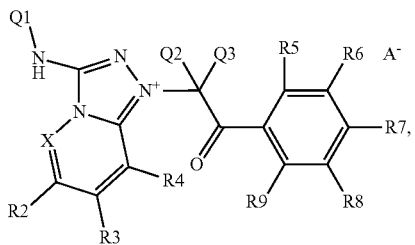

where X, A⁻, Q1, Q2, Q3, R2, R3, R4, R5, R6, R7, R8 and R9 are each as defined below. The compounds of the formula I have antithrombotic activity and inhibit especially protease-activated receptor 1 (PAR1). The invention further relates to a process for preparing the compound of the formula I and to the use thereof as a medicament.

BACKGROUND OF THE INVENTION

Protease-activated receptor 1 (PAR1) is a thrombin receptor which belongs to the class of G protein-coupled receptors (GPCR). The gene for PAR1 is located on chromosome 5q13, consists of two exons and covers a region of about 27 kb.

PAR1 is expressed inter alia in endothelial cells, smooth muscle cells, fibroblasts, neurons and human blood platelets. On blood platelets, PAR1 is an important receptor of signal transmission and is involved in initiating the aggregation of blood platelets.

Activation of the PARs takes place by proteolytic elimination of part of the N terminus of the PARs, thus exposing a new N-terminal sequence which then activates the receptor (Pharmacol Rev 54:203-217, 2002).

The coagulation of blood is a process for controlling blood flow which is essential for the survival of mammals. The process of coagulation and the subsequent breakup of the clot after wound healing has taken place starts after damage to a vessel and can be divided into four phases:

1. The phase of vascular constriction: the blood loss into the damaged area is reduced thereby.
2. The next phase is that of platelet adhesion to the exposed collagen in the subendothelium. This primary adhesion to the matrix activates the platelets, which then secrete various activators which lead to enhancement of the activation. These activators additionally stimulate further recruitment of new platelets to the site of vessel damage and promote platelet aggregation. The platelets aggregate at the site of vessel wall damage and form a still loose platelet plug. Activation of platelets further leads to presentation of phosphatidylserine and phosphatidylinositol along the cell membrane surfaces. Exposure of these phospholipids is essential for binding and activating the multienzyme complexes of the coagulation cascade.
3. The initially still loose platelet aggregate is crosslinked by fibrin. If the thrombus comprises only platelets and fibrin, it is a white thrombus. If red blood corpuscles are additionally present, it is a red thrombus.
4. After wound healing, the thrombus is broken up by the action of the protein plasmin.

Two alternative pathways lead to the formation of a fibrin clot, the intrinsic and the extrinsic pathway. These pathways are initiated by different mechanisms, but in a later phase they converge to a common pathway of the coagulation cascade. Formation of a red thrombus or a clot on the basis of a vessel wall abnormality without wound is the result of the intrinsic pathway. Fibrin clot formation as response to tissue damage or injury is the result of the extrinsic pathway. Both pathways include a relatively large number of proteins which are known as coagulation factors.

The intrinsic pathway requires coagulation factors VIII, IX, X, XI and XII and prekallikrein, high molecular weight kininogen, calcium ions and phospholipids from platelets. Each of these proteins leads to activation of factor X.

The intrinsic pathway is initiated when prekallikrein, high molecular weight kininogen, factor XI and XII bind to a negatively charged surface. This moment is referred to as the contact phase. Exposure to a vessel wall collagen is the primary stimulus of the contact phase. The result of the contact phase processes is conversion of prekallekrein into kallekrein, which in turn activates factor XII. Factor XIIa hydrolyzes further prekallekrein to kallekrein, so that the result is activation. As the activation of factor XII increases there is activation of factor XI which leads to release of bradykinin, a vasodilator. The initial phase of vasoconstriction is terminated thereby. Bradykinin is produced from the high molecular weight kininogen. In the presence of Ca²⁺ ions, factor XIa activates factor IX. Factor IX is a proenzyme which contains vitamin K-dependent, c-carboxyglutamate (GLA) residues. The serine protease activity becomes evident after Ca²⁺ ions have bound to these GLA residues. Several of the serine proteases in the blood coagulation cascade (factors II, VII, IX and X) contain such vitamin K-dependent GLA residues. Factor IXa cleaves factor X and leads to activation to factor Xa. The precondition for the formation of factor IXa is the formation of a protease complex of Ca²⁺ ions and factors VIIIa, IXa and X on the surface of activated platelets. One of the reactions of activated platelets is the presentation of phosphatidylserine and phosphatidylinositol along the surfaces. Formation of the protease complex is made possible by exposure of these phospholipids. In this process, factor VIII acts as a receptor for factors IXa and X. Factor VIII therefore represents a cofactor in the coagulation cascade. Activation of factor VIII with formation of factor VIIIa, the actual receptor, requires only a minimal amount of thrombin. As the concentration of thrombin increases, factor VIIIa is finally cleaved further, and inactivated, by thrombin. This dual activity of thrombin in relation to factor VIII leads to the protease complex formation being self-limiting and thus the blood coagulation being localized.

PAR1 and PAR4 play a central role in the activation of human blood platelets by thrombin; activation of these receptors leads to morphological changes in blood platelets, release of ADP and aggregation of the blood platelets (Nature 413: 26-27, 2001).

PAR1 inhibitors are described for example in the European patent applications EP1391451 or EP1391452, the U.S. Pat. No. 6,063,847 and US 2004/152736, and the international application WO 03/089428.

DESCRIPTION OF THE INVENTION

The compounds of the formula I show a high specific inhibition of protease-activated receptor 1 and are notable, compared to compounds from EP1391451, for improved water solubility.

The compounds of the formula I are therefore suitable for prophylactic and therapeutic use in humans suffering from disorders associated with thromboses, embolisms, hypercoagulability or fibrotic alterations. Examples of such disorders are thrombosis, deep vein thrombosis, pulmonary embolisms, cerebral infarction, myocardial infarction, high blood pressure, inflammatory disorders, rheumatism, asthma, glomerulonephritis or osteoporosis. The compounds of the formula I can be employed for secondary prevention and are suitable both for acute and for long-term therapy.

The compounds of the formula I can also be employed in combination with active ingredients which act by antithrombotic principles different from PAR1.

1) The invention therefore relates to a compound of the formula I

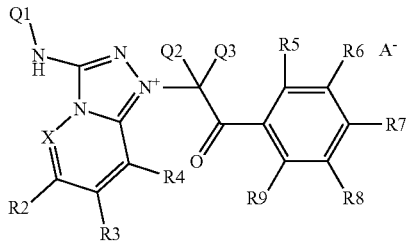

and/or any stereoisomeric or tautomeric forms of the compound of the formula I and/or mixtures of these forms in any ratio, and/or a physiologically compatible salt of the compound of the formula I, where X is C—R1 or N, $A^-$ is an anion of an organic or inorganic acid, Q1 is a hydrogen atom, —$(C_1-C_6)$-alkyl, —$(C_3-C_6)$-cycloalkyl, —$(C_0-C_4)$-alkylene-C(O)—R11, $(C_0-C_4)$-alkylene-C(O)—N(R11)-R12, —$(C_0-C_4)$-alkylene-C(O)—R11, —OH, —O—$(C_1-C_6)$-alkyl or —O—$(C_3-C_6)$-cycloalkyl, where alkyl and cycloalkyl are each unsubstituted or mono-, di- or trisubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in alkyl or cycloalkyl may be replaced by fluorine, Q2 and Q3 are the same or different and are each independently a hydrogen atom, —$(C_1-C_6)$-alkyl or —$(C_3-C_6)$-cycloalkyl, where some or all of the hydrogen atoms in alkyl or cycloalkyl may be replaced by fluorine, R1, R2, R3 and R4 are the same or different and are each independently a hydrogen atom, —$(C_1-C_6)$-alkyl, —$(C_3-C_6)$-cycloalkyl, —O—$(C_1-C_8)$-alkyl, —O—$(C_3-C_6)$-cycloalkyl, —$(C_0-C_4)$-alkylene-C(O)—N(R11)-R12, —$(C_0-C_4)$-alkylene-C(O)—O—R11, —$(C_0-C_4)$-alkylene-N(R11)-C(O)—O—R12, —$(C_0-C_4)$-alkylene-C(O)—R11, —$(C_0-C_4)$-alkylene-N(R11)-R12, —$(C_0-C_4)$-alkylene-N(R11)-C(O)—R12, halogen, OH, —CN, —$NO_2$, —$SO_2CH_3$, —$SO_2CF_3$, —$SF_5$, —Si[—$(C_1-C_4)$-alkyl]$_3$, —$(C_1-C_6)$-alkylene-O—$(C_1-C_6)$-alkyl, —O—$(C_1-C_6)$-alkylene-O—$(C_1-C_6)$-alkyl, —O—$(C_0-C_4)$-alkylene-$(C_6-C_{14})$-aryl where aryl is unsubstituted or mono-, di- or trisubstituted independently by —O—$(C_1-C_6)$-alkyl, —$(C_1-C_4)$-alkyl, OH, —$(C_3-C_6)$-cycloalkyl or —O—$(C_3-C_6)$-cycloalkyl, —O—$(C_1-C_4)$-alkylene-$(C_3-C_6)$-cycloalkyl, —$(C_4-C_{15})$-Het, where Het is unsubstituted or mono-, di- or trisubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, or —O—$(C_1-C_6)$-alkylene-O—$(C_1-C_6)$-alkylene-β-$(C_1-C_6)$-alkyl, where alkyl, alkylene and cycloalkyl are each unsubstituted or mono-, di- or trisubstituted independently by —$(C_1-C_4)$-alkyl, —$(C_3-C_6)$-cycloalkyl, OH, —O—$(C_1-C_6)$-alkyl, —$(C_6-C_{14})$-aryl where aryl is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, —$(C_4-C_{15})$-Het where Het is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, —O—$(C_3-C_6)$-cycloalkyl, where some or all of the hydrogen atoms in alkyl, alkylene or cycloalkyl may be replaced by fluorine, or R1 and R2, R2 and R3 or R3 and R4, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in the 5- to 8-membered ring formed, and in alkyl or cycloalkyl, may be replaced by fluorine, R11 and R12 (should also apply to Q1!) are each independently a hydrogen atom, —$(C_1-C_6)$-alkyl, —$(C_3-C_6)$-cycloalkyl, —$(C_0-C_4)$-alkylene-$(C_6-C_{14})$-aryl, —$(C_0-C_4)$-alkylene-$(C_4-C_{15})$-Het, —$SO_2CH_3$ or —$SO_2CF_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in the 5- to 8-membered ring formed, and in alkyl or cycloalkyl, may be replaced by fluorine, R5, R6, R7, R8 and R9 are the same or different and are each independently a hydrogen atom, —$(C_1-C_6)$-alkyl, —$(C_3-C_6)$-cycloalkyl, OH, —CN, —$NO_2$, —O—$(C_1-C_8)$-alkyl, —O—$(C_3-C_6)$-cycloalkyl, —$(C_0-C_4)$-alkylene-(CO)—N(R21)-R22, —$SO_2CH_3$, —$SO_2CF_3$, —$(C_0-C_4)$-alkylene-C(O)—O—R21, halogen, —$SF_5$, —$(C_0-C_4)$-alkylene-C(O)—R21, —$(C_0-C_4)$-alkylene-N(R21)-R22, —$(C_0-C_4)$-alkylene-N(R21)-C(O)—R22, —$(C_1-C_6)$-alkylene-β-$(C_1-C_6)$-alkyl, —$(C_0-C_6)$-alkylene-O—$(C_1-C_6)$-alkylene-O—$(C_1-C_6)$-alkyl, —Si[—$(C_1-C_4)$-alkyl]$_3$, —$(C_0-C_6)$-alkylene-O—$(C_1-C_4)$-alkylene-$(C_3-C_6)$-cycloalkyl, —$(C_0-C_6)$-alkylene-O—$(C_0-C_6)$-alkylene-$(C_6-C_{14})$-aryl or —$(C_4-C_{15})$-Het, where alkyl, alkylene and cycloalkyl are each unsubstituted or mono-, di- or trisubstituted independently by —$(C_1-C_4)$-alkyl, —$(C_3-C_6)$-cycloalkyl, OH, —O—$(C_1-C_6)$-alkyl, —$(C_6-C_{14})$-aryl where aryl is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, —($C_4$-$C_{15}$)-Het where Het is unsubstituted or mono-, di-, tri-, tetra- or pentasubstituted independently by halogen, —($C_1$-$C_4$)-alkyl,
—($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine, or R5 and R6, R6 and R7, R7 and R8 or R8 and R9, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

2) Preference is given to a compound of the formula I wherein
X is C—R1 or N,
$A^-$ is an anion of an organic or inorganic acid,
Q1 is a hydrogen atom, —($C_1$-$C_6$)-alkyl, —($C_3$-$C_6$)-cycloalkyl,
—($C_0$-$C_4$)-alkylene-C(O)—O—R11, —($C_0$-$C_4$)-alkylene-C(O)—N(R11)-R12, —($C_0$-$C_4$)-alkylene-C(O)—R11, —OH, —O—($C_1$-$C_6$)-alkyl or
—O—($C_3$-$C_6$)-cycloalkyl, where alkyl and cycloalkyl are each unsubstituted or mono-, di- or trisubstituted independently by —($C_1$-$C_4$)-alkyl,
—($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine,
Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine,
R1, R2, R3 and R4 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-N(R11)-C(O)—O—R12, —($C_0$-$C_4$)-alkylene-C(O)—O—R11, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —$SO_2CF_3$, —$SF_5$, —Si[—($C_1$-$C_4$)-alkyl]$_3$, —($C_1$-$C_6$)-alkylene-O—($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —O—($C_1$-$C_4$)-alkylene-($C_3$-$C_6$)-cycloalkyl, —($C_4$-$C_{15}$)-Het,
where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkylene-O—($C_1$-$C_6$)-alkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine,
with the proviso that at least one R1, R2, R3 or R4 is not a hydrogen atom or R1 and R2, R2 and R3 or R3 and R4, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R4, R5, R6, R7, R8 and R9 are the same or different and are each independently a hydrogen atom, —($C_1$-$C_6$)-alkyl, —($C_3$-$C_6$)-cycloalkyl, OH, —CN, —$NO_2$, —O—($C_1$-$C_8$)-alkyl, —O—($C_3$-$C_6$)-cycloalkyl, —($C_0$-$C_4$)-alkylene-C(O)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —($C_0$-$C_6$)-alkylene-O—($C_1$-$C_6$)-alkylene-O—($C_1$-$C_6$)-alkyl, —Si[—($C_1$-$C_4$)-alkyl]$_3$, —($C_0$-$C_6$)-alkylene-O—($C_1$-$C_4$)-alkylene-($C_3$-$C_6$)-cycloalkyl, —($C_0$-$C_6$)-alkylene-O—($C_0$-$C_6$)-alkylene-($C_6$-$C_{14}$)-aryl or —($C_4$-$C_{15}$)-Het,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen,
—($C_1$-$C_4$)-alkyl, —($C_3$-$C_6$)-cycloalkyl, OH, —O—($C_1$-$C_6$)-alkyl or
—O—($C_3$-$C_6$)-cycloalkyl,
—($C_4$-$C_{15}$)-Het where Het is unsubstituted or mono-, di-, tri-, tetra- or pentasubstituted independently by halogen,
—($C_1$-$C_4$)-alkyl,
—($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine,
with the proviso that at least one R5, R6, R7, R8 or R9 is not a hydrogen atom, or
R5 and R6, R6 and R7, R7 and R8 or R8 and R9, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine,
R21 and R22 are each independently a hydrogen atom, —($C_1$-$C_6$)-alkyl,
—($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or
R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

3) Particular preference is given to a compound of the formula I, wherein
X is C—R1 or N,
$A^-$ is an anion of an organic or inorganic acid,
Q1 is a hydrogen atom, —($C_1$-$C_6$)-alkyl, —($C_3$-$C_6$)-cycloalkyl, —($C_0$-$C_4$)-alkylene-C(O)—O—R11, —($C_0$-$C_4$)-alkylene-C(O)—N(R11)-R12, —($C_0$-$C_4$)-alkylene-C(O)—R11, —OH, —O—($C_1$-$C_6$)-alkyl or
—O—($C_3$-$C_6$)-cycloalkyl, where alkyl and cycloalkyl are each unsubstituted or mono-, di- or trisubstituted independently by —($C_1$-$C_4$)-alkyl,
—($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine,
Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine,
R1, R2, R3 and R4 are the same or different and are each independently a hydrogen atom, —($C_1$-$C_6$)-alkyl, —($C_3$-$C_6$)-cycloalkyl, —O—($C_1$-$C_8$)-alkyl,
—O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-N(R11)-C(O)—O—R12, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —Si[—($C_1$-$C_4$)-alkyl]$_3$, —($C_1$-$C_6$)-alkylene-β-($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl, —O—($C_1$-$C_4$)-alkylene-($C_3$-$C_6$)-cycloalkyl, —($C_4$-$C_{15}$)-Het or —O—($C_1$-$C_6$)-alkylene-O—($C_1$-$C_6$)-alkylene-O—($C_1$-$C_6$)-alkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
where some or all of the hydrogen atoms in alkyl, alkylene or cycloalkyl may be replaced by fluorine,
with the proviso that at least one R1, R2, R3 or R4 is not a hydrogen atom or
R1 and R2, R2 and R3 or R3 and R4, together with the ring atoms to which they are each bonded, form a ring selected from the group of 2,3,5,6,7,8-hexahydro-1,2,3a,4,5,8-hexaaza-cyclopenta[b]naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaaza-cyclopenta[a]-naphthalene; 2,3-dihydro-5,7-dioxa-1,2,3a,4-tetraaza-s-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine and 2,3,6a,9a-tetrahydro-[1,3]dioxolo[4,5-d][1,2,4]triazolo[4,3-b]pyridazine, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine,
R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or
R11 and R12 in the "N(R11)-R12" and "N(R11)-C(O)—R12" fragments represent a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl where some or all of the hydrogen atoms in the 5- to 8-membered ring formed, and in alkyl or cycloalkyl, may be replaced by fluorine,
R4, R5, R6, R7, R8 and R9 are the same or different and are each independently a hydrogen atom, —($C_1$-$C_6$)-alkyl, —($C_3$-$C_6$)-cycloalkyl, OH, —CN, —$NO_2$,
—O—($C_1$-$C_8$)-alkyl, —O—($C_3$-$C_6$)-cycloalkyl, —$SO_2CH_3$, —$SO_2CF_3$, —($C_0$-$C_4$)-alkylene-(CO)—N(R21)-R22, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —($C_0$-$C_6$)-alkylene-O—($C_1$-$C_6$)-alkylene-O—

$(C_1-C_6)$-alkyl, $-Si[-(C_1-C_4)-alkyl]_3$, $-(C_0-C_6)$-alkylene-O—$(C_1-C_4)$-alkylene-$(C_3-C_6)$-cycloalkyl, $-(C_0-C_6)$-alkylene-O—$(C_0-C_6)$-alkylene-$(C_6-C_{14})$-aryl or $-(C_4-C_{15})$-Het, where alkyl, alkylene and cycloalkyl are each unsubstituted or mono-, di- or trisubstituted independently by $-(C_1-C_4)$-alkyl, $-(C_3-C_6)$-cycloalkyl, OH, —O—$(C_1-C_6)$-alkyl, $-(C_6-C_{14})$-aryl where aryl is unsubstituted or mono-, di-, tri-, tetra- or pentasubstituted independently by halogen,
$-(C_1-C_4)$-alkyl, $-(C_3-C_6)$-cycloalkyl, OH, —O—$(C_1-C_6)$-alkyl or
—O—$(C_3-C_6)$-cycloalkyl,
$-(C_4-C_{15})$-Het where Het is unsubstituted or mono-, di-, tri-, tetra- or pentasubstituted independently by halogen,
$-(C_1-C_4)$-alkyl,
$-(C_3-C_6)$-cycloalkyl, OH, —O—$(C_1-C_6)$-alkyl or —O—$(C_3-C_6)$-cycloalkyl, or —O—$(C_3-C_6)$-cycloalkyl,
where some or all of the hydrogen atoms in alkyl, alkylene or cycloalkyl may be replaced by fluorine, with the proviso that at least one R5, R6, R7, R8 or R9 is not a hydrogen atom, or R5 and R6, R6 and R7, R7 and R8 or R8 and R9, together with the ring atoms to which they are each bonded, form a 5- to 8-membered ring selected from the group of 2,3-dihydrobenzo[1,4]dioxin; 3,4-dihydro-2H-benzo[1,4]oxazine; 1,2,3,4-tetrahydro-quinoxaline; benzo[1,3]dioxole; 3,4-dihydro-2H-benzo[1,4]thiazine and 2,3,4,5-tetrahydro-1H-benzo[b][1,4]diazepine, where the ring is unsubstituted or mono- or disubstituted independently by $-(C_1-C_4)$-alkyl, $-(C_3-C_6)$-cycloalkyl, OH, —O—$(C_1-C_6)$-alkyl or —O—$(C_3-C_6)$-cycloalkyl, where some or all of the hydrogen atoms in the 5- to 8-membered ring formed, and in alkyl or cycloalkyl, may be replaced by fluorine, R21 and R22 are each independently a hydrogen atom, $-(C_1-C_6)$-alkyl,
$-(C_3-C_6)$-cycloalkyl, $-(C_0-C_4)$-alkylene-$(C_6-C_{14})$-aryl, $-(C_0-C_4)$-alkylene-$(C_4-C_{15})$-Het, $-SO_2CH_3$ or $-SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by $-(C_1-C_4)$-alkyl, $-(C_3-C_6)$-cycloalkyl, OH, —O—$(C_1-C_6)$-alkyl or —O—$(C_3-C_6)$-cycloalkyl, where some or all of the hydrogen atoms in the 5- to 8-membered ring formed, and in alkyl or cycloalkyl, may be replaced by fluorine.

4) The invention further relates to a compound of the formula I, wherein

X is C—R1 or N,

A⁻ is an anion of an organic or inorganic acid,

Q1 is a hydrogen atom, $-(C_1-C_6)$-alkyl, $-(C_3-C_6)$-cycloalkyl, $-(C_0-C_4)$-alkylene-C(O)—O—R11, $-(C_0-C_4)$-alkylene-C(O)—N(R11)-R12, $-(C_0-C_4)$-alkylene-C(O)—R11, —OH, —O—$(C_1-C_6)$-alkyl or
—O—$(C_3-C_6)$-cycloalkyl, where alkyl and cycloalkyl are each unsubstituted or mono-, di- or trisubstituted independently by $-(C_1-C_4)$-alkyl,
$-(C_3-C_6)$-cycloalkyl, OH, —O—$(C_1-C_6)$-alkyl or —O—$(C_3-C_6)$-cycloalkyl, where some or all of the hydrogen atoms in alkyl or cycloalkyl may be replaced by fluorine, Q2 and Q3 are the same or different and are each independently a hydrogen atom, $-(C_1-C_6)$-alkyl or $-(C_3-C_6)$-cycloalkyl, where some or all of the hydrogen atoms in alkyl or cycloalkyl may be replaced by fluorine, R1, R2, R3 and R4 are the same or different and are each independently a hydrogen atom, $-(C_1-C_4)$-alkyl, —O—$(C_1-C_8)$-alkyl, —O—$(C_3-C_6)$-cycloalkyl, $-(C_0-C_4)$-alkylene-C(O)—N(R11)-R12, $-(C_0-C_4)$-alkylene-C(O)—O—R11, $-CF_3$, $-(C_0-C_4)$-alkylene-N(R11)-C(O)—O—R12, $-(C_0-C_4)$-alkylene-N(R11)-R12, chlorine, —O—$(C_1-C_6)$-alkylene-O—$(C_1-C_6)$-alkyl, —O—$(C_0-C_4)$-alkylene-$(C_6-C_{14})$-aryl or $-(C_4-C_{15})$-Het where Het is selected from the group of acridinyl, azepinyl, azetidinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrol, thienopyridin, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl, where alkylene is unsubstituted or monosubstituted by $-(C_1-C_4)$-alkyl or $-(C_3-C_6)$-cycloalkyl, or some or all of the hydrogen atoms in alkylene are replaced by fluorine, R11 and R12 are each independently a hydrogen atom or $-(C_1-C_6)$-alkyl, R5, R6, R7, R8 and R9 are the same or different and are each independently a hydrogen atom, $-(C_1-C_6)$-alkyl, OH, —O—$(C_1-C_8)$-alkyl, chlorine, bromine, $-SF_5$, $-(C_0-C_4)$-alkylene-N(R21)-R22, $-(C_0-C_4)$-alkylene-N(R21)-C(O)—R22, $(C_0-C_6)$-alkylene-O—$(C_1-C_6)$-alkylene-O—$(C_1-C_6)$-alkyl, $-(C_4-C_{15})$-Het, $-(C_0-C_6)$-alkylene-O—$(C_1-C_4)$-alkylene-$(C_3-C_6)$-cycloalkyl, $-CF_3$— or $-(C_0-C_6)$-alkylene-O—$(C_0-C_6)$-alkylene-$(C_6-C_{14})$-aryl, where alkylene is unsubstituted or monosubstituted by —O—$(C_1-C_6)$-alkyl, with the proviso that at least one R5, R6, R7, R8 or R9 is not a hydrogen atom, R5 and R6, R6 and R7 or R7, or R8 and R9, together with the ring atoms to which they are each bonded, form a morpholine ring, where the ring is unsubstituted or monosubstituted by —($C_1$-$C_4$)-alkyl, R21 and R22 are each independently a hydrogen atom or —($C_1$-$C_6$)-alkyl.

5) Exceptionally preferred are compounds of the formula I including the following compounds:

1-{2-[3-acetylamino-5-(pentafluorosulfanyl)phenyl]-2-oxoethyl}-3-amino-6-ethoxy-[1,2,4]-triazolo[4,3-b]pyridazin-1-ium as trifluoroacetic acid salt, 3-amino-1-[2-(3,5-di-tert-butyl-4-hydroxyphenyl)-2-oxoethyl]-6-trifluoromethyl-[1,2,4]triazolo[4,3-a]pyridin-1-ium, 3-amino-1-[2-(3,5-di-tert-butyl-4-hydroxyphenyl)-2-oxoethyl]-[1,2,4]triazolo[4,3-a]pyridin-1-ium, 3-amino-1-[2-(3-tert-butyl-4-methoxy-5-morpholin-4-ylphenyl)-2-oxoethyl]-6-trifluoromethyl-[1,2,4]triazolo[4,3-a]pyridin-1-ium, 3-amino-1-[2-(3-tert-butyl-4-methoxy-5-morpholin-4-ylphenyl)-2-oxoethyl]-5-methyl-7-trifluoromethyl-[1,2,4]triazolo[4,3-a]pyridin-1-ium, 3-amino-5-chloro-1-{2-[3-methylamino-5-(pentafluorosulfanyl)phenyl]-2-oxoethyl}-[1,2,4]triazolo[4,3-a]pyridin-1-ium, 3-amino-7-ethoxy-6-ethoxycarbonyl-1-{2-[3-methylamino-5-(pentafluorosulfanyl)phenyl]-2-oxoethyl}-[1,2,4]triazolo[4,3-a]pyridin-1-ium, 3-amino-1-[2-(3-tert-butyl-4-methoxy-5-morpholin-4-ylphenyl)-2-oxoethyl]-7-ethoxy-6-ethoxycarbonyl-[1,2,4]triazolo[4,3-a]pyridin-1-ium, 3-amino-1-[2-(3-tert-butyl-4-methoxy-5-morpholin-4-ylphenyl)-2-oxoethyl]-7-ethoxy-6-methylcarbamoyl-[1,2,4]triazolo[4,3-a]pyridin-1-ium, 3-amino-6-chloro-1-[2-(3,5-di-tert-butyl-4-hydroxyphenyl)-2-oxoethyl]-[1,2,4]triazolo[4,3-b]pyridazin-1-ium, 3-amino-1-[2-(3-tert-butyl-4-methoxy-5-morpholin-4-ylphenyl)-2-oxo-ethyl]-6-ethoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-isopropoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-methoxy-[1,2,4]triazolo[4,3-b]pyridazin-1-ium, 3-amino-6-ethoxy-1-[2-(4-methoxy-3-morpholin-4-yl-5-trifluoromethylphenyl)-2-oxoethyl]-[1,2,4]triazolo[4,3-b]pyridazin-1-ium, 1-{2-[3-acetylamino-5-(pentafluorosulfanyl)phenyl]-2-oxoethyl}-3-amino-6-ethoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclopentyloxy-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclobutoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-phenoxy-[1,2,4]triazolo[4,3-b]pyridazin-1-ium, 3-amino-6-benzyloxy-1-[2-(3-tert-butyl-4-methoxy-5-morpholin-4-ylphenyl)-2-oxoethyl]-[1,2,4]triazolo[4,3-b]pyridazin-1-ium, 3-amino-1-[2-(3-tert-butyl-4-methoxy-5-morpholin-4-ylphenyl)-2-oxoethyl]-6-(1-ethylpropoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclohexyloxy-[1,2,4]triazolo[4,3-b]pyridazin-1-ium, 3-amino-1-[2-(3-tert-butyl-4-methoxy-5-morpholin-4-ylphenyl)-2-oxoethyl]-6-(2,2,2-trifluoroethoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclopropyl-methoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-ethoxy-[1,2,4]triazolo[4,3-b]pyridazin-1-ium, 3-amino-6-(1-ethyl-propoxy)-1-{2-[3-methylamino-5-(pentafluorosulfanyl)phenyl]-2-oxoethyl}-[1,2,4]triazolo[4,3-b]pyridazin-1-ium, 3-amino-6-(1-ethylpropoxy)-1-{2-[3-methoxy-5-(pentafluorosulfanyl)phenyl]-2-oxoethyl}-[1,2,4]triazolo[4,3-b]pyridazin-1-ium, 3-amino-1-[2-(3-tert-butyl-5-ethoxymethylphenyl)-2-oxoethyl]-6-(1-ethylpropoxy)-[1,2,4]triazolo[4,3-b]pyridazin-1-ium, 3-amino-1-[2-(3-tert-butyl-5-cyclopropylmethoxymethylphenyl)-2-oxoethyl]-6-(1-ethylpropoxy)-[1,2,4]triazolo[4,3-b]pyridazin-1-ium, 3-amino-1-[2-(3-tert-butyl-4,5-diethoxyphenyl)-2-oxoethyl]-6-(1-ethylpropoxy)-[1,2,4]triazolo[4,3-b]pyridazin-1-ium, 3-amino-1-[2-(3-tert-butyl-4,5-biscyclopropylmethoxyphenyl)-2-oxoethyl]-6-(1-ethylpropoxy)-[1,2,4]triazolo[4,3-b]pyridazin-1-ium, 3-amino-1-[2-(3-tert-butyl-5-propoxymethylphenyl)-2-oxoethyl]-6-(1-ethylpropoxy)-[1,2,4]triazolo[4,3-b]pyridazin-1-ium, 3-amino-1-[2-(3-tert-butyl-5-ethoxyphenyl)-2-oxoethyl]-6-(1-ethylpropoxy)-[1,2,4]triazolo-[4,3-b]pyridazin-1-ium, 3-amino-6-(1-ethylpropoxy)-1-[2-(3-methoxy-5-trifluoromethylphenyl)-2-oxoethyl]-[1,2,4]triazolo[4,3-b]pyridazin-1-ium, 3-amino-1-[2-(3-tert-butyl-5-methoxyphenyl)-2-oxoethyl]-6-(1-ethylpropoxy)-[1,2,4]triazolo[4,3-b]pyridazin-1-ium, 3-amino-1-[2-(3-tert-butyl-5-cyclopropylmethoxyphenyl)-2-oxoethyl]-6-(1-ethylpropoxy)-[1,2,4]triazolo[4,3-b]pyridazin-1-ium, 3-amino-1-[2-(3-tert-butyl-5-cyclobutylmethoxyphenyl)-2-oxoethyl]-6-(1-ethylpropoxy)-[1,2,4]triazolo[4,3-b]pyridazin-1-ium, 3-amino-1-[2-(3-benzyloxymethyl-5-tert-butylphenyl)-2-oxoethyl]-6-(1-ethylpropoxy)-[1,2,4]triazolo[4,3-b]pyridazin-1-ium, 3-amino-1-[2-(3-cyclohexylmethoxy-4,5-dimethoxyphenyl)-2-oxoethyl]-6-(1-ethylpropoxy)-[1,2,4]triazolo[4,3-b]pyridazin-1-ium, 3-amino-6-butoxy-1-[2-(3-tert-butyl-5-methoxymethylphenyl)-2-oxoethyl]-[1,2,4]triazolo[4,3-b]pyridazin-1-ium, 3-amino-1-[2-(3-chloro-5-methoxyphenyl)-2-oxoethyl]-6-(1-ethylpropoxy)-[1,2,4]triazolo[4,3-b]pyridazin-1-ium, 3-amino-1-[2-(8-tert-butyl-4-methyl-3,4-dihydro-2H-benzo[1,4]oxazin-6-yl)-2-oxoethyl]-6-(1-ethylpropoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-diethylamino-[1,2,4]triazolo[4,3-b]pyridazin-1-ium, 3-amino-1-[2-(3-tert-butyl-4-methoxy-5-morpholin-4-ylphenyl)-2-oxoethyl]-6-piperidin-1-yl-[1,2,4]triazolo[4,3-b]pyridazin-1-ium, 3-amino-1-[2-(3-tert-butyl-4-methoxy-5-morpholin-4-ylphenyl)-2-oxoethyl]-6-ethoxy-[1,2,4]triazolo[4,3-a]pyridin-1-ium,
3-amino-1-[2-(3-cyclohexylmethoxy-5-ethoxyphenyl)-2-oxoethyl]-6-(1-ethylpropoxy)-[1,2,4]triazolo[4,3-b]pyridazin-1-ium,
3-amino-1-[2-(3-bromo-5-methoxyphenyl)-2-oxoethyl]-6-(1-ethylpropoxy)-[1,2,4]triazolo-[4,3-b]pyridazin-1-ium,
3-amino-6-(1-ethylpropoxy)-1-[2-(3-isopropyl-5-methoxyphenyl)-2-oxoethyl]-[1,2,4]triazolo-[4,3-b]pyridazin-1-ium,
3-amino-1-[2-(3-cyclohexylmethoxy-5-methoxyphenyl)-2-oxoethyl]-6-(1-ethylpropoxy)-[1,2,4]triazolo[4,3-b]pyridazin-1-ium,
3-amino-1-{2-[3-(3,3-dimethylbutoxy)-5-ethoxyphenyl]-2-oxoethyl}-6-(1-ethylpropoxy)-[1,2,4]triazolo[4,3-b]pyridazin-1-ium,
3-amino-1-[2-(8-tert-butyl-4-methyl-3,4-dihydro-2H-benzo[1,4]oxazin-6-yl)-2-oxoethyl]-6-ethoxy-[1,2,4]triazolo[4,3-a]pyridin-1-ium,
3-amino-6-diethylamino-1-{2-[3-methoxy-5-(pentafluorosulfanyl)phenyl]-2-oxoethyl}-[1,2,4]triazolo[4,3-b]pyridazin-1-ium,
3-amino-1-[2-(3-tert-butyl-4-methoxy-5-morpholin-4-ylphenyl)-2-oxoethyl]-6-morpholin-4-yl-[1,2,4]triazolo[4,3-b]pyridazin-1-ium,
3-amino-1-[2-(5-bromo-2,3-dimethoxyphenyl)-2-oxoethyl]-6-(1-ethylpropoxy)-[1,2,4]triazolo[4,3-b]pyridazin-1-ium,
3-amino-1-[2-(3-chloro-4,5-dimethoxyphenyl)-2-oxoethyl]-6-(1-ethylpropoxy)-[1,2,4]-triazolo[4,3-b]pyridazin-1-ium,
3-amino-1-{2-[3-tert-butyl-5-(2-methoxyethoxy)phenyl]-2-oxoethyl}-6-(1-ethylpropoxy)-[1,2,4]triazolo[4,3-b]pyridazin-1-ium,
3-amino-1-[2-(3-tert-butyl-5-methoxyphenyl)-2-oxoethyl]-6-(2-methoxyethoxy)-[1,2,4]triazolo[4,3-b]pyridazin-1-ium,
3-amino-1-[2-(3-tert-butyl-5-methoxymethylphenyl)-2-oxoethyl]-6-(2-methoxy-ethoxy)-[1,2,4]triazolo[4,3-b]pyridazin-1-ium,
3-amino-1-[2-(3-tert-butyl-4-methoxy-5-morpholin-4-yl-phenyl)-2-oxoethyl]-6-chloro-[1,2,4]triazolo[4,3-b]pyridazin-1-ium,
3-amino-6-(1-ethylpropoxy)-1-{2-[3-morpholin-4-yl-5-(pentafluorosulfanyl)phenyl]-2-oxoethyl}-[1,2,4]triazolo[4,3-b]pyridazin-1-ium,
3-amino-6-ethyl-1-{2-[3-methoxy-5-(pentafluorosulfanyl)phenyl]-2-oxoethyl}-[1,2,4]triazolo[4,3-b]pyridazin-1-ium,
3-amino-1-[2-(3-tert-butyl-4-methoxy-5-morpholin-4-ylphenyl)-2-oxoethyl]-6-ethyl-[1,2,4]triazolo[4,3-b]pyridazin-1-ium,
3-amino-6-chloro-7-diethylcarbamoyl-1-{2-[3-methoxy-5-(pentafluorosulfanyl)phenyl]-2-oxoethyl}-[1,2,4]triazolo[4,3-b]pyridazin-1-ium or
3-amino-1-[2-(3-tert-butyl-4-methoxy-5-morpholin-4-ylphenyl)-2-oxoethyl]-6-chloro-7-diethylcarbamoyl-[1,2,4]triazolo[4,3-b]pyridazin-1-ium.

The term "anion" is understood to mean anions of organic and inorganic acids, particular preference being given to chloride. Examples of inorganic or organic acids are hydrochloric acid, hydrobromic acid, sulfuric acid, hemisulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, 2-hydroxyethanesulfonic acid, acetic acid, oxalic acid, tartaric acid, succinic acid, glycerolphosphoric acid, lactic acid, malic acid, adipic acid, citric acid, fumaric acid, maleic acid, gluconic acid, glucuronic acid, palmitic acid or trifluoroacetic acid.

The expression "$(C_1-C_4)$-alkyl" or "$(C_1-C_6)$-alkyl" is understood to mean hydrocarbon radicals whose carbon chain is straight-chain or branched and contains from 1 to 4 carbon atoms or from 1 to 6 carbon atoms, for example methyl, ethyl, propyl, isopropyl, butyl, isobutyl, sec-butyl, tert-butyl, pentyl, isopentyl, neopentyl, 1-ethylpropyl, hexyl, 2,3-dimethylbutyl or neohexyl.

The expression "—$(C_0-C_4)$-alkylene" or "—$(C_1-C_6)$-alkylene" is understood to mean hydrocarbon radicals whose carbon chain is straight-chain or branched and contains 1 to 4 or 1-6 carbon atoms, for example methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethylethylene, 1-methylpropylene, 2-methylpropylene, pentylene, 1-methylbutylene, hexylene, 1-methylpentylene. "—$C_0$-alkylene" is a covalent bond.

The expression "—O—$(C_1-C_6)$-alkyl" or "—O—$(C_1-C_8)$-alkyl" is understood to mean alkoxy radicals whose carbon chain is straight-chain or branched and contains from 1 to 6 or from 1 to 8 carbon atoms, for example methoxy, ethoxy, propoxy, isopropoxy, butoxy, isobutoxy, tert-butoxy, 1-pentoxy, 2-pentoxy, 3-pentoxy, 1-hexoxy, 2-hexoxy, 3-hexoxy, 1-heptoxy, 2-heptoxy, 3-heptoxy, 4-heptoxy, 2,4-dimethylpentan-3-oxy, 1-octoxy, 2-octoxy, 3-octoxy, 2,2,4-trimethylpentan-3-oxy, 2,3,4-trimethylpentan-3-oxy or 4-octoxy.

The expression "$(C_3-C_6)$-cycloalkyl" is understood to mean radicals such as compounds which derive from 3- to 6-membered monocycles such as cyclopropane, cyclobutane, cyclopentane or cyclohexane.

The expression "—O—$(C_3-C_6)$-cycloalkyl" is understood to mean cycloalkoxy radicals such as compounds which derive from 3- to 6-membered monocycles such as cyclopropoxy, cyclobutoxy, cyclopentoxy or cyclohexoxy.

The expression "—$(C_6-C_{14})$-aryl" is understood to mean aromatic carbon radicals having from 6 to 14 carbon atoms in the ring. —$(C_6-C_{14})$-Aryl radicals are, for example, phenyl, naphthyl, for example 1-naphthyl, 2-naphthyl, anthryl or fluorenyl. Naphthyl radicals and especially phenyl are preferred aryl radicals.

The expression "Het" is understood to mean ring systems having from 4 to 15 carbon atoms which are present in one, two or three ring systems joined to one another and which, according to ring size, may contain one, two, three or four identical or different heteroatoms from the group of oxygen, nitrogen and sulfur. Examples of these ring systems are acridinyl, azepinyl, azetidinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1, 2,5-thiadiazolyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl radicals.

In the case that X is C—R1 and Y is C—R2 and R1 and R2 are each a hydrogen atom, this is understood to mean bicyclic ring systems which, together with the 4H-[1,2,4]triazol-3-ylamine in formula I form, for example, a [1,2,4]triazolo[4,3-a]pyrin-3-ylamine ring which has the following structure:

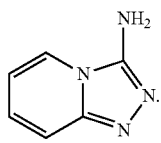

In the case that X is N and Y is C—R2 and R2 is a hydrogen atom, this is understood to mean bicyclic ring systems which, together with the 4H-[1,2,4]triazol-3-ylamine in formula I, form, for example, a [1,2,4]triazole[4,3-b]pyridazin-3-ylamine ring which has the following structure:

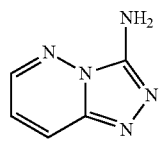

The expression "R1 and R2, R2 and R3 or R3 and R4, together with the ring atoms to which they are each bonded, form a 5- to 8-membered ring, where the ring consists only of carbon atoms or 1, 2 or 3 of these atoms are replaced by nitrogen, oxygen or sulfur atoms" is understood to mean, for example, ring systems such as 2,3,5,6,7,8-hexahydro-1,2,3a, 4,5,8-hexaaza-cyclopenta[b]naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaaza-cyclopenta[a]-naphthalene; 2,3-dihydro-5,7-dioxa-1,2,3a,4-tetraaza-s-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine or 2,3,6a,9a-tetrahydro-[1,3]dioxolo[4,5-d][1,2,4]-triazolo[4,3-b]pyridazine.

The expression "R5 and R6, R6 and R7, R7 and R8 or R8 and R9, together with the ring atoms to which they are each bonded, form a 5- to 8-membered ring, where the ring consists only of carbon atoms or 1, 2 or 3 of these atoms are replaced by nitrogen, oxygen or sulfur atoms" is understood to mean, for example, ring systems such as 2,3-dihydrobenzo[1,4]dioxin; 3,4-dihydro-2H-benzo[1,4]oxazine; 1,2,3,4-tetrahydroquinoxaline; benzo[1,3]dioxole; 3,4-dihydro-2H-benzo[1,4]thiazine or 2,3,4,5-tetrahydro-1H-benzo[b][1,4]diazepine.

The expressions "R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to 2 further heteroatoms from the group of N, O and S" or "R11 and R12 in the "N(R21)-R22" and "N(R21)-C(O)—R22" fragments is a 5- to 8-membered ring which is formed together with the nitrogen atom "N" or the "N—(CO)" group to form cyclic amines, imides or lactams which contain up to 2 further heteroatoms from the group of N, O and S" is understood to mean, for example, ring systems such as cyclic amines such as azetidinyl, pyrrolidinyl, piperidinyl, piperazinyl, azepinyl, morpholinyl or thiomorpholinyl, and in the case of the imides radicals such as pyrrolidine-2,5-dionyl, piperidine-2,6-dionyl, piperazine-2,6-dionyl, morpholine-3,5-dionyl, and in the case of the lactams radicals such as pyrrolidin-2-onyl, piperidin-2-onyl, piperazin-2-onyl, morpholin-3-onyl.

The rearranged expression "alkyl, alkylene or cycloalkyl some or all of the hydrogen atoms are replaced by fluorine" is understood to mean a partially fluorinated or perfluorinated alkyl, alkylene or cycloalkyl which derives, for example, for alkyl from the following radicals: —CF$_3$, —CHF$_2$, —CH$_2$F, —CHF—CF$_3$, —CHF—CHF$_2$, —CHF—CH$_2$F, —CH$_2$—CF$_3$, —CH$_2$—CHF$_2$, —CH$_2$—CH$_2$F, —CF$_2$—CF$_3$, —CF$_2$—CHF$_2$, —CF$_2$—CH$_2$F, —CH$_2$—CHF—CF$_3$, —CH$_2$—CHF—CHF$_2$, —CH$_2$—CHF—CH$_2$F, —CH$_2$—CH$_2$—CF$_3$, —CH$_2$—CH$_2$—CHF$_2$, —CH$_2$—CH$_2$—CH$_2$F, —CH$_2$—CF$_2$—CF$_3$, —CH$_2$—CF$_2$—CHF$_2$, —CH$_2$—CF$_2$—CH$_2$F, —CHF—CHF—CF$_3$, —CHF—CHF—CHF$_2$, —CHF—CHF—CH$_2$F, —CHF—CH$_2$—CF$_3$, —CHF—CH$_2$—CHF$_2$, —CHF—CH$_2$—CH$_2$F, —CHF—CF$_2$—CF$_3$, —CHF—CF$_2$—CHF$_2$, —CHF—CF$_2$—CH$_2$F, —CF$_2$—CHF—CF$_3$, —CF$_2$—CHF—CHF$_2$, —CF$_2$—CHF—CH$_2$F, —CF$_2$—CH$_2$—CF$_3$, —CF$_2$—CH$_2$—CHF$_2$, —CF$_2$—CH$_2$—CH$_2$F, —CF$_2$—CF$_2$—CF$_3$, —CF$_2$—CF$_2$—CHF$_2$, —CF$_2$—CF$_2$—CH$_2$F, —CH(CF$_3$)$_2$, —CH(CHF$_2$)$_2$, —CH(CFH$_2$)$_2$, —CH(CFH$_2$)(CHF$_2$), —CH(CFH$_2$)(CF$_3$), —CH(CFH$_2$)(CH$_3$), —CH(CHF$_2$)(CH$_3$), —CH(CF$_3$)(CH$_3$), —CF(CF$_3$)$_2$, —CF(CHF$_2$)$_2$, —CF(CFH$_2$)$_2$, —CF(CFH$_2$)(CHF$_2$), —CF(CFH$_2$)(CF$_3$), —CF(CFH$_2$)(CH$_3$), —CF(CHF$_2$)(CH$_3$), or —CF(CF$_3$)(CH$_3$), and also the further possible combinations for butyl, pentyl and hexyl, which, like propyl, may also be branched, for alkylene, for example, from the following radicals: —CF$_2$—, —CHF—, —CHF—CF$_2$—, —CHF—CHF—, —CHF—CH$_2$—, —CF$_2$—CF$_2$— or —CF$_2$—CH$_2$F, and also the further possible combinations for propylene, butylene, pentylene and hexylene, which may also be branched, and for cycloalkyl, for example, from the radicals

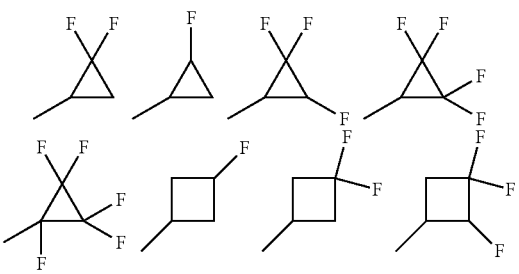

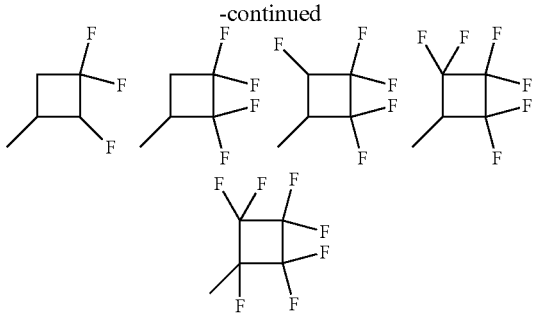

and also the analogous larger cyclopentyl and cyclohexyl rings.

The expression "halogen" is understood to mean fluorine, chlorine, bromine or iodine, preference being given to fluorine, chlorine or bromine, especially to fluorine or chlorine.

The expressions described above can also be combined as desired, as done, for example, in "—$(C_0-C_6)$-alkylene-O—$(C_0-C_6)$-alkylene-$(C_6-C_{14})$-aryl".

Functional groups of the intermediates used, for example amino or carboxyl groups in the compound of the formula I, may be masked by suitable protecting groups. Suitable protecting groups for amino functions are, for example, the t-butoxycarbonyl, the benzyloxycarbonyl or the phthaloyl group, and also the trityl or tosyl protecting group. Suitable protecting groups for the carboxyl function are, for example, alkyl, aryl or arylalkyl esters. Protecting groups can be introduced and removed by techniques which are well known or are described here (see Greene, T. W., Wuts, P. G. M., Protective Groups in Organic Synthesis (1999), 3rd Ed., Wiley-Interscience, or Kocienski, P. J., Protecting Groups (2004), 3rd Ed., Thieme. The expression "protecting group" may also include corresponding polymer-bound protecting groups.

The inventive compounds can be prepared by well-known processes or by processes described here.

The invention further relates to a process for preparing the compound of the formula I and/or a stereoisomeric form of the compound of the formula I and/or a physiologically compatible salt of the compound of the formula I, which comprises a) reacting a compound of the formula II

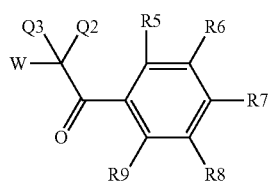

(II)

where R5, R6, R7, R8, R9, Q2 and Q3 are each as defined in formula I and W is chloride, bromide, mesylate or tosylate with a compound of the formula III

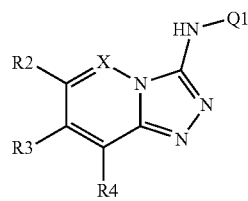

(III)

in which X, R2, R3 and R4 are each as defined in formula I, with or without addition of base, in a solvent to give a compound of the formula I, or b) either isolating the compound of the formula I prepared by method a) in free form or releasing it from physiologically incompatible salts or, in the case of the presence of acidic or basic groups, converting it to physiologically compatible salts, or c) separating a compound of the formula I prepared by method a), or a suitable precursor of the formula I which, owing to its chemical structure, occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and elimination of the chiral auxiliary groups.

The invention further relates to a process for preparing the compound of the formula I according to scheme 1.

Scheme 1:

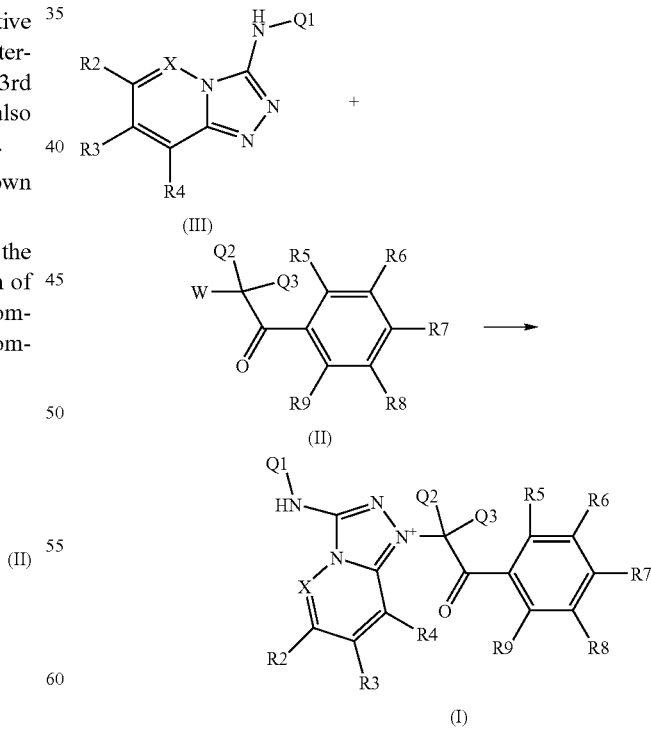

The reactants II and III, III optionally being present in the form of a salt, are converted at room temperature or a slightly elevated temperature from 40° C. to 60° C., advantageously, when III is in the form of a salt, in the presence of a base, preferably Hünig's base, in a solvent, preferably dimethylformamide (DMF) or dioxane, to give the compound of the formula I. The X, A⁻, Q1, Q2, Q3, R2, R3, R4, R5, R6, R7, R8 and R9 radicals are each as defined in formula I, W represents a good leaving group such as chloride, bromide, mesylate or tosylate, preferably bromide or mesylate.

The 2-substituted triazolopyridazines (A) which are likewise formed in different proportions under these reaction conditions according to the substitution pattern can be removed by chromatography or by crystallization. It is advantageous to separate by means of silica gel with dichloromethane-methanol as the eluent mixture.

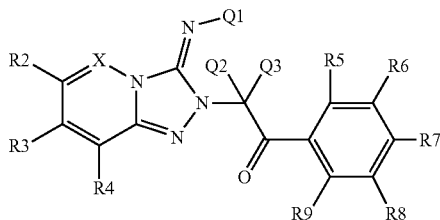

(A)

Hydrazines of the formula V type can be cyclized with cyano units of the Z—CN type to selectively form the 1-substituted cationic compounds of the formula I type where Q1 is hydrogen. Alternatively, it is possible to cyclize the hydrazines of the formula V type with isothiocyanates SCN-Q1' of the formula XXV type selectively to the 1-substituted cationic compounds of the formula I, in which case the thiourea formed as an intermediate can be cyclized with a "sulfur activator" such as tosyl chloride, a carbodiimide, ethyl bromoacetate or mercury oxide to give compounds of the formula I type. In this case, the X, A⁻, Q1, Q2, Q3, R2, R3, R4, R5, R6, R7, R8 and R9 radicals are each as defined above and Q' corresponds to Q1 or a protecting group such as FMOC (fluoren-9-ylmethyloxycarbonyl), which, after ring closure, can be detached again, such that compounds where Q1 is hydrogen are obtainable.

Scheme 2:

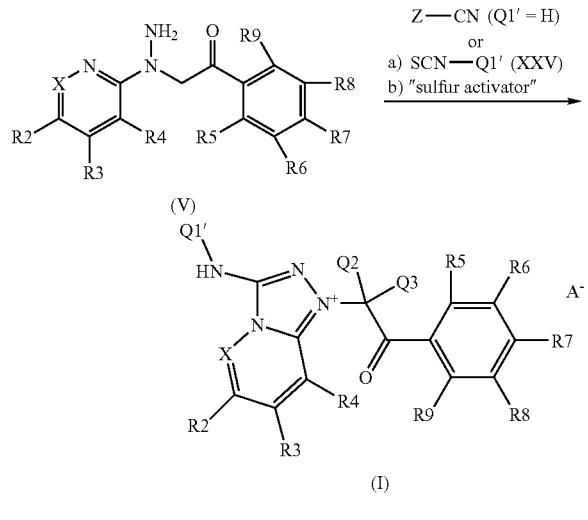

Compounds of the formula II can be obtained commercially or by literature methods, for example proceeding from the corresponding acetophenones X or X' (see, for example: Phosphorus and Sulfur and the Related Elements (1985), 25(3), 357 or Tetrahedron Letters (1984), 25(34), 3715). The well-known compounds of the formula X type, which are commercially available or can be synthesized in numerous structural variations, can, for example, be functionalized on the acetyl group with, among other reagents, elemental chlorine or bromine, tribromide derivatives such as phenyltrimethylammonium tribromide, 1,3-dichlorodimethylhydantoin, N-chloro- or N-bromosuccinimide. Compounds of the formula X' type can be converted, for example, using mesyl or tosyl chloride to the compounds of the II type.

Scheme 3:

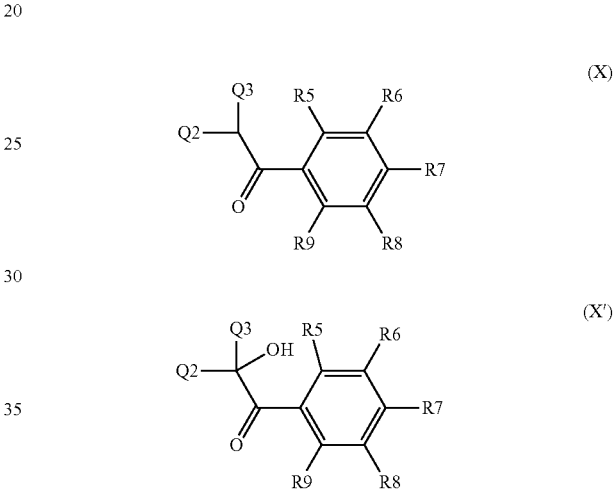

For particular R5 to R9 radicals, it may be more favorable first to convert the ketones of the X type to the ketals of the XI or XI' type, which can then be functionalized, preferably brominated, very selectively on the methyl group to give the compounds of the XII type, and, after deketalization with suitable acids, likewise lead to compounds of the II type.

The substituents in schemes 3 and 4 are each as defined above, T is a —(C₁-C₄)-alkyl group, while T' is ethylene, propylene or butylene, W' is a reactive compound such as phenyltrimethylammonium tribomide, N-bromosuccinimide or N-chlorosuccinimide.

Scheme 4:

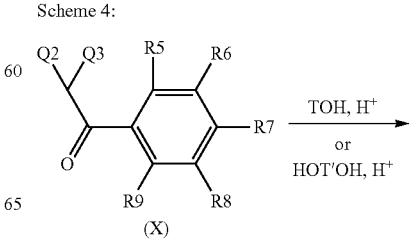

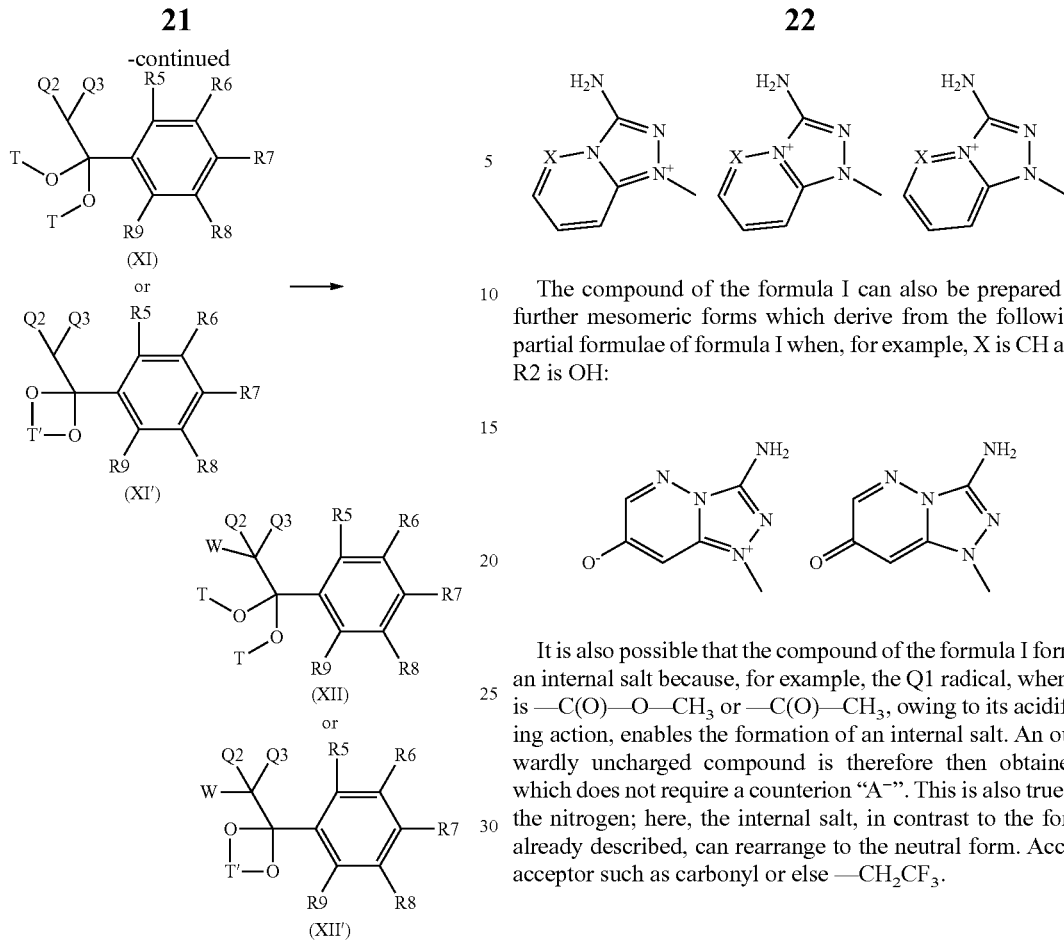

Compounds of the formula III can be obtained commercially or by literature methods. Suitable precursors are compounds of the XX type, which can be cyclized in the presence of cyanogen bromide, cyanogen chloride or tosyl cyanide to give compounds of the III type, and which may also be present in the tautomeric form of the XXa type.

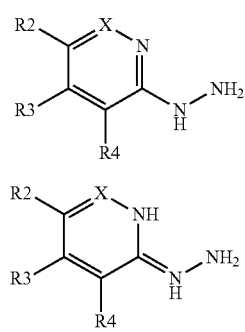

The compound of the formula XX such as pyridazin-3-ylhydrazine and the compound of the formula XXa such as [2H-pyridazin-(3E)-ylidene]hydrazine are tautomeric forms. When only one notation is utilized hereinafter, this means that the other tautomeric form is also disclosed.

The compound of the formula I can also be prepared in mesomeric forms which derive from the following partial formulae of formula I:

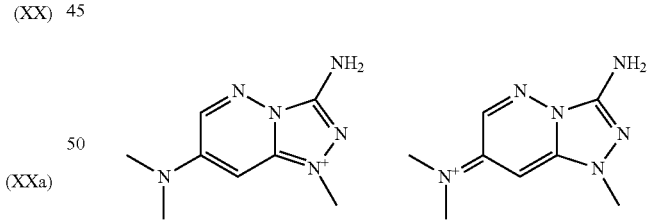

The compound of the formula I can also be prepared in further mesomeric forms which derive from the following partial formulae of formula I when, for example, X is CH and R2 is OH:

It is also possible that the compound of the formula I forms an internal salt because, for example, the Q1 radical, when it is —C(O)—O—CH$_3$ or —C(O)—CH$_3$, owing to its acidifying action, enables the formation of an internal salt. An outwardly uncharged compound is therefore then obtained, which does not require a counterion "A$^-$". This is also true of the nitrogen; here, the internal salt, in contrast to the form already described, can rearrange to the neutral form. Acc is acceptor such as carbonyl or else —CH$_2$CF$_3$.

Further mesomeric forms arise when the nitrogen cannot be stabilized by deprotonation.

When only one notation is used in this application, this means that the other mesomeric forms are also disclosed too.

Alternatively, compounds of the XX type can also be reacted with isothiocyanates of the XXV type to given the thioureas of the XXVI type. The latter can, after activation of the sulfur, for example with ethyl bromoacetate, a carbodiimide, tosyl chloride or mercury oxide, be converted to the compounds of the formula III type. The X, R2, R3 and R4 radicals here are each as defined above and Q1' corresponds to Q1 or a protecting group such as FMOC (fluoren-9-ylmethyloxycarbonyl), which, after ring closure, can be eliminated again, and so compounds where Q1 is hydrogen are obtainable.

Scheme 5:

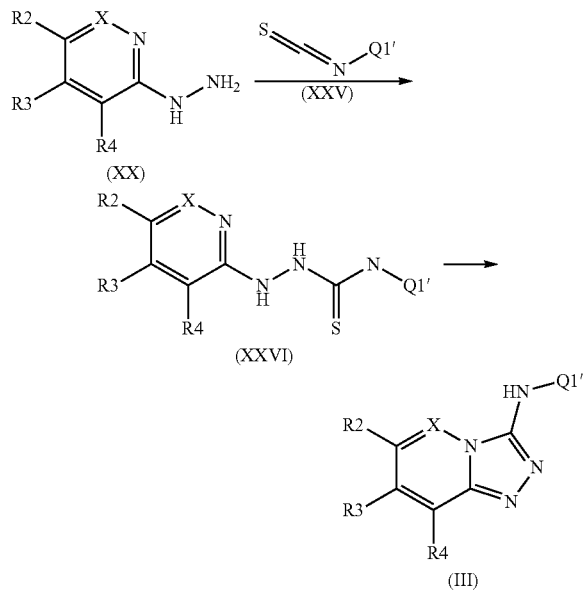

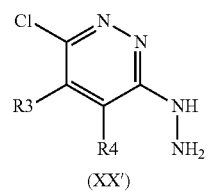

Compounds of the XX type can be obtained by incorporating hydrazine into compounds of the XXI type, which are commercially available with a wide variety of different substitution patterns. The X, R2, R3 and R4 radicals here are each as defined above and LG represents a good leaving group such as fluorine, chlorine, bromine, iodine, mesylate, tosylate, triflate or nonaflate.

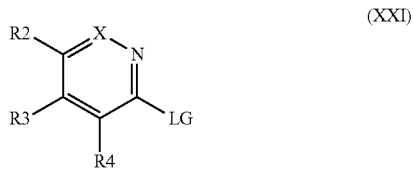

One route to the chlorine compounds of the XXI' type where X is nitrogen and R2 is chlorine is, for example, the reaction of maleic anhydrides of the XXIII type with hydrazine hydrochloride to give the compounds of the XXII type, followed by the reaction with phosphorus oxychloride to give the dichloride XXI' and with hydrazine to give the compounds of the XX' type where R2 is chlorine.

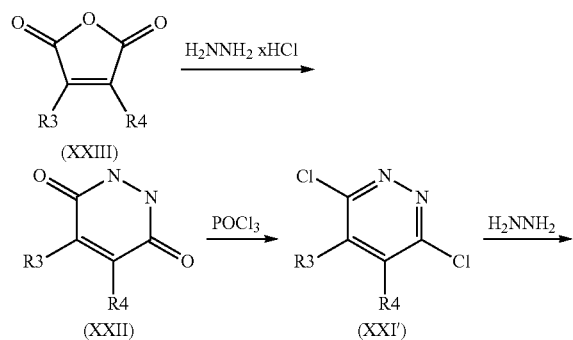

A compound of the formula I prepared according to scheme 1, or a suitable precursor of the formula I which, owing to its chemical structure, occurs in enantiomeric forms, can be separated into the pure enantiomers by salt formation with enantiomerically pure acids or bases, chromatography on chiral stationary phases or derivatization by means of chiral enantiomerically pure compounds such as amino acids, separation of the diastereomers thus obtained, and elimination of the chiral auxiliary groups (process c), or the compound of the formula I prepared according to scheme 1 can either be isolated in free form or, in the case of the presence of acidic or basic groups, converted to physiologically compatible salts (process b).

Acidic or basic products of the compound of the formula I may be in the form of their salts or in free form. Pharmacologically acceptable salts are preferred, for example alkali metal or alkaline earth metal salts or hydrochlorides, sulfates, hemisulfates, methylsulfonates, p-toluenesulfonates, all possible phosphates, and salts of amino acids, natural bases or carboxylic acids such as lactates, citrates, tartrates, acetates, adipates, fumarates, gluconates, glutamates, maleates or pamoates.

Physiologically tolerated salts are prepared from compounds of the formula I capable of salt formation, including their stereoisomeric forms, in process step b) in a manner known per se. If compounds of the formula I contain acidic functionality, stable alkali metal, alkaline earth metal or optionally substituted ammonium salts can be formed with basic reagents such as hydroxides, carbonates, bicarbonates, alkoxides, and ammonia or organic bases, for example trimethyl- or triethylamine, ethanolamine, diethanolamine or triethanolamine, trometamol or else basic amino acids, for instance lysine, ornithine or arginine. Basic groups of the compounds of the formula I form acid addition salts with acids. Suitable for this purpose are both inorganic and organic acids such as hydrochloric or hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid.

In process step c), the compound of the formula I, if it occurs as a mixture of diastereomers or enantiomers or results as mixtures thereof in the chosen synthesis, is separated into the pure stereoisomers either by chromatography on an optionally chiral support material or, if the racemic compound of the formula I is capable of salt formation, it is also possible to carry out a fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatographic methods on chiral stationary phases after appropriate derivatization known to the skilled worker. To separate enantiomers of the racemic carboxylic acids, the diastereomeric salts of differing solubility are formed with an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I which contain a basic group such an amino group, with optically active acids such as (+)-camphor-10-sulfonic acid, D- and L-tartaric acid, D- and L-lactic acid, and (+) and (−)-mandelic acid, into the pure enantiomers. It is also possible to convert chiral compounds containing alcohol or amine functions with appropriately activated or, where appropriate, N-protected enantiopure amino acids into the corresponding esters or amides, or conversely chiral carboxylic acids with carboxy-protected enantiopure amino acids into the amides or with enantiopure hydroxy carboxylic acids such as lactic acid into the corresponding chiral esters. The chirality of the amino acid or alcohol residue which has been introduced in enantiopure form can then be utilized to separate the isomers by carrying out a separation of the diastereomers which are now available by crystallization or chromatography on suitable stationary phases, and then eliminating the included chiral moiety again by suitable methods.

A further possibility with some of the inventive compounds is to prepare the framework structures using diastereomerically or enantiomerically pure starting materials. It is thus possible also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

The invention also relates to medicaments having an effective content of at least one compound of the formula I and/or a physiologically tolerated salt of the compound of the formula I and/or an optionally stereoisomeric form of the compound of the formula I, together with a pharmaceutically suitable and physiologically tolerated carrier, additive and/or other active ingredients and excipients.

Owing to the pharmacological properties, the compounds of the invention are suitable for example for the prophylaxis, secondary prevention and therapy of all disorders which can be treated by inhibition of the protease-activated receptor 1 (PAR1). Thus, the compounds of the invention are suitable both for a prophylactic and a therapeutic use on humans. They are suitable both for acute treatment and for long-term therapy. The compounds of the formula I can be employed in patients suffering from impairments of well being or diseases associated with thromboses, embolisms, hypercoagulability, fibrotic changes or inflammatory disorders. These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. The compounds of the formula I can further be employed in all procedures leading to contact of blood with foreign surfaces, such as for dialysis patients and patients with indwelling catheters. Compounds of the formula I can be employed in order to reduce the risk of thrombosis following surgical procedures such as knee and hip joint operations.

Compounds of the formula I are suitable for the treatment of patients with disseminated intravascular coagulation, sepsis and other intravascular events associated with inflammation. The compounds of the formula I are further suitable for the prophylaxis and treatment of patients with atherosclerosis, diabetes and the metabolic syndrome and the sequelae thereof. Impairments of the hemostatic system (for example fibrin deposits) have been implicated in mechanisms leading to tumor growth and tumor metastasis, and in inflammatory and degenerative articular disorders such as rheumatoid arthritis and arthrosis. Compounds of the formula I are suitable for retarding or preventing such processes.

Further indications for the use of the compounds of the formula I are fibrotic changes in the lung such as chronic obstructive pulmonary disease, adult respiratory distress syndrome (ARDS) and of the eye such as fibrin deposits following eye operations. Compounds of the formula I are also suitable for the prevention and/or treatment of scarring.

The medicaments of the invention can be administered by oral, inhalational, rectal or transdermal administration or by subcutaneous, intraarticular, intraperitoneal or intravenous injection. Oral administration is preferred. Coating of stents with compounds of the formula I and other surfaces which come into contact with blood in the body is possible. The invention also relates to a process for manufacturing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which customary aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably manufactured and administered in dosage units, where each unit comprises as active ingredient a particular dose of the compound of the invention of the formula I. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

Compounds of the formula I can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics. Suitable platelet aggregation inhibitors in this connection are cyclooxygenase 1 inhibitors such as aspirin, irreversible $P2Y_{12}$ antagonists such as clopidogrel or prasugrel, reversible $P2Y_{12}$ antagonists such as cangrelor or AZD6140 and thromboxane $A_2$/prostaglandin $H_2$ antagonists such as terutroban. It has been possible to show additive effects of PAR1 blockade in combination with $P2Y_{12}$ blockade for example (Eur. Heart J. 2007, 28, Abstract Supplement, 188).

EXAMPLES

End products were generally characterized by a chromatographic method with ultraviolet and mass spectrometry detection (LCUV/ESI-MS coupling), and $^1$H NMR. The compounds are described by reporting the corresponding retention time in the ion current (LC-MS rt) and the corresponding $[M+H]^+$ signal in the case of positive ionization in the corresponding mass spectrum. When no $[M+H]^+$ mass signal could be obtained, the $^1$H NMR data were reported as an alternative. Abbreviations used are either explained or correspond to the usual conventions. Silica gel separations were carried out manually (flash chromatography) or supported by semiautomatic cartridge systems such as Companion (CombiFlash) or Flashmaster II (Jones Chromatography). Unless stated otherwise, chromatographic separations were carried out on silica gel with ethyl acetate/heptane, dichloromethane/ethanol or dichloromethane/methanol mixtures as the eluent.

Solvents were evaporated generally under reduced pressure at from 35° C. to 45° C. on a rotary evaporator, which is referred to by phrases such as "concentrated", "concentrated by rotary evaporation", "dried", "freed of the solvent", "solvent removed or drawn off" or similar expressions.

LCUV/MS analyses carried out under the following conditions:

Method a (=met. a)

| | |
|---|---|
| System: | Agilent 1100 HPLC-System coupled to 1100 LC/MSD |
| Column: | YMC J'rshere ODS H80 20 × 2.1 mm, packing material 4 µm |
| Eluent: | ACN:H$_2$O + 0.05% TFA (flow rate 1 ml/min) |
| Gradient: | 4:96 (0 min) → 95:5 (2 min) → 95:5 (2.4 min) → 4:96 (2.45 min) |
| Ionization: | ESI$^+$ |

Method B (=met. b):

| | |
|---|---|
| System: | Agilent 1200 HPLC-System coupled to 6120 LC/MS |
| Column: | Luna C18, 10 × 2.0 mm, packing material 3 µm |
| Eluent: | ACN:H$_2$O + 0.05% TFA (flow rate 1.1 ml/min) |
| Gradient: | 7:93 (0 min) → 95:5 (1 min) → 95:5 (1.45 min) → 7:93 (1.5 min) |
| Ionization: | ESI$^+$ |

Method C (=met. c):

| | |
|---|---|
| System: | Agilent 1200 HPLC-System coupled to 6120 LC/MS |
| Column: | Luna C18, 10 × 2.0 mm, packing material 3 µm |
| Eluent: | ACN:H$_2$O + 0.05% TFA (flow rate 1.1 ml/min) |
| Gradient: | 1:99 (0 min) → 7:93 (0.3 min) → 95:5 (1.3 min) → 95:5 (1.75 min) → 1:99 (1.8 min) |
| Ionization: | ESI$^+$ |

Method D (=met. d):

| | |
|---|---|
| System: | Waters: 1525 pump, 996 PDA, LCT classic TOF-MS |
| Column: | Waters XBridge C18 4.6 × 50 mm; 2.5 µM |
| Eluent: | ACN + 0.05% TFA:H$_2$O TFA (flow rate 1.3 ml/min), 40° C. |
| Gradient: | 5:95 (0 min) → 5:95 (0.3 min) → 95:5 (3.5 min) → 95:5 (4 min) |
| Ionization: | ESI$^+$ |

Method E (=met. e):

| | |
|---|---|
| System: | Waters: 1525 pump, 996 PDA, LCT classic TOF-MS |
| Column: | Waters XBridge C18; 4.6 × 50 mm; 2.5 µM |
| Eluent: | ACN + 0.05% TFA:H$_2$O TFA (flow rate 1.7 ml/min), 40° C. |
| Gradient: | 5:95 (0 min) → 5:95 (0.2 min) → 95:5 (2.4 min) → 95:5 (3.2 min) → 5:95 (3.3 min) → 5:95 (4.0 min) |
| Ionization: | ESI$^+$ |

Method F (=met. f):

| | |
|---|---|
| System: | Waters: 1525 pump, 996 PDA, LCT classic TOF-MS |
| Column: | YMC J'shere, 33 × 2 mm, 4 µM |
| Eluent: | ACN + 0.05% TFA:H$_2$O + 0.05% TFA (flow rate 1.3 ml/min) |
| Gradient: | 5:95 (0 min) → 5:95 (2.5 min) → 95:5 (3 min) |
| Ionization: | ESI$^+$ |

Preparative HPLC with reversed-phase (RP) silica gel was carried out by the following methods:

Method A, standard method if no other method is mentioned in the text.

| | |
|---|---|
| Column: | Merck (Darmstadt, Deutschland) Purosphere ® RP18 25 × 250 mm, 10 µm |
| Eluent: | ACN:H$_2$O + 0.05% TFA (flow rate 25 ml/min) |
| Gradient: | 10:90 (0 min) → 90:10 (40 min) |

Method B

| | |
|---|---|
| Column: | Merck Purosphere ® RP18 25 × 250 mm, 10 µm |
| Eluent: | ACN:H$_2$O + 0.05% TFA (flow rate 25 ml/min) |
| Gradient: | 0:100 (0 min) → 0:100 (5 min) → 20:80 (20 min) |

Method C

| | |
|---|---|
| Column: | Agilent Prep-C18, 30 × 250 mm, 10 µm |
| Eluent: | ACN:H$_2$O + 0.05% TFA (flow rate 75 ml/min) |
| Gradient: | 10:90 (0 min) → 90:10 (12.5 min) → 90:10 (15 min) → 10:90(15.5 min) → 10:90 (17.5 min) |

The reactions took place in standard reaction apparatus such as single-neck or multineck flasks, which, unless stated otherwise, according to the need, had a capacity of from 5 ml to 2000 ml and, as required, were equipped with a septum, stopper, condenser, stirrer or other equipment. Unless mentioned otherwise, all reactions took place under argon as protective gas and were stirred with magnetic stirrers. Microwave reactions were carried out in the Emrys Optimizer from Personal Chemistry in vessels of capacity from 0.5 to 10 ml according to the need. Solvents such as dichloromethane, ethanol, dimethylformamide, methanol, isopropanol and the like were purchased as "dry" solvents and were also used thus in the reactions, without this being explicitly mentioned in each case.

ABBREVIATIONS USED

| abs. | absolute |
|---|---|
| ACN | acetonitrile |
| Boc | tert-butoxycarbonyl |
| Ex. | example |
| DCM | dichloromethane |
| DIPEA | N,N-diisopropylethylamine (Hunig's base) |
| DMF | dimethylformamide |
| DMSO | dimethyl sulfoxide |
| EA | ethyl acetate |
| eq. | equivalents |
| EtOH | ethanol |
| h | hour(s) |
| HPLC | high-performance liquid chromatography |
| Hünig's base | N,N-diisopropyl-N-ethylamine |
| LC-MS rt | retention time of the compound in the ion current of liquid chromatography |
| LCUV/MS | ultraviolet liquid chromatography/mass spectrometry |
| NMP | 1-methyl-2-pyrrolidone |
| MeOH | methanol |
| MtB ether | tert-butyl methyl ether |
| MW | microwave |
| RF | reflux |
| RT | room temperature (20° C. to 25° C.) |
| rt | retention time |
| TEA | triethylamine |
| TFA | trifluoroacetic acid |
| THF | tetrahydrofuran |
| TOTU | O-[(ethoxycarbonyl)cyanomethyleneamino]-N,N,N',N'-tetramethyluronium tetrafluoroborate |

Synthesis of the Units of the "Western Half"

W1.001

6-Ethoxy-[1,2,4]triazolo[4,3-b]pyridazin-3-ylamine

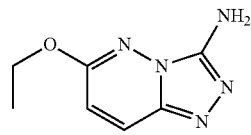

6-Chloro-[1,2,4]triazolo[4,3-b]pyridazin-3-ylamine (W2.001a, 616 mg) was dissolved in absolute ethanol (40 ml) and admixed with portions of solid sodium ethoxide (990 mg). After stirring at 55° C. for 2 h, water was added and the aqueous phase was extracted three times with dichloromethane. The combined extracts were dried over sodium sulfate, filtered and concentrated. 709 mg of crude product of the desired compound were obtained in sufficient purity.

LC-MS rt: 0.51 min [M+H]$^+$: 180.1 (met. a)

The following were synthesized analogously:

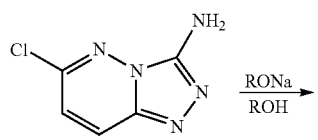

W2.001a

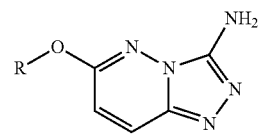

| Number | R | LC-MS rt | [M + H]$^+$ | Comment: |
|---|---|---|---|---|
| W1.002 | methyl- | 0.22 | 166.1 (met. a) | W2.001a (100 mg); sodium methoxide solution; product: 95 mg |
| W1.003 | | 0.69 | 194.1 (met. a) | W2.001a (100 mg); sodium isopropoxide solution; product: 84 mg |

W1.004

6-Cyclobutoxy-[1,2,4]triazolo[4,3-b]pyridazin-3-ylamine

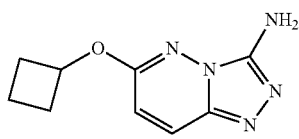

Cyclobutanol (2.43 ml) was initially charged at RT with stirring and cooled almost to 0° C. with an ice bath. Subsequently, the mixture was admixed with portions of sodium hydride (146 mg). The suspension formed was heated to 55° C. for 30 min and admixed with portions of 6-chloro-[1,2,4]triazolo[4,3-b]pyridazin-3-ylamine hydrobromide (W2.001, 200 mg), suspended in cyclobutanol (5 ml). After stirring at 55° C. for 1.5 h, the mixture was left to stand at RT overnight and then admixed with water and extracted three times with dichloromethane. The combined organic phases were dried over sodium sulfate and, after the desiccant had been filtered off, dried under reduced pressure. 136 mg of the title compound were obtained in solid form.

[LC-MS rt: 0.82 min [M+H]$^+$: 206.2 (met. a)

The following units were synthesized analogously:

W1.009

6-Cyclopropylmethoxy-[1,2,4]triazolo[4,3-b]pyridazin-3-ylamine

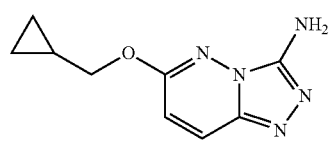

Cyclopropylmethanol (2.64 ml) was initially charged in DMF (35 ml), admixed under argon with sodium hydride (795 mg) and stirred at 40° C. for 1 h. Subsequently, 6-chloro-[1,2,4]triazolo[4,3-b]pyridazin-3-ylamine hydrobromide (W2.001; 1.66 g), dissolved in DMF (35 ml), were added dropwise. After 1 h, the mixture was admixed with water and extracted by shaking four times with dichloromethane. The combined organic phases were dried over magnesium sulfate and concentrated by rotary evaporation. The residue was triturated with MtB ether, filtered off with suction and dried. 720 mg of the title compound were obtained.

LC-MS rt: 0.80 min [M+H]$^+$: 206.1 (met. f)

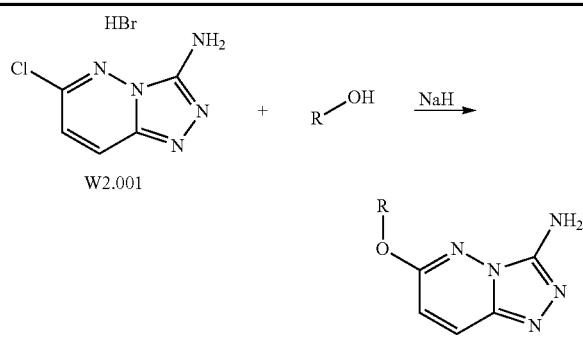

| Number | R | LC-MS rt | [M + H]$^+$ | Comment: |
|---|---|---|---|---|
| W1.005 | benzyl | 0.89 min | 242.1 (met. a) | W2.001a (100 mg) used dissolved in NMP; crude product purified by chromatography using silica gel with dichloromethane/methanol gradient; product: 48 mg |
| W1.006 | cyclohexylmethyl | 0.95 min | 234.1 (met. a) | W2.001 (200 mg); Crude product purified by preparative HPLC (met. A); product: 47 mg (TFA salt) |
| W1.007 | cyclopentylmethyl | 0.88 min | 220.1 (met. a) | W2.001 (463 mg); Crude product purified by preparative HPLC (met. A); product: 15 mg (TFA salt) |
| W1.008 | sec-butyl | 0.92 min | 222.1 (met. a) | W2.001a (194 mg) used suspended in a mixture of 10 ml of DMF and 5 ml of 3-pentanol; crude product purified by chromatography using silica gel with dichloromethane/methanol gradient; product: 155 mg |

The following units were synthesized analogously:

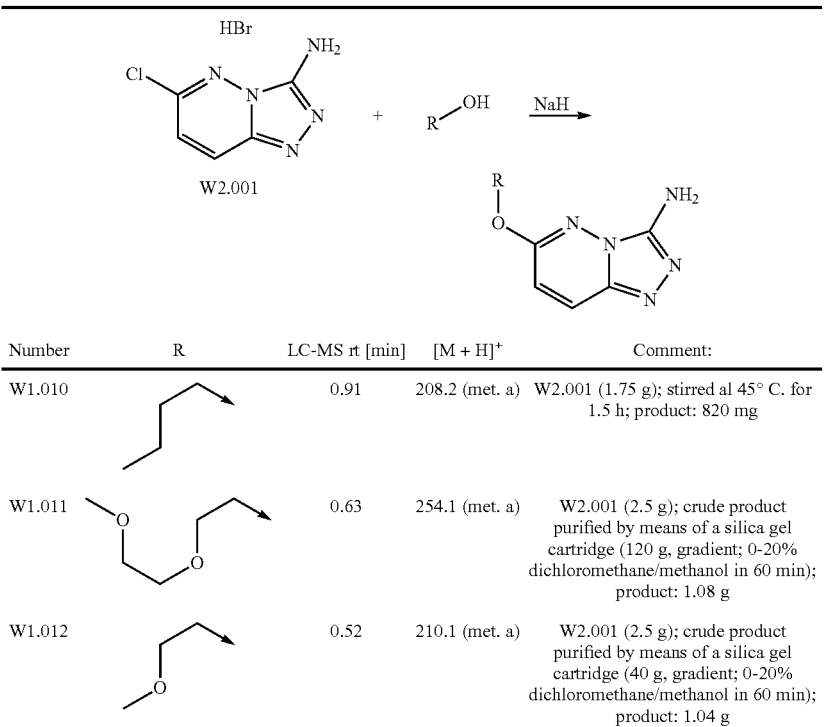

| Number | R | LC-MS rt [min] | [M + H]⁺ | Comment: |
|---|---|---|---|---|
| W1.010 | (propyl group) | 0.91 | 208.2 (met. a) | W2.001 (1.75 g); stirred al 45° C. for 1.5 h; product: 820 mg |
| W1.011 | (CH₂CH₂OCH₂CH₂OCH₂CH₃ group) | 0.63 | 254.1 (met. a) | W2.001 (2.5 g); crude product purified by means of a silica gel cartridge (120 g, gradient; 0-20% dichloromethane/methanol in 60 min); product: 1.08 g |
| W1.012 | (CH₂CH₂OCH₃ group) | 0.52 | 210.1 (met. a) | W2.001 (2.5 g); crude product purified by means of a silica gel cartridge (40 g, gradient; 0-20% dichloromethane/methanol in 60 min); product: 1.04 g |

W1.013

6-Phenoxy-[1,2,4]triazolo[4,3-b]pyridazin-3-ylamine

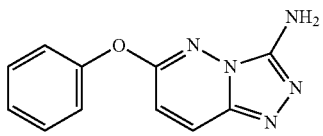

6-Chloro-[1,2,4]triazolo[4,3-b]pyridazin-3-ylamine hydrobromide (W2.001; 200 mg) were initially charged dissolved in NMP (4 ml). Thereafter, sodium phenoxide (185 mg) was introduced at RT. After stirring at RT for one hour, the reaction was completed by heating to 55° C. for 2 h. Subsequently, the mixture was admixed with water and extracted three times with dichloromethane. The combined organic phases were dried over sodium sulfate and, after the desiccant had been filtered off, dried under reduced pressure. The crude product was purified using silica gel with a dichloromethane/methanol gradient. 38 mg of the title compound were obtained in solid form. LC-MS rt: 0.80 min [M+H]⁺: 228.1 (met. a)

W1.014

6-(2,2,2-Trifluoroethoxy)-[1,2,4]triazolo[4,3-b]pyridazin-3-ylamine

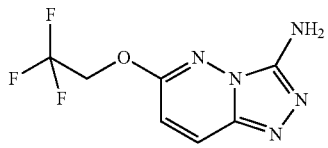

2,2,2-Trifluoroethanol (1 ml), sodium hydride (86 mg) and 6-chloro-[1,2,4]triazolo[4,3-b]pyridazin-3-ylamine hydrobromide (W2.001, 100 mg) were reacted according to W1.004. 87 mg of the title compound were obtained in solid form.

LC-MS rt: 0.68 min [M+H]⁺: 234.1 (met. a)

W1.020

6-Piperidin-1-yl-[1,2,4]triazolo[4,3-b]pyridazin-3-ylamine

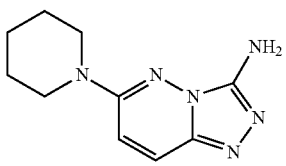

6-Chloro-[1,2,4]triazolo[4,3-b]pyridazin-3-ylamine hydrobromide (W2.001; 100 mg) were initially charged in water (1 ml) and admixed with piperidine (260 µl) with stirring. Thereafter, the mixture was heated to reflux for 1 h and, after cooling, freed of the solvent. Subsequently, the mixture was admixed with water and the solid formed was filtered off with suction and dried. The mother liquor was dried and admixed with a little water. The solid obtained was filtered off with suction and dried. The filtrate was then extracted three times with dichloromethane. The combined organic phases were dried over sodium sulfate and, after the desiccant had been filtered off, dried under reduced pressure. The three resulting solid fractions were combined and gave rise to 56 mg of the title compound.

LC-MS rt: 0.77 min [M+H]⁺: 219.1 (met. a)

The following was prepared analogously:

| Number | | LC-MS rt | [M + H]+ | Comment: |
|---|---|---|---|---|
| W1.021 | 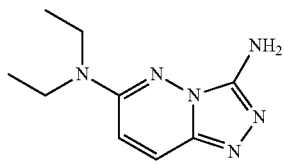 | 0.55 min | 221.1 (met. a) | W2.001 (150 mg); reflux for 5 h; dry crude product admixed with water and extracted directly with DCM. product: 81 mg |

W1.022

N*6*,N*6*-Diethyl-[1,2,4]triazolo[4,3-b]pyridazine-3,6-diamine

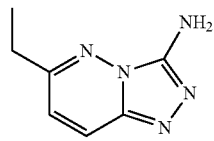

6-Chloro-[1,2,4]triazolo[4,3-b]pyridazin-3-ylamine hydrobromide (W2.001; 150 mg) was initially charged in water (5 ml) and admixed with diethylamine (814 μl) while stirring. Thereafter, the mixture was heated to reflux for 16 h and then further diethylamine (407 μl) was added. After refluxing for a further 12 h, the mixture was freed of the solvent, admixed with water and extracted three times with dichloromethane. The combined organic phases were dried over sodium sulfate and, after the desiccant had been filtered off, dried under reduced pressure. 67 mg of the title compound were obtained.

LC-MS rt: 0.72 min [M+H]+: 207.1 (met. a)

W1.025

6-Ethyl-[1,2,4]triazolo[4,3-b]pyridazin-3-ylamine (6-Ethylpyridazin-3-yl)hydrazine hydrochloride (2 g) was initially charged in a mixture of ethanol (30 ml) and water (6 ml) while stirring at RT. Thereafter, cyanogen bromide was cautiously added dropwise (2.4 g dissolved in 7.5 ml of ethanol and 1.5 ml of water). After stirring at RT for one hour, the mixture was left to stand overnight and, the next day, stirred for 4 further hours. The solvent was then drawn off and the residue was purified by means of preparative HPLC (met. C). The clean product fractions were combined, freed of the acetonitrile under reduced pressure, alkalized with saturated potassium carbonate solution and extracted repeatedly with dichloromethane. The combined organic phases were dried over sodium sulfate, filtered and concentrated. 830 mg of the title compound were obtained.

The aqueous potassium carbonate phase was likewise freeze-dried, then taken up with a little water and extracted five times with dichloromethane. The combined organic phases were dried over sodium sulfate, filtered and concentrated. A further 180 mg of the title compound were obtained.

LC-MS rt: 0.32 min [M+H]+: 164.1 (met. a)

W1.035

8-Methyl-6-(3-methyloxetan-3-ylmethoxy)-[1,2,4]triazolo[4,3-b]pyridazin-3-ylamine

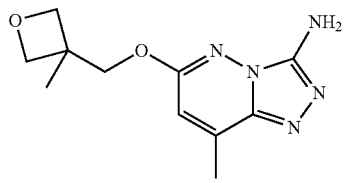

(3-Methyloxetan-3-yl)methanol (1.74 g) was initially charged in DMF (30 ml), admixed under argon with sodium hydride (408 mg) and stirred at 45° C. for 0.5 h. Subsequently, 6-chloro-8-methyl-[1,2,4]triazolo[4,3-b]pyridazin-3-ylamine hydrobromide (W2.002; 1.5 g) was dissolved in DMF (30 ml) and one equivalent of the alkoxide solution (10 ml) was added. After stirring at 45° C. for 30 min, a further 0.5 equivalent of alkoxide solution was added, followed by 0.5 eq. each after a further 30 and 60 min. Then the mixture was admixed with water, and the reaction mixture was dried and purified using silica gel (80 g cartridge, dichloromethane/methanol gradient of 0-20% in 60 min). 758 mg of the title compound were obtained. LC-MS rt: 0.49 min [M+H]+: 250.1 (met. b)

The following was prepared analogously:

| Number | | LC-MS rt | [M + H]⁺: | Comment: |
|---|---|---|---|---|
| W1.037 | 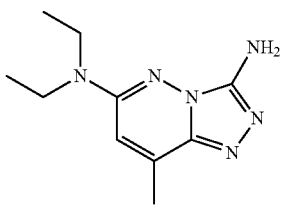 | 0.62 min | 222.1 (met. a) | W2.002 (1 g); product: 605 mg |

W1.040

N*6*,N*6*-Diethyl-8-methyl-[1,2,4]triazolo[4,3-b]pyridazine-3,6-diamine

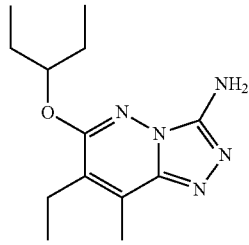

6-Chloro-8-methyl-[1,2,4]triazolo[4,3-b]pyridazin-3-ylamine hydrobromide (W2.002; 250 mg) was dissolved in abs. DMF (2 ml) and admixed with diethylamine (7 ml). Thereafter, the reaction mixture was placed into a heating block at 80° C. with stirring for 11 days. The solvent was then drawn off and the residue was admixed with a little water and extracted three times with dichloromethane. The combined organic phases were dried over sodium sulfate, filtered and concentrated. The residue was purified by means of preparative HPLC (met. A), and the clean product fractions were combined, freed of the acetonitrile under reduced pressure, alkalized with saturated potassium carbonate solution and extracted repeatedly with dichloromethane. The combined organic phases were dried over sodium sulfate, filtered and concentrated. 100 mg of the title compound were obtained.

LC-MS rt: 0.70 min [M+H]⁺: 221.2 (met. b)

W1.071

7-Ethyl-6-(1-ethylpropoxy)-8-methyl-[1,2,4]triazolo[4,3-b]pyridazin-3-ylamine

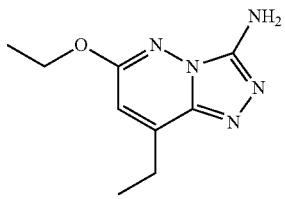

3-Pentanol (2.5 ml) was initially charged at RT with stirring. Thereafter, sodium hydride (91 mg) was added while cooling with ice. After stirring at 55° C. for 2.5 h, 6-chloro-7-ethyl-8-methyl-[1,2,4]triazolo[4,3-b]pyridazin-3-ylamine (W2.007; 120 mg), dissolved in 3-pentanol (2 ml) and DMF (4 ml), was added dropwise. After stirring for 1 h, the mixture was left to stand at RT overnight, and the reaction mixture was admixed with water and dichloromethane and then extracted three times with dichloromethane. The combined organic phases were dried over sodium sulfate and, after the desiccant had been filtered off, dried under reduced pressure. 126 mg of the title compound were obtained.

LC-MS rt: 0.90 min [M+H]⁺: 264.2 (met. b)

W1.075

6-Ethoxy-8-ethyl-[1,2,4]triazolo[4,3-b]pyridazin-3-ylamine

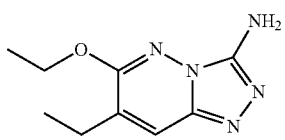

6-Chloro-8-ethyl-[1,2,4]triazolo[4,3-b]pyridazin-3-ylamine (W2.003; 700 mg) was dissolved in ethanol (100 ml) while stirring. Thereafter, the reaction mixture was admixed with sodium ethoxide (724 mg) and stirred at RT for 2 h. Subsequently, the mixture was heated to 45° C. for 3 h. After the solvent had been drawn off, the residue was admixed with water and extracted three times with dichloromethane. The combined organic phases were dried over sodium sulfate and, after the desiccant had been filtered off, dried under reduced pressure. 670 mg of the title compound were obtained.

LC-MS rt: 0.64 min [M+H]⁺: 208.2 (met. b)

W1.085

6-Ethoxy-7-ethyl-[1,2,4]triazolo[4,3-b]pyridazin-3-ylamine

6-Chloro-7-ethyl-[1,2,4]triazolo[4,3-b]pyridazin-3-ylamine trifluoroacetate salt (W2.011, 82 mg) was reacted

W1.100

N,N-Diethyl-3-amino-6-ethoxy-[1,2,4]triazolo[4,3-b]pyridazine-7-carboxamide

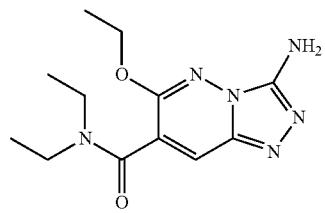

N,N-Diethyl-3-amino-6-chloro-[1,2,4]triazolo[4,3-b]pyridazine-7-carboxamide (W2.019, 50 mg) was initially charged in ethanol (5 ml) and admixed with sodium ethoxide (28 mg) while stirring. After stirring at RT for 7 h and leaving to stand overnight, the solvent was drawn off and the mixture was extracted three times with dichloromethane. The combined organic phases were dried over sodium sulfate and, after the desiccant had been filtered off, dried under reduced pressure. 51 mg of the title compound were obtained. LC-MS rt: 1.00 min [M+H]$^+$: 279.2 (met. b)

W1.101

N,N-Diethyl-3-amino-6-ethoxy-[1,2,4]triazolo[4,3-b]pyridazine-8-carboxamide

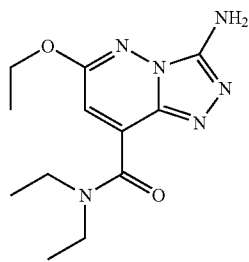

N,N-Diethyl-3-amino-6-chloro-[1,2,4]triazolo[4,3-b]pyridazine-8-carboxamide (W2.020, 50 mg) was prepared analogously to W1.100. 51 mg of the title compound were obtained. LC-MS rt: 1.04 min [M+H]$^+$: 279.2 (met. b)

W1.102

6-Ethoxy-N*7*,N*7*-diethyl-[1,2,4]triazolo[4,3-b]pyridazine-3,7-diamine

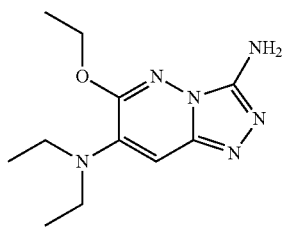

6-Chloro-N*7*,N*7*-diethyl-[1,2,4]triazolo[4,3-b]pyridazine-3,7-diamine (W2.021, 38 mg) were initially charged in ethanol (7 ml) and admixed with sodium ethoxide (24 mg). The reaction mixture stirred at RT for 4 h. It was then stirred at 45° C. for another 2 h. Subsequently, the mixture was dried, the residue was admixed with water and extracted three times with EA, and the combined EA phases were dried with magnesium sulfate, filtered and concentrated. 30 mg of the title compound were obtained as a crude product, which was clean enough for the next reaction.

LC-MS rt: 1.13 min [M+H]$^+$: 251.2 (met. a)

W1.107

6-(1-Ethylpropoxy)-8-isopropyl-[1,2,4]triazolo[4,3-b]pyridazin-3-ylamine

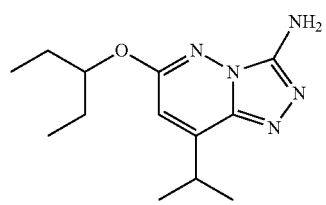

6-Chloro-8-isopropyl-[1,2,4]triazolo[4,3-b]pyridazin-3-ylamine (W2.009, 80 mg) was reacted and worked up analogously to W1.071. The crude product was then purified by means of preparative HPLC (met. A), and the clean product fractions were combined, freed of the acetonitrile under reduced pressure, alkalized with saturated potassium carbonate solution and extracted repeatedly with dichloromethane. The combined organic phases were dried over sodium sulfate, filtered and concentrated. 51 mg of the title compound were obtained.

LC-MS rt: 0.91 min [M+H]$^+$: 264.2 (met. b)

W1.112

7-Ethyl-6-(1-ethylpropoxy)-[1,2,4]triazolo[4,3-b]pyridazin-3-ylamine

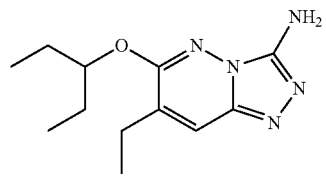

6-Chloro-7-ethyl-[1,2,4]triazolo[4,3-b]pyridazin-3-ylamine (W2.011, 150 mg) was reacted, worked up and purified analogously to W1.107. 103 mg of the title compound were obtained.

LC-MS rt: 0.87 min [M+H]$^+$: 250.2 (met. b)

W1.113

6-(1-Ethylpropoxy)-7-isopropyl-[1,2,4]triazolo[4,3-b]pyridazin-3-ylamine

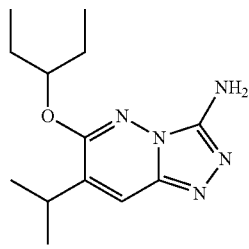

6-Chloro-7-isopropyl-[1,2,4]triazolo[4,3-b]pyridazin-3-ylamine (W2.013, 100 mg) was reacted and worked up analogously to W1.071. 132 mg of the title compound were obtained, which was still contaminated with a little DMF.
LC-MS rt: 0.90 min [M+H]$^+$: 264.2 (met. b)

W1.114

7-Cyclopropyl-6-(1-ethylpropoxy)-[1,2,4]triazolo[4,3-b]pyridazin-3-ylamine

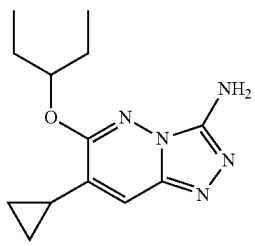

6-Chloro-7-cyclopropyl-[1,2,4]triazolo[4,3-b]pyridazin-3-ylamine (W2.012, 100 mg) was reacted and worked up analogously to W1.071. 116 mg of the title compound were obtained.
LC-MS rt: 0.87 min [M+H]$^+$: 262.2 (met. b)

W1.125

6,7-Diethoxy-[1,2,4]triazolo[4,3-b]pyridazin-3-ylamine

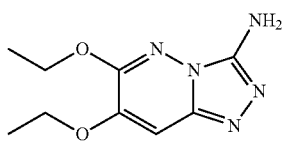

(5,6-Diethoxy-pyridazin-3-yl)hydrazine (W3.120; 50 mg) was initially charged in a mixture of ethanol (3.5 ml) and water (0.75 ml) at RT while stirring. Thereafter, cyanogen bromide (55 mg, dissolved in 0.75 ml of ethanol and 0.15 ml of water) was cautiously added dropwise. After stirring for 7 h, the mixture was left to stand overnight. Thereafter, a further 2 equivalents of cyanogen bromide, dissolved in 0.75 ml of ethanol and 0.15 ml of water, were added and the mixture was stirred further at RT for 2 h and then at 55° C. for 8 h. After cooling, the solvent was drawn off and the residue was admixed with water. After it had been alkalized with saturated potassium carbonate solution, it was extracted four times with dichloromethane. The combined organic phases were dried over sodium sulfate and, after the desiccant had been filtered off, dried under reduced pressure. The residue was purified by means of preparative HPLC (met. A). The clean product fractions were combined, freed of the acetonitrile under reduced pressure, alkalized with saturated potassium carbonate solution and extracted four times with dichloromethane. The combined organic phases were dried over sodium sulfate and, after the desiccant had been filtered off, dried under reduced pressure. 36 mg of the title compound were obtained.
LC-MS rt: 0.54 min [M+H]$^+$: 224.2 (met. b)

W1.130

6-Methanesulfonyl-7,8-dimethyl-[1,2,4]triazolo[4,3-b]pyridazin-3-ylamine

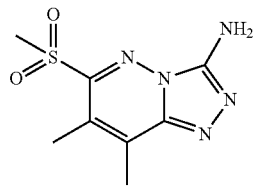

6-Chloro-7,8-dimethyl-[1,2,4]triazolo[4,3-b]pyridazin-3-ylamine hydrobromide (W2.006; 1.0 g) and sodium sulfinate (916 mg) were dissolved in DMF (6 ml) and stirred in a microwave at 150° C. for 45 min. After the solvent had been drawn off, the residue was purified using silica gel (40 g cartridge, dichloromethane/methanol gradient of 0-20% in 60 min). 1.02 g of the title compound were obtained.
LC-MS rt: 0.33 min [M+H]$^+$: 242.1 (met. b)

W1.135

3-Amino-7,8-dimethyl-[1,2,4]triazolo[4,3-b]pyridazine-6-carbonitrile

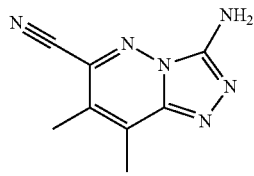

6-Methane sulfonyl-7,8-dimethyl-[1,2,4]triazolo[4,3-b]pyridazin-3-ylamine (W1.130; 1.0 g) was dissolved in DMF (30 ml) and admixed with potassium cyanide (405 mg). After stirring at 100° C. for 1 h, the mixture was dried. The residue was stirred in EA and chromatographed using a short silica gel column with EA. Fractions concentrated by rotary evaporation. 560 mg of the title compound were obtained.
LC-MS rt: 0.27 min [M+H]$^+$: 189.1 (met. b)

W1.140

3-Amino-7,8-dimethyl-[1,2,4]triazolo[4,3-b]pyridazine-6-carboxylic acid hydrochloride

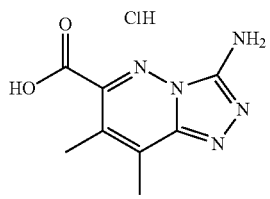

3-Amino-7,8-dimethyl-[1,2,4]triazolo[4,3-b]pyridazine-6-carbonitrile (W1.135; 600 mg) was admixed with concentrated hydrochloric acid (20 ml) and kept at reflux for 5 h. Subsequently, the hydrochloric acid was drawn off, and the residue was taken up with water and freeze-dried. 790 mg of the title compound were obtained, which was of sufficient purity for the next reaction.

LC-MS rt: 0.19 min [M+H]$^+$: 189.1 (met. c)

W1.145

Methyl 3-amino-7,8-dimethyl-[1,2,4]triazolo[4,3-b]pyridazine-6-carboxylate hydrochloride

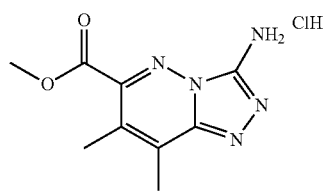

3-Amino-7,8-dimethyl-[1,2,4]triazolo[4,3-b]pyridazine-6-carboxylic acid hydrochloride (W1.140; 780 mg) was dissolved in methanol (40 ml) and thionyl chloride (1.9 ml) was slowly added dropwise, and then the mixture was stirred at 65° C. After 2.5 h, the mixture was dried and the residue was purified using silica gel (24 g cartridge, dichloromethane/methanol gradient of 0-20% in 60 min). 602 mg of the title compound were obtained.

LC-MS rt: 0.37 min [M+H]$^+$: 222.1 (met. b)

W1.165

(6-Ethoxy-7,8-dimethyl-[1,2,4]triazolo[4,3-b]pyridazin-3-yl)(2,2,2-trifluoroethyl)amine

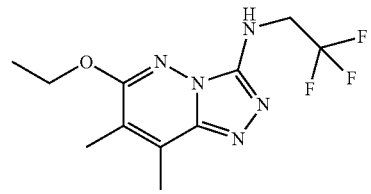

(6-Chloro-7,8-dimethyl-[1,2,4]triazolo[4,3-b]pyridazin-3-yl)(2,2,2-trifluoroethyl)amine (W2.150; 330 mg) was initially charged in ethanol (25 ml) and admixed with sodium ethoxide (90 mg). The reaction mixture was stirred at 50° C. for 4 h, then further sodium ethoxide (10 mg) was added and the mixture was stirred further at 50° C. for 3 h. After standing overnight, the mixture was admixed with water and dried. The residue was taken up in EA and washed three times with water. The EA phase was dried over sodium sulfate, filtered and concentrated. 340 mg of the title compound were obtained. LC-MS rt: 0.82 min [M+H]$^+$: 290.2 (met. b)

The following were prepared analogously:

| Number | | LC-MS rt | [M + H]$^+$ | Comment: |
|---|---|---|---|---|
| W1.166 | | 0.75 min | 248.2 (met. b) | W2.166; 690 mg; product: 508 mg |
| W1.168 | | 0.78 min | 250.2 (met. b) | W2.168; 78 mg; product: 57 mg |

-continued

| Number | | LC-MS rt | [M + H]⁺ | Comment: |
|---|---|---|---|---|
| W1.169 | (structure) | 0.71 min | 222.2 (met. b) | W2.169; 50 mg; product: 27 mg |
| W1.170 | (structure) | 0.49 min | 208.2 (met. b) | W2.170; 105 mg; product: 70 mg |

W1.175

[6-(1-Ethylpropoxy)-7,8-dimethyl-[1,2,4]triazolo[4,3-b]pyridazin-3-yl]methylamine

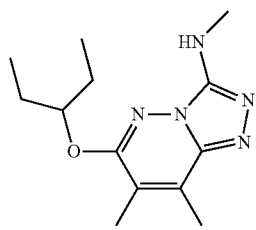

3-Pentanol (1.2 ml) was initially charged at RT with stirring. Thereafter, sodium hydride (77 mg) was added while cooling with ice. After stirring at 55° C. for 3 h, (6-chloro-7,8-dimethyl-[1,2,4]triazolo[4,3-b]pyridazin-3-yl)methylamine (W2.169; 50 mg), dissolved in 3-pentanol (1 ml) and DMF (2 ml), was added dropwise. After stirring for 2 h, the reaction mixture was left to stand at RT overnight, admixed with water and dichloromethane and then extracted three times more with dichloromethane. The combined organic phases were dried over magnesium sulfate and, after the desiccant had been filtered off, dried under reduced pressure. 44 mg of the title compound were obtained. LC-MS rt: 0.86 min [M+H]⁺: 264.2 (met. b)

The following was prepared analogously to W1.130:

| W1.190 | (structure) | 0.43 min | 256.0 (met. b) | W2.169 7.08 g; product: 4.84 g |
|---|---|---|---|---|

The following was prepared analogously to W1.135:

| W1.200 | (structure) | 0.39 min | 203.1 (met. b) | W1.190 4.83 g; product: 3.50 g |
|---|---|---|---|---|

The following was prepared analogously to W1.140:

| W1.210 | (structure) | 0.23 min | 222.1 (met. c) | W1.200 3.50 g; product: 5.27 g |
|---|---|---|---|---|

The following was prepared analogously to W1.145:

| Number | | LC-MS rt | [M + H]⁺: | Comment: |
|---|---|---|---|---|
| W1.219 | (structure) | 0.29 min | 222.1 (met. b) | W1.210 2.77 g; product: 2.56 g |

W1.250

N-Ethyl-7,8-dimethyl-3-methylamino-[1,2,4]triazolo[4,3-b]pyridazine-6-carboxamide

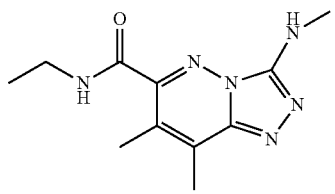

Methyl 7,8-dimethyl-3-methylamino-[1,2,4]triazolo[4,3-b]pyridazine-6-carboxylate hydrochloride (W1.220; 1.3 g) was dissolved in methanol (30 ml), cooled to 0° C., slowly admixed dropwise with ethylamine (11.44 ml; 2 M in THF) and stirred at 0° C. for 6 h. Then four further equivalents of ethylamine were added and the mixture was left to stand at RT over the weekend. Subsequently, the mixture was concentrated and purified using silica gel (40 g cartridge, dichloromethane/methanol gradient of 0-20% in 60 min). 1.12 g of the title compound were obtained. LC-MS rt: 0.81 min $[M+H]^+$: 249.1 (met. b)

The following was prepared analogously:

| Number | LC-MS rt | $[M + H]^+$ | Comment: |
|---|---|---|---|
| W1.251 | 0.14 min | 235.1 (met. b) | W1.219; 770 mg; dimethylamine (5 + 2 eq.; 2M in THF); product: 542 mg |

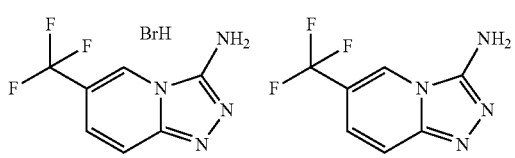

W1.300

[1,2,4]Triazolo[4,3-a]pyridin-3-ylamine hydrobromide

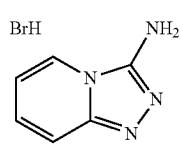

2-Hydrazinopyridine (654 mg) was dissolved in a mixture of EtOH and water (7.5/1.5 ml) at RT while stirring. Subsequently, cyanogen bromide solution (666 mg dissolved in a mixture of EtOH/water 1.5/0.3 ml) was added dropwise while stirring. After stirring at RT for 6 h, the solvent was drawn off, and the residue was taken up in water and freeze-dried. 1.3 g of the title compound were obtained. LC-MS rt: 0.15 min $[M+H]^+$: 135.3 (met. a)

W1.301

6-Trifluoromethyl-[1,2,4]triazolo[4,3-a]pyridin-3-ylamine hydrobromide and 6-trifluormethyl-[1,2,4]triazolo[4,3-a]pyridin-3-ylamine 5-(Trifluoromethyl)pyrid-2-ylhydrazine (500 mg) was dissolved at RT in a mixture of EtOH/water (7.5/1.5 ml) while stirring. Thereafter, cyanogen bromide solution (314 mg dissolved in EtOH/water 0.75/0.15 ml) was slowly and cautiously added dropwise within 30 min. After stirring at RT for 3 h, the precipitate was filtered off with suction and dried under high vacuum (oil pump). 329 mg of 6-trifluoromethyl-[1,2,4]triazolo[4,3-a]pyridin-3-ylamine hydrobromide were obtained.

The mother liquor was dried and the residue was purified by means of preparative HPLC. The clean, product-containing fractions were combined and freed of the ACN, and the aqueous residue was alkalized with saturated sodium hydrogencarbonate solution. Then the residue was extracted three times with EA and the combined EA phases were dried over magnesium sulfate, filtered and concentrated. 110 mg of trifluoromethyl-[1,2,4]triazolo[4,3-a]pyridin-3-ylamine were obtained.

LC-MS rt 0.54 min $[M+H]^+$: 203.1 (met. a)

W2

W2.001

6-Chloro-[1,2,4]triazolo[4,3-b]pyridazin-3-ylamine hydrobromide

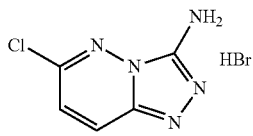

3-(Chlorpyridazin-6-yl)hydrazine (5 g) was dissolved in a mixture of EtOH (90 ml) and water (36 ml) at RT while stirring. Thereafter, 5 M cyanogen bromide solution (13 ml in acetonitrile) was cautiously added dropwise. After stirring for 4.5 h, the mixture was left to stand overnight and, the next day, further 5 M cyanogen bromide solution (3 ml in acetonitrile) was added while stirring. After a further 4 h of stirring, the precipitate formed was filtered off with suction and dried. 6.1 g of the title compound were obtained.

The mother liquor was admixed with MtB ether and the precipitate formed was filtered off with suction and dried, so as to obtain a further 1.5 g of the title compound.

LC-MS rt: 0.24 min [M+H]$^+$: 170.1 (met. a)

W2.001a

6-Chloro-[1,2,4]triazolo[4,3-b]pyridazin-3-ylamine

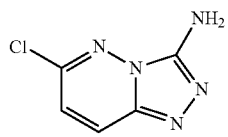

6-Chloro-[1,2,4]triazolo[4,3-b]pyridazin-3-ylamine hydrobromide (W2.001; 1.1 g) was taken up with a large amount of water and alkalized with saturated potassium carbonate solution. The solid which precipitated out was filtered off with suction and dried (388 mg). Repeated extraction of the mother liquor with dichloromethane, drying of the combined organic phases over sodium sulfate, filtration and concentration afforded a further 228 mg of product in total.

LC-MS rt: 0.24 min [M+H]$^+$: 170.1 (met. a)

W2.002

6-Chloro-8-methyl-[1,2,4]triazolo[4,3-b]pyridazin-3-ylamine hydrobromide

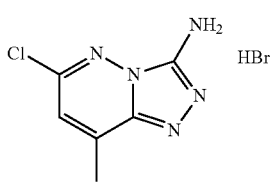

(6-Chloro-4-methylpyridazin-3-yl)hydrazine (W3.002; 4.6 g) were initially charged in EtOH (330 ml) and water (70 ml) while stirring at RT. Thereafter, cyanogen bromide in a mixture of EtOH (170 ml) and water (30 ml) was slowly added dropwise at RT. After stirring at RT for 6 h, the mixture was left to stand overnight. Then the mixture was dried and the residue was purified using silica gel (40 g cartridge, DCM/methanol gradient of 0-10% in 30 min). 7.3 g of the title compound were obtained.

LC-MS rt: 0.17 min [M+H]$^+$: 184.1 (met. b)

W2.002b

6-Chloro-8-methyl-[1,2,4]triazolo[4,3-b]pyridazin-3-ylamine trifluoroacetic acid salt

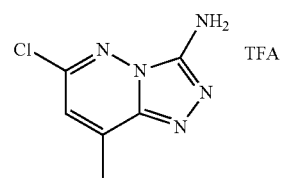

(6-Chloro-4-methylpyridazin-3-yl)hydrazine (W3.002; 432 mg) was initially charged in a mixture of ethanol (15 ml) and water (3 ml) while stirring at RT. Thereafter, cyanogen bromide (581 mg, dissolved in 7 ml of EtOH and 1.5 ml of water) was cautiously added dropwise. After stirring for 2 h, the mixture was left to stand overnight. Thereafter, the mixture was stirred at RT for a further 4 h and then at 50° C. for 2 h. After cooling overnight, the solvent was drawn off and the residue was purified by means of preparative HPLC (met. A). The clean product fractions were combined, freed of the acetonitrile under reduced pressure and freeze-dried. 158 mg of the title compound were obtained.

LC-MS rt: 0.44 min [M+H]$^+$: 184.1 (met. a)

W2.007

6-Chloro-7-ethyl-8-methyl-[1,2,4]triazolo[4,3-b]pyridazin-3-ylamine

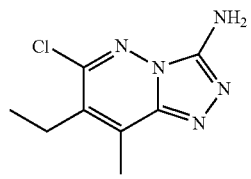

(6-Chloro-5-ethyl-4-methylpyridazin-3-yl)hydrazine (W3.007; 340 mg) was dissolved in ethanol/water (10/2 ml) at RT while stirring. Thereafter, cyanogen bromide (386 mg, dissolved in 5 ml of ethanol and 1 ml of water) was cautiously added dropwise. After stirring at RT for 5 h, the mixture was left to stand overnight and then the solvent was drawn off, and the residue was admixed with water. Once the residue had been alkalized with saturated potassium carbonate solution, it was extracted three times with dichloromethane. The combined organic phases were dried over sodium sulfate and, after filtering off the desiccant, dried under reduced pressure. 385 mg of the title compound were obtained. LC-MS rt: 0.62 min [M+H]$^+$: 212.1 (met. b)

W2.008

6-Chloro-8-ethyl-7-methyl-[1,2,4]triazolo[4,3-b]pyridazin-3-ylamine

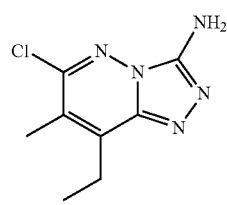

(6-Chloro-4-ethyl-5-methylpyridazin-3-yl)hydrazine trifluoroacetic acid salt (W3.008; 340 mg) was initially charged in a mixture of EtOH (12 ml) and water (2 ml) at RT while stirring. Thereafter, cyanogen bromide (240 mg), dissolved in 3 ml of EtOH and 1 ml of water, was cautiously added dropwise and the mixture was stirred for 8 h. After standing overnight, 0.5 eq. cyanogen bromide solution was added and the mixture was stirred again at RT for 4.5 h and then at 55° C. for 2 h. After standing overnight, the solvent was drawn off and the residue was admixed with water. Once it had been alkalized with saturated potassium carbonate solution, the mixture was extracted three times with dichloromethane. The combined organic phases were dried over sodium sulfate and, after the desiccant had been filtered off, dried under reduced pressure. 270 mg of the title compound were obtained.
LC-MS rt: 0.54 min [M+H]$^+$: 212.1 (met. b)

W2.009

6-Chloro-8-isopropyl-[1,2,4]triazolo[4,3-b]pyridazin-3-ylamine

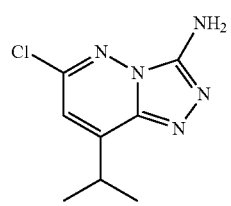

(6-Chloro-4-isopropylpyridazin-3-yl)hydrazine trifluoroacetic acid salt (W3.009; 258 mg) was initially charged in ethanol/water (6/1 ml) at RT while stirring. Thereafter, cyanogen bromide (182 mg, dissolved in a mixture of 1.5 ml of EtOH and 0.5 ml of water) was cautiously added dropwise. After stirring for 5 hours, the mixture was left to stand overnight, another 1 eq. of the cyanogen bromide solution was added and the mixture was stirred all day. After standing overnight, the solvent was drawn off and the residue was admixed with water. Once the residue had been alkalized with saturated potassium carbonate solution, it was extracted three times with dichloromethane. The combined organic phases were dried over sodium sulfate and, after filtering off the desiccant, dried under reduced pressure. 180 mg of the title compound were obtained in sufficient purity. LC-MS rt: 0.65 min [M+H]$^+$: 212.1 (met. b)
$^1$H NMR (500 MHz, DMSO-d6) [ppm]: 6.98 (1H), 6.63 (2H), 3.37 (1H), 1.35 (6H)

W2.011

6-Chloro-7-ethyl-[1,2,4]triazolo[4,3-b]pyridazin-3-ylamine

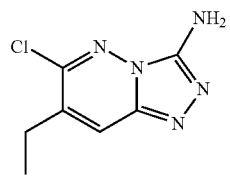

(6-Chloro-5-ethylpyridazin-3-yl)hydrazine trifluoroacetic acid salt (W3.011; 169 mg) was converted and worked up analogously to W2.009. 130 mg of the title compound were obtained in sufficient purity.
LC-MS rt: 0.33 min [M+H]$^+$: 198.1 (met. b)

W2.012

6-Chloro-7-cyclopropyl-[1,2,4]triazolo[4,3-b]pyridazin-3-ylamine

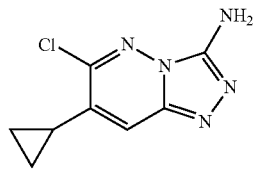

(6-Chloro-5-cyclopropylpyridazin-3-yl)hydrazine trifluoroacetic acid salt (W3.012; 400 mg) was converted and worked up analogously to W2.008, except that, instead of 0.5, one further equivalent of cyanogen bromide solution was added. 260 mg of the title compound were obtained in sufficient purity.
LC-MS rt: 0.45 min [M+H]$^+$: 210.1 (met. b)

W2.013

6-Chloro-7-isopropyl-[1,2,4]triazolo[4,3-b]pyridazin-3-ylamine

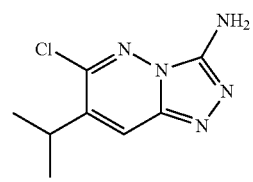

(6-Chloro-5-isopropylpyridazin-3-yl)hydrazine trifluoroacetic acid salt (W3.013; 400 mg) was initially charged in ethanol/water (6/1 ml) at RT while stirring. Thereafter, cyanogen bromide (353 mg, dissolved in a mixture of 1 ml of EtOH and 0.5 ml of water) was cautiously added dropwise. After stirring for 5 hours, the mixture was left to stand overnight and stirred for a further day. After standing overnight, the solvent was drawn off and the residue was admixed with water. Once the residue had been alkalized with saturated potassium carbonate solution, it was extracted three times with dichloromethane. The combined organic phases were dried over sodium sulfate and, after filtering off the desiccant, dried under reduced pressure. 400 mg of the title compound were obtained in sufficient purity.

LC-MS rt: 0.65 min [M+H]$^+$: 212.1 (met. b)

$^1$H NMR (500 MHz, DMSO-d6) [ppm]: 7.97 (1H), 6.61 (2H), 3.11 (1H), 1.25 (6H)

W2.019

N,N-Diethyl-3-amino-6-chloro-[1,2,4]triazolo[4,3-b]pyridazine-7-carboxamide

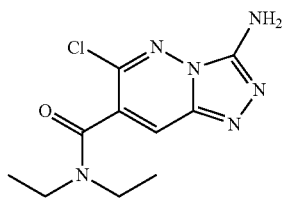

N,N-Diethyl-3-chloro-6-hydrazinopyridazine-4-carboxamide trifluoroacetic acid salt (W3.019; 390 mg) was converted and worked up analogously to W2.007. 285 mg of the title compound were obtained in sufficient purity.

LC-MS rt: 0.94 min [M+H]$^+$: 269.1 (met. a)

W2.020

N,N-Diethyl-3-amino-6-chloro-[1,2,4]triazolo[4,3-b]pyridazine-8-carboxamide

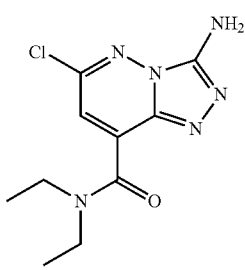

N,N-Diethyl-6-chloro-3-hydrazinopyridazine-4-carboxamide trifluoroacetic acid salt (W3.020; 320 mg) was converted and worked up analogously to W2.007. 222 mg of the title compound were obtained in sufficient purity.

LC-MS rt: 0.93 min [M+H]$^+$: 269.1 (met. a)

W2.021

6-Chloro-N*7*,N*7*-diethyl-[1,2,4]triazolo[4,3-b]pyridazine-3,7-diamine

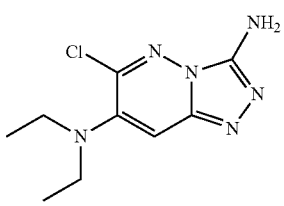

(3-Chloro-6-hydrazinopyridazin-4-yl)diethylamine (W3.021; 215 mg) was converted analogously to W2.007, and the solvent mixture was drawn off. The residue was purified by means of preparative HPLC (met. A). The product fractions, each of them clean, were combined, freed of the acetonitrile under reduced pressure, adjusted to pH 9 with sodium hydrogencarbonate and extracted five times with DCM. The combined organic phases were dried over magnesium sulfate and, after filtering off the desiccant, dried under reduced pressure. 94 mg of the title compound were obtained in sufficient purity.

LC-MS rt: 1.04 min [M+H]$^+$: 241.1 (met. a)

W2.150

(6-Chloro-7,8-dimethyl-[1,2,4]triazolo[4,3-b]pyridazin-3-yl)-(2,2,2-trifluoroethyl)amine

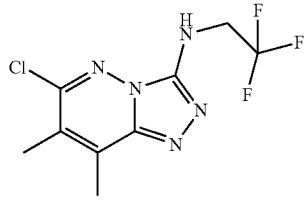

N*-(6-Chloro-4,5-dimethylpyridazin-3-yl)amino-N-(2,2,2-trifluoroethyl)urea (W3.150; 400 mg) was dissolved in phosphorus oxychloride (10 ml) and heated to 80° C. while stirring. After stirring at 80° C. for 7 h, the mixture was left to stand overnight and then the phosphorus oxychloride was drawn off. The residue was dissolved in water/DCM and adjusted to pH 9 with sodium hydrogencarbonate, and the phases were separated. The aqueous phase was extracted three times with DCM, and the combined extracts were washed with saturated sodium chloride solution, dried over sodium carbonate, filtered and concentrated. 330 mg of the title compound were obtained.

LC-MS rt: 0.83 min [M+H]$^+$: 280.1 (met. b)

The following were prepared analogously to W2.169:

| Number | | LC-MS rt | [M + H]+ | Comment: |
|---|---|---|---|---|
| W2.166 | 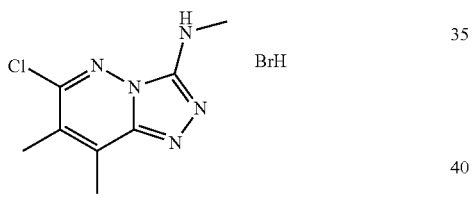 | 0.64 min | 238.1 (met. b) | W3.166 830 mg; purification by means of HPLC (met. D); product: 690 mg |
| W2.168 | | 0.68 min | 226.1 (met. b) | W3.168 140 mg; purification by means of HPLC (met. D); product: 82 mg |

W2.169

(6-Chloro-7,8-dimethyl-[1,2,4]triazolo[4,3-b]pyridazin-3-yl)methylamine hydrobromide

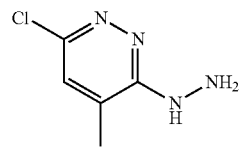

N'-(6-Chloro-4,5-dimethylpyridazin-3-yl)amino-N-methylthiourea (W3.169; 11.25 g) was dissolved in ethanol (400 ml), admixed with ethyl bromoacetate (5.57 ml) and kept under reflux with exclusion of moisture. After 2 h, the solvent was drawn off and the residue was purified using silica gel (120 g cartridge, DCM/methanol gradient of 0-10% in 60 min). 10.9 g of the title compound were obtained. LC-MS rt: 0.35 min [M+H]+: 212.1 (met. b)

The following was prepared analogously to W2.169:

| Number | | LC-MS rt | [M + H]+: | Comment: |
|---|---|---|---|---|
| W2.170 | 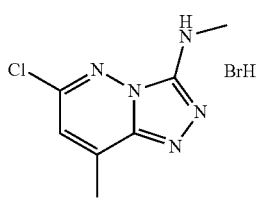 | 0.24 min | 198.1 (met. b) | W3.170 7.74 g; product: 7.93 g |

W3

W3.002

(6-Chloro-4-methylpyridazin-3-yl)hydrazine

Synthesized analogously to U.S. Pat. No. 4,578,464
LC-MS rt: 0.21 min [M+H]+: 159.1 (met. a)

W3.003 and W3.011

(6-Chloro-4-ethylpyridazin-3-yl)hydrazine trifluoroacetate and (6-chloro-5-ethylpyridazin-3-yl)hydrazine trifluoroacetate

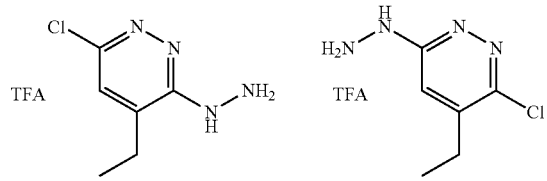

3,6-Dichloro-4-ethylpyridazine (W4.003, 2×2.4 g) was divided between 2 microwave vessels and each was admixed with a mixture of hydrazine monohydrate (6 ml) and dioxane (7 ml). The reaction mixture was kept in the microwave at 130° C. for 1 h. Subsequently, the contents of the two vessels were combined in a round-bottom flask and dried. The residue was admixed with water and extracted three times with dichloromethane. The combined organic phases were dried over sodium sulfate and, after the desiccant had been filtered off, dried under reduced pressure. The workup process was repeated twice more. The residue thus obtained was separated by means of preparative HPLC (method A, except gradient of 100% water+0.05% TFA→15% acetonitrile/85% water+0.05% TFA in 25 min). The product fractions, each of them clean, were combined, freed of the acetonitrile under reduced pressure and freeze-dried. 1.35 g of (6-chloro-4-ethylpyridazin-3-yl)hydrazine as the trifluoroacetate and 3.96 g of (6-chloro-5-ethylpyridazin-3-yl)hydrazine as the trifluoroacetate were obtained.

(6-Chloro-4-ethylpyridazin-3-yl)hydrazine as the trifluoroacetate, W3.003

LC-MS rt: 0.20 min [M+H]$^+$: 173.1 (met. c)

(6-Chloro-5-ethylpyridazin-3-yl)hydrazine as the trifluoroacetate, W3.011

LC-MS rt: 0.13 min [M+H]$^+$: 173.1 (met. b)

W3.005

(6-Chloro-5-methylpyridazin-3-yl)hydrazine

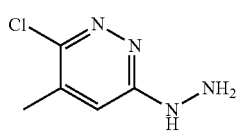

Synthesized analogously to U.S. Pat. No. 4,578,464 LC-MS rt: 0.26 min [M+H]$^+$: 159.1 (met. a)

W3.006

(6-Chloro-4,5-dimethylpyridazin-3-yl)hydrazine

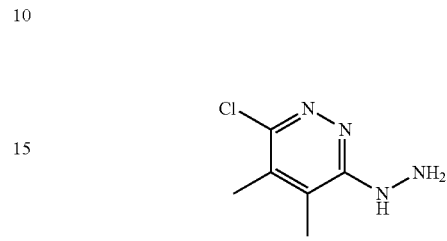

3,6-Dichloro-4,5-dimethylpyridazine (W4.006; 29.0 g) was admixed with 160 ml of hydrazine monohydrate solution (160 ml) and heated to 90° C. while stirring for 4 h. The reaction mixture was admixed with water and the precipitate was filtered off with suction, washed with water and dried over phosphorus pentoxide. 27.2 g of the title compound were obtained.

LC-MS rt: 0.15 min [M+H]$^+$: 173.1 (met. b)

W3.007 and W3.008

(6-Chloro-5-ethyl-4-methylpyridazin-3-yl)hydrazine (also as the TFA salt) and (6-chloro-4-ethyl-5-methylpyridazin-3-yl)hydrazine trifluoroacetic acid salt

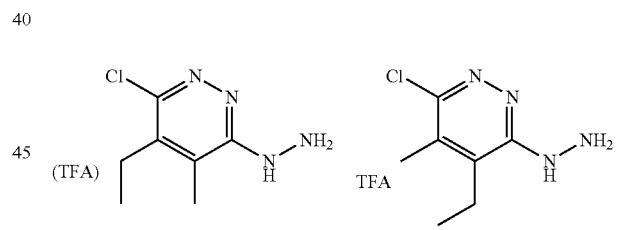

3,6-Dichloro-4-ethyl-5-methylpyridazine (W4.007; 1 g) was initially charged in dioxane (8 ml) with addition of hydrazine monohydrate (2 ml) in a microwave vessel at RT. Thereafter, the reaction mixture was kept at 140° C. in the microwave for 1 h. In the course of standing overnight, a solid precipitated out, which was filtered off with suction, washed and dried. 345 mg of (6-chloro-5-ethyl-4-methylpyridazin-3-yl)hydrazine were obtained as the free base.

The mother liquor was concentrated to dryness and the residue was purified by means of preparative HPLC (met. F). The product fractions, each of them clean, were combined, freed of the acetonitrile under reduced pressure and freeze-dried. 340 mg of 6-chloro-4-ethyl-5-methylpyridazin-3-yl)hydrazine trifluoroacetic acid salt and 239 mg of (6-chloro-5-ethyl-4-methylpyridazin-3-yl)hydrazine as the trifluoroacetate were obtained.

(6-Chloro-5-ethyl-4-methylpyridazin-3-yl)hydrazine trifluoroacetic acid salt, W3.007

LC-MS rt: 0.25 min [M+H]+: 187.1 (met. b)

(6-Chloro-4-ethyl-5-methylpyridazin-3-yl)hydrazine trifluoroacetic acid salt, W3.008

LC-MS rt: 0.22 min [M+H]+: 187.1 (met. b)

W3.009 and W3.013

(6-Chloro-4-isopropylpyridazin-3-yl)hydrazine trifluoroacetic acid salt and (6-chloro-5-isopropylpyridazin-3-yl)hydrazine trifluoroacetic acid salt

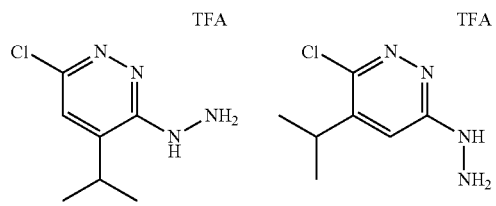

3,6-Dichloro-4-isopropylpyridazine (W4.009; 2.3 g) was converted analogously to W3.007 and then dried. After preparative chromatography (met. F), 260 mg of (6-chloro-4-isopropylpyridazin-3-yl)hydrazine trifluoroacetic acid salt and 2.16 g of (6-chloro-5-isopropylpyridazin-3-yl)hydrazine trifluoroacetic acid salt were obtained.

(6-Chloro-4-isopropylpyridazin-3-yl)hydrazine trifluoroacetic acid salt, W3.009

LC-MS rt: 0.20 min [M+H]+: 187.1 (met. b)

(6-Chloro-5-isopropylpyridazin-3-yl)hydrazine trifluoroacetic acid salt, W3.012

LC-MS rt: 0.34 min [M+H]+: 187.1 (met. b)

W3.010 and W3.012

(6-Chloro-4-cyclopropylpyridazin-3-yl)hydrazine trifluoroacetic acid salt and (6-chloro-5-cyclopropylpyridazin-3-yl)hydrazine trifluoroacetic acid salt

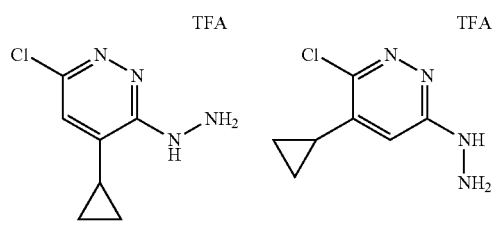

3,6-Dichloro-4-cyclopropylpyridazine (W4.010; 1.4 g) was converted analogously to W3.007 and then dried. After preparative chromatography (met. F), 805 mg of (6-chloro-4-cyclopropylpyridazin-3-yl)hydrazine trifluoroacetic acid salt and 708 mg of (6-chloro-5-cyclopropylpyridazin-3-yl)hydrazine were obtained.

(6-Chloro-4-cyclopropylpyridazin-3-yl)hydrazine trifluoroacetic acid salt, W3.010

LC-MS rt: 0.15 min [M+H]+: 185.1 (met. b)

(6-Chloro-5-cyclopropylpyridazin-3-yl)hydrazine trifluoroacetic acid salt, W3.012

LC-MS rt: 0.22 min [M+H]+: 185.1 (met. b)

W3.019 and W3.020

N,N-Diethyl-3-chloro-6-hydrazinopyridazine-4-carboxamide trifluoroacetic acid salt and N,N-diethyl-6-chloro-3-hydrazinopyridazin-4-carboxamide trifluoroacetic acid salt

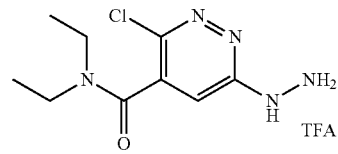

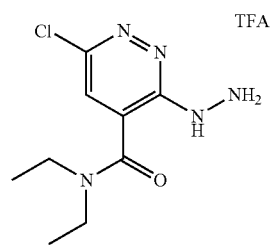

N,N-Diethyl-3,6-dichloropyridazine-4-carboxamide (W4.019; 18 g) was suspended in water (60 ml) and admixed with hydrazine monohydrate (2.8 ml). After stirring at 60° C. for 1 h, the mixture was heated to 100° C. for 2 h. After cooling to RT, the mixture was admixed with DCM and extracted four times with DCM. The combined extracts were dried over sodium sulfate, filtered and concentrated. The residue was purified by means of preparative HPLC (met. C). The clean, product-containing fractions were each combined, freed of ACN and freeze-dried. 910 mg of N,N-diethyl-3-chloro-6-hydrazinopyridazine-4-carboxamide trifluoroacetic acid salt and 560 mg of N,N-diethyl-6-chloro-3-hydrazinopyridazine-4-carboxamide trifluoroacetic acid salt were obtained.

N,N-Diethyl-3-chloro-6-hydrazinopyridazine-4-carboxamide trifluoroacetic acid salt LC-MS rt: 0.79 min [M+H]$^+$: 244.1 (met. a)

6-Chloro-3-hydrazinopyridazine-4-carboxamide trifluoroacetic acid salt

LC-MS rt: 0.68 min [M+H]$^+$: 244.1 (met. a)

W3.021

(3-Chloro-6-hydrazinopyridazin-4-yl)diethylamine trifluoroacetic acid salt

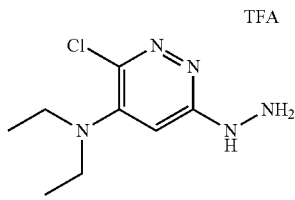

(3,6-Dichloropyridazin-4-yl)diethylamine (W4.021; 500 mg) was initially charged in dioxane (20 ml) while stirring, and admixed with hydrazine hydrate (0.65 ml). Thereafter, the mixture was heated first at 80° C. for 2 h and then to reflux for 3 h. After being left to stand over the weekend, the mixture was heated to reflux for a further 48 h and, after cooling, the solvent was drawn off. The residue was purified by means of preparative HPLC (met. A). The clean, product-containing fractions were each combined, freed of the ACN, basified with saturated sodium hydrogencarbonate solution and then extracted five times with EA and five times with DCM. The combined organic phases were dried over magnesium sulfate, filtered and concentrated. 118 mg of reactant and 220 mg of the title compound were isolated.

LC-MS rt: 1.24 min [M+H]$^+$: 220.1 (met. a)

W3.120

(5,6-Diethoxypyridazin-3-yl)hydrazine

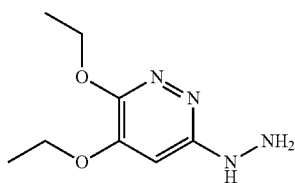

N-(5,6-Diethoxypyridazin-3-yl)-N-nitroamine (W4.120; 114 mg) was dissolved in acetic acid (5 ml) and added dropwise while cooling with ice and stirring at between 10 and 20° C. to a mixture of zinc (130 mg) in water (3 ml). Thereafter, the ice bath was removed and the mixture was stirred at RT for 1 h. Then the mixture was alkalized with 10 N sodium hydroxide solution, the aqueous phase was extracted three times with DCM, and the combined DCM phases were dried over sodium sulfate, filtered and concentrated. The residue was purified by means of preparative HPLC (met. A). The clean, product-containing fractions were each combined, freed of the ACN, basified with saturated potassium carbonate solution and then extracted three times with DCM. The combined organic phases were dried over sodium sulfate, filtered and concentrated. 50 mg of the title compound were obtained.

LC-MS rt: 0.37 min [M+H]$^+$: 199.2 (met. b)

W3.150

N*-(6-Chloro-4,5-dimethylpyridazin-3-yl)amino-N-(2,2,2-trifluoroethyl)urea and N*-(6-chloro-4,5-dimethylpyridazin-3-yl)amino-N-(2,2,2-trifluorethyl)urea hydrochloride

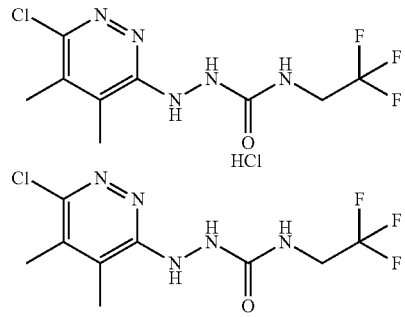

4-Nitrophenyl chloroformate (750 mg) was dissolved in THF (55 ml), 2,2,2-trifluoroethylamine (0.3 ml) was added while stirring and the mixture was stirred at RT for 3 h. Then (6-chloro-4,5-dimethylpyridazin-3-yl)hydrazine (W3.006, 620 mg) was added dissolved in THF (100 ml), followed by triethylamine (0.7 ml), and stirred at RT for 3 h. After being left to stand overnight, the precipitated solid was filtered off with suction and dried. 840 mg of the free base were obtained, which still contained significant amounts of triethylamine hydrochloride.

The mother liquor was dried and purified by means of preparative HPLC (met. D). The clean, product-containing fractions were combined and dried. A further 400 mg of the title compound were obtained as the hydrochloride. LC-MS rt: 0.40 min [M+H]$^+$: 298.1 (met. b)

W3.166

N*-(6-Chloro-4,5-dimethylpyridazin-3-yl)amino-N-(cyclopropyl)thiourea

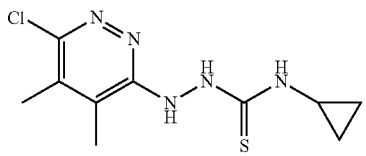

6-Chloro-4,5-dimethylpyridazin-3-yl)hydrazine (W3.006, 540 mg) was dissolved in methylene chloride (50 ml), and cyclopropyl isothiocyanate (290 µl) was added while stirring. The mixture was stirred at RT for 7 h and then left to stand overnight. Thereafter, it was admixed with diethyl ether (50 ml) and stirred for 3 h, and the precipitate formed was filtered off with suction. The precipitate was washed with ether and dried under reduced pressure. 830 mg of the title compound were obtained.

LC-MS rt: 0.62 min [M+H]$^+$: 272.1 (met. b)

W3.167

N*-(6-Chloro-4,5-dimethylpyridazin-3-yl)amino-N-(isopropyl)thiourea

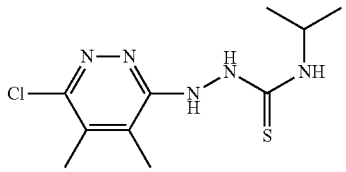

6-Chloro-4,5-dimethylpyridazin-3-yl)hydrazine (W3.006, 380 mg) was reacted with isopropyl isothiocyanate (235 µl) and worked up analogously to W3.166. The precipitate obtained was 428 mg. The mother liquor was dried and purified using silica gel (70 g cartridge, DCM/methanol gradient 0-30% within 30 min). This afforded a further 119 mg of product.

LC-MS rt: 0.78 min [M+H]$^+$: 274.1 (met. b)

W3.168

N*-(6-Chloro-5-methylpyridazin-3-yl)amino-N-(isopropyl)thiourea

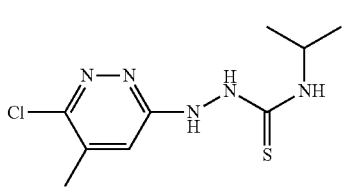

6-Chloro-5-dimethylpyridazin-3-yl)hydrazine as the trifluoroacetic acid salt (W3.005, 660 mg) was dissolved in DCM (55 ml), while stirring with isopropyl isothiocyanate (258 µl) and triethylamine (310 ml) was added. Workup and isolation were effected analogously to the method described in W3.167. In this case, 140 mg of the title compound were isolated as a precipitate. LC-MS rt: 0.81 min [M+H]$^+$: 260.1 (met. b)

W3.169

N'-(6-Chloro-4,5-dimethylpyridazin-3-yl)amino-N-methylthiourea

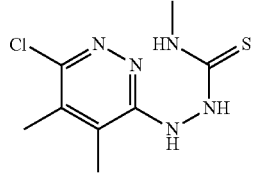

(6-Chloro-4,5-dimethylpyridazin-3-yl)hydrazine (W3.006; 8.00 g) was dissolved in DCM (400 ml) and admixed with methyl isothiocyanate (3.39 g). Subsequently, the mixture was stirred at RT for 24 h and left to stand over the weekend. The precipitate was filtered off, washed with DCM and dried in a drying cabinet at 45° C. 11.25 g of the title compound were obtained.

LC-MS rt: 0.29 min [M+H]+: 246.1 (met. b)

W3.170

N'-(6-Chloro-4-methylpyridazin-3-yl)amino-N-methylthiourea

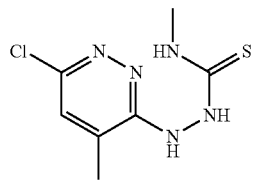

(6-Chloro-4-methylpyridazin-3-yl)hydrazine (W3.002; 5.5 g) was reacted and worked up analogously to W3.169. However, stirring was carried out for three days instead of one. 7.75 g of the title compound were obtained.

LC-MS rt: 0.20 min [M+H]$^+$: 232.1 (met. b)

W4

W4.003 and W4.014

3,6-Dichloro-4-ethylpyridazine and 3,6-dichloro-4,5-diethylpyridazine

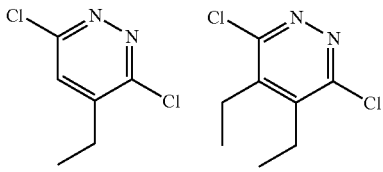

In analogy to: Samaritoni, Org. Prep. Proc. Int. 117 (1988)

3,6-Dichloropyridazine (10 g), silver nitrate (5.7 g) and propionic acid (7.5 ml) were initially charged in water (125 ml) and, at 50° C., concentrated sulfuric acid (11 ml) was added dropwise. After the addition, the reaction mixture was heated to 60° C. and a solution of ammonium persulfate (46 g) in water (125 ml) was slowly added dropwise within 20 min. After the addition, the mixture was heated to 70° C. for 30 min. After standing overnight, the reaction mixture was poured onto ice/water and adjusted to pH7 with 25% ammonium hydroxide solution. Then the mixture was extracted three times with dichloromethane. The combined organic phases were dried over sodium sulfate and, after the desiccant had been filtered off, dried under reduced pressure. The residue was purified by means of preparative HPLC (met. C). The product fractions, each of them clean, were combined, freed of the acetonitrile under reduced pressure and extracted three times with dichloromethane. The combined organic phases were dried over sodium sulfate and, after the desiccant had been filtered off, dried under reduced pressure. 6.6 g of 3,6- dichloro-4-ethylpyridazine and 3.0 g of 3,6-dichloro-4,5-diethylpyridazine were obtained.

3,6-Dichloro-4-ethylpyridazine, W4.003

LC-MS rt: 0.83 min [M+H]⁺: 177.1 (met. b)

3,6-Dichloro-4,5-diethylpyridazine, W4.014

LC-MS rt: 1.02 min [M+H]⁺: 205.1 (met. b)

W4.006

3,6-Dichloro-4,5-dimethylpyridazine

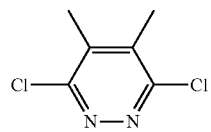

4,5-Dimethyl-1,2-dihydropyridazine-3,6-dione (W5.006; 69.7 g) was suspended in phosphorus oxychloride (150 ml) and heated to 80° C. for 2 h. After cooling, the mixture was added to ice-water and adjusted cautiously to pH 10 with 10 M NaOH while cooling with ice. The precipitate was filtered off with suction, washed with water and dried. 78.3 g of the title compound were obtained.

LC-MS rt: 0.63 min [M+H]⁺: 177.1 (met. b)

W4.009 and W4.015

3,6-Dichloro-4-isopropylpyridazine and 3,6-dichloro-4,5-diisopropylpyridazine

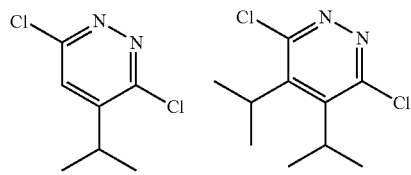

The compound was synthesized analogously to W4.003. 2.5 g of 3,6-dichloropyridazine and isobutyric acid (2.34 ml) were used to obtain 2.46 g of 3,6-dichloro-4-isopropylpyridazine and 0.33 g of 3,6-dichloro-4,5-diisopropylpyridazine.

3,6-Dichloro-4-isopropylpyridazine, W4.009

LC-MS rt: 0.96 min [M+H]⁺: 191.1 (met. b)

3,6-Dichloro-4,5-diisopropylpyridazine, W4.015

LC-MS rt: 1.14 min [M+H]⁺: 233.1 (met. b)

W4.010 and W4.016

3,6-Dichloro-4-cyclopropylpyridazine and 3,6-dichloro-4,5-dicyclopropylpyridazine

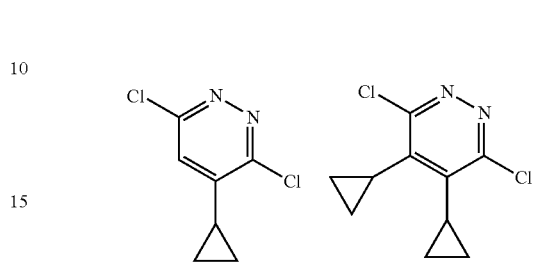

The compound was synthesized analogously to W4.003. 3 g of 3,6-dichloropyridazine and cyclopropanecarboxylic acid (2.41 ml) were used to obtain 1.6 g of 3,6-dichloro-4-cyclopropylpyridazine and 0.96 g of 3,6-dichloro-4,5-dicyclopropylpyridazine.

3,6-Dichloro-4-cyclopropylpyridazine, W4.010

LC-MS rt: 0.87 min [M+H]⁺: 189.1 (met. b)

3,6-Dichloro-4,5-dicyclopropylpyridazine, W4.016

LC-MS rt: 1.05 min [M+H]⁺: 229.1 (met. b)

W4.019

N,N-Diethyl-3,6-dichloropyridazine-4-carboxamide

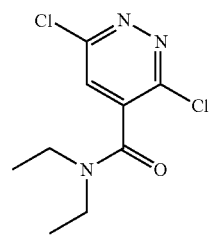

3,6-Dichloropyridazine-4-carbonyl chloride (2.5 g) was initially charged in DCM (25 ml) at RT. Thereafter, diethylamine (1.5 ml) predissolved in DCM (5 ml) was slowly added dropwise while stirring. After stirring at RT for 3 h, the mixture was admixed with water and extracted three times with DCM. The combined DCM phases were dried over sodium sulfate, filtered and concentrated. The residue was purified by means of silica gel (70 g cartridge, n-heptane/EA gradient). 1.8 g of the title compound were obtained.

LC-MS rt: 0.97 min [M+H]⁺: 248.1 (met. a)

W4.021

(3,6-Dichloropyridazin-4-yl)diethylamine

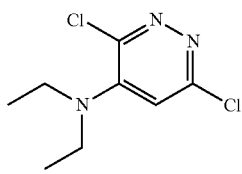

3,4,6-Trichloropyridazine (2 g) and diethylamine (2.4 ml) were initially charged in toluene (10 ml) and left to stand at RT for 3 days. Then the mixture was admixed with water and EA, and the EA phase was removed. The EA phase was washed three times with water, dried over magnesium sulfate, filtered and concentrated. The residue was purified using silica gel (70 g cartridge, n-heptane/EA gradient 0-50% within 60 min). 1.1 g of the title compound were obtained.
LC-MS rt: 1.24 min [M+H]$^+$: 248.1 (met. a)

W4.120

N-(5,6-Diethoxypyridazin-3-yl)-N-nitroamine

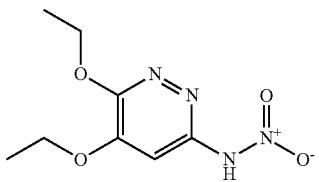

5,6-Diethoxypyridazin-3-ylamine (analogously to T. Horie in Chemical & Pharmaceutical Bulletin (1963), 11(9), 1157-67; 160 mg) was initially charged dissolved in concentrated sulfuric acid (4 ml) at RT. The mixture was then cooled to 0° C. and 2 ml of a 1:1 mixture of concentrated nitric acid and concentrated sulfuric acid were added dropwise. After 20 min at 0° C., the ice bath was removed and the mixture was stirred for 4 h. Then it was cooled again to 0° C., a further 0.5 ml of the acid mixture was added and the mixture was stirred at 0° C. for another hour. Then it was admixed with ice while cooling with ice. After adding DCM, the phases were separated and extracted three times with DCM. The combined DCM phases were dried over sodium sulfate, filtered and concentrated. 188 mg of the title compound were obtained.
LC-MS rt: 0.81 min [M+H]$^+$: 236.2 (met. b)

W5

W5.006

4,5-Dimethyl-1,2-dihydropyridazine-3,6-dione

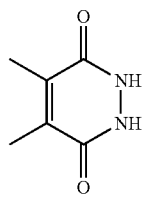

Hydrazine dihydrochloride (83.6 g) was dissolved in water (20 ml) and heated to 100° C., and 3,4-dimethylfuran-2,5-dione (100.4 g) was introduced while stirring. Then the mixture was heated to reflux for 3 h. Subsequently, the precipitate formed was filtered off with suction, washed with water and dried. The residue was suspended in EA (2 l), filtered off with suction and dried. 69.7 g of the title compound were obtained.
LC-MS rt: 0.19 min[M+H]+: 141.1 (met. b)

Synthesis of the Units of the "Eastern Half"

O1.001

N-[3-(2-Bromoacetyl)-5-(pentafluorosulfanyl)phenyl]acetamide

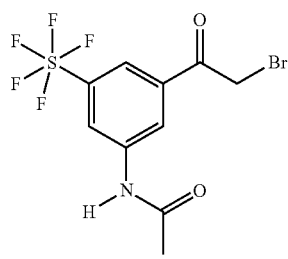

N-[3-Acetyl-5-(pentafluorosulfanyl)phenyl]acetamide (859 mg, for synthesis see example 1) was dissolved in a mixture of methanol (10 ml) and THF (10 ml) and phenyltrimethylammonium tribromide (1.065 g) was added in portions while stirring. After stirring at RT for 2 h, the mixture was heated to 40° C. for a further 3 h. After cooling, the reaction mixture was added to 2 N sulfuric acid and the aqueous phase was extracted 3 times with ethyl acetate. The combined extracts were dried over sodium sulfate, filtered and concentrated. The crude product was purified using silica gel with ethyl acetate/heptane as the eluent. 480 mg of the desired compound were obtained. LC-MS rt: 1.47 min [M+H]$^+$: 382.0 (met. a)

O1.002

2-Bromo-1-(3,5-di-tert-butyl-4-hydroxyphenyl)ethanone (Apollo Scientific)

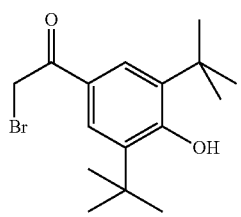

O1.003

2-Bromo-1-(3-tert-butyl-4-methoxy-5-morpholin-4-ylphenyl)ethanone

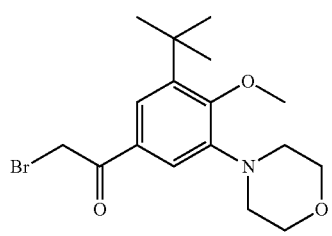

Prepared as described in WO 2004/078721.

O1.004

2-Bromo-1-(4-methoxy-3-morpholin-4-yl-5-trifluoromethylphenyl)ethanone

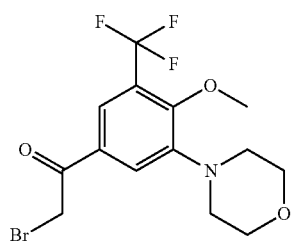

4-[5-(1,1-Dimethoxyethyl)-2-methoxy-3-trifluormethylphenyl]morpholine (O2.004; 460 mg) was dissolved in a mixture of methanol (1.4 ml) and THF (4 ml), the mixture was cooled to 7° C., and phenyltrimethylammonium tribromide (530 mg) was added in portions while stirring. After stirring at RT for 3 h, the mixture was left to stand overnight. Then aqueous thiosulfate solution (0.8 ml; w=5%) and water (4 ml) were added, and the mixture was admixed with EA and extracted three times with EA. The combined extracts were dried over magnesium sulfate, filtered and concentrated. The residue was dissolved in a mixture of acetonitrile (20 ml) and water (0.5 ml) and admixed with TFA (0.5 ml) while stirring. After stirring at RT for 5 h, the solvent was drawn off, and the residue was admixed with water, neutralized with saturated sodium hydrogencarbonate solution and extracted three times with ethyl acetate. The combined extracts were dried over magnesium, filtered and concentrated. The crude product was purified using silica gel with ethyl acetate/heptane as the eluent. 200 mg of the desired compound were obtained.

LC-MS rt: 1.67 min [M+H]$^+$: 382.0 (met. a)

O1.006

2-Bromo-1-[3-methylamino-5-(pentafluorosulfanyl)phenyl]ethanone

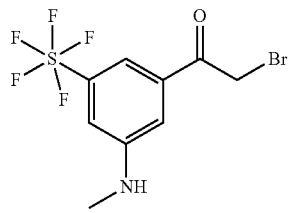

N-[3-(2-Bromoacetyl)-5-(pentafluoro sulfanyl)phenyl]-2,2,2-trifluoro-N-methylacetamide (O1.075; 1.2 g) was admixed with water (15 ml), and concentrated sulfuric acid (15 ml) was added dropwise while stirring and with ice cooling. The mixture was heated to 80° C. and stirred at this temperature for 7 h. After cooling, the reaction mixture was added slowly to a mixture of 10 N sodium hydroxide solution and EA, and the aqueous phase was extracted five times with EA. The combined organic phases were dried over magnesium sulfate and, after the desiccant had been filtered off, dried under reduced pressure. The residue was purified by means of preparative HPLC (met. A). The product fractions, each of them clean, were combined, freed of the acetonitrile under reduced pressure, neutralized with sodium hydrogencarbonate and extracted three times with EA. The combined organic phases were dried over magnesium sulfate and, after the desiccant had been filtered off, dried under reduced pressure. 420 mg of the title compound were isolated.

LC-MS rt: 1.64 min [M+H]$^+$: 354.0 (met. a)

O1.007

2-Bromo-1-[3-methoxy-5-(pentafluorosulfanyl)phenyl]ethanone

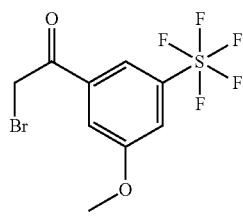

1-[3-Methoxy-5-(pentafluorosulfanyl)phenyl]ethanone (O2.007; 1.63 g) was dissolved in THF (150 ml), and phenyltrimethylammonium tribromide (2.2 g) was added at RT while stirring. After stirring at RT for 2 h, the mixture was admixed with water, neutralized with sodium hydrogencarbonate solution and extracted three times with EA. The alkaline water phase was extracted 3× with EA. The combined organic phases were dried over magnesium sulfate and, after the desiccant had been filtered off, dried under reduced pressure. The residue was purified by means of preparative HPLC (met. A). The product fractions, each of them clean, were combined, freed of the acetonitrile under reduced pressure, neutralized with sodium hydrogencarbonate and extracted three times with EA. The combined organic phases were dried over magnesium sulfate and, after the desiccant had been filtered off, dried under reduced pressure. 1.27 g of the title compound were isolated. LC-MS rt: 1.65 min [M+H]$^+$: 354.9 (met. b)

O1.008

2-Bromo-1-(3-tert-butyl-5-ethoxymethylphenyl)ethanone

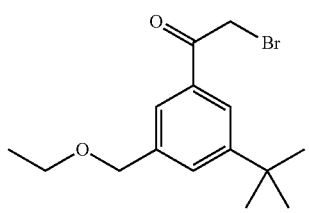

1-(3-tert-Butyl-5-ethoxymethylphenyl)ethanone (O2.008; 550 mg) was dissolved in methanol/THF (10 ml/10 ml), admixed with phenyltrimethylammonium tribromide (882 mg) while stirring and stirred at RT for 2 h. Subsequently, the reaction mixture was poured onto DCM (200 ml) and washed thoroughly once with 5% sodium thiosulfate solution and once with water. Then the DCM phase was dried and concentrated. The residue was purified using silica gel (40 g cartridge, n-heptane/EA gradient of 0-50% in 30 min). 566 mg of the title compound were obtained. LC-MS rt: 1.83 min [M+H]$^+$: 313.2 (met. a)

The following were prepared analogously:

| Number | | LC-MS rt | [M + H]$^+$ | Comment: |
|---|---|---|---|---|
| O1.009 | | 1.92 min | 339.2 (met. a) | O2.009; 595 mg; product: 691 mg |
| O1.010 | | 2.01 min | 343.2 (met. a) | O2.010; 410 mg; product: 405 mg |
| O1.011 | | 1.77 min | 299.2 (met. a) | O2.011; 390 mg; 5% citric acid solution added instead of thiosulfate; product: 387 mg |
| O1.012 | | 1.94 min | 327.2 (met. a) | O2.012; 333 mg; stirred at RT for 12 h; stirred with 20% citric acid solution instead of thiosulfate solution 1 h; product: 327 mg |

-continued

| Number | | LC-MS rt | [M + H]+ | Comment: |
|---|---|---|---|---|
| O1.013 | (structure) | 2.16 min | 395.3 (met. a) | O2.013; 540 mg; after thiosulfate solution, washed additionally with 20% citric acid solution; product: 600 mg |

O1.014

2-Bromo-1-(3-methoxy-5-trifluoromethylphenyl)ethanone

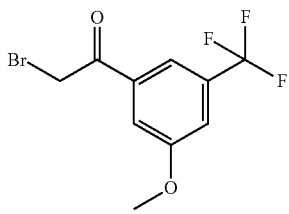

1-(3-Methoxy-5-trifluormethylphenyl)ethanone (O2.014, 50 mg) was dissolved in DCM (0.8 ml) and added dropwise at RT to a mixture of copper(II) bromide (102 mg) in EA (1.2 ml). After heating to RT for 2 h, the mixture was left to stand overnight, then the reaction mixture was filtered through "Celite" and washed thoroughly with EA, and the filtrate was dried. The residue was taken up with EA and semisaturated sodium hydrogencarbonate solution and then extracted twice with EA. The combined EA phases were washed with semisaturated sodium hydrogencarbonate solution, dried over sodium sulfate, filtered and concentrated. The crude product was purified by means of preparative HPLC (met. A). The product fractions, each of them clean, were combined, freed of the acetonitrile under reduced pressure and extracted three times with EA. The combined organic phases were dried over sodium sulfate and, after the desiccant had been filtered off, dried under reduced pressure. 39 mg of the title compound were isolated.

LC-MS rt: 1.64 min [M+H]+: 297.0 (met. a)

The following were prepared analogously to O1.008:

| Number | | LC-MS rt | [M + H]+ | Comment: |
|---|---|---|---|---|
| O1.015 | (structure) | 1.77 min | 285.1 (met. a) | O2.015; 880 mg; 5% citric acid solution added instead of thiosulfate solution; product; 327 mg |
| O1.016 | (structure) | 1.97 min | 325.1 (met. a) | O2.016; 1.02 g; stirred with 5% citric acid solution for 2 h instead of thiosulfate solution; product: 1.23 g |
| O1.017 | (structure) | 2.14 min | 339.2 (met. a) | O2.017; 25 mg; stirred with 5% citric acid solution for 2 h instead of thiosulfate solution; product: 314 mg |

-continued

| Number | | LC-MS rt | [M + H]⁺ | Comment: |
|---|---|---|---|---|
| O1.018 | 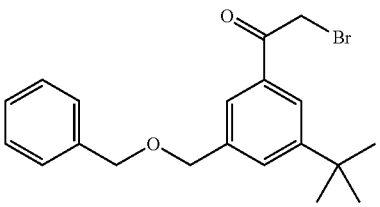 | 2.18 min | 389.3 (met. a) | O2.018; 638 mg; stirred with 5% citric acid solution for 2 h instead of thiosulfate solution; product: 809 mg |
| O1.019 | 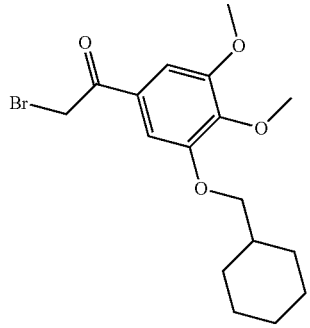 | 1.94 min | 371.3 (met. a) | O2.019; 360 mg; after thiosulfate solution, washed additionally with 20% citric acid solution; product: 261 mg |
| O1.020 | 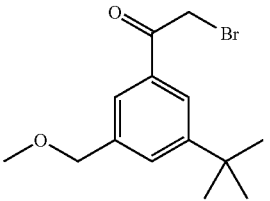 | 1.72 min | 299.1 (met. a) | O2.020; 1.53 g; after thiosulfate solution, washed additionally with 20% citric acid solution; product: 1.04 g |
| O1.021 | 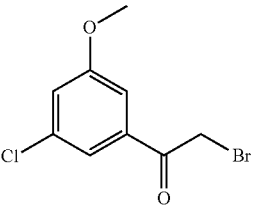 | 1.58 min | 262.9/ 265.0 (met. a) | O2.021; 41 g; after thiosulfate solution, washed additionally with 20% citric acid solution; product: 572 mg |

O1.022

2-Bromo-1-(8-tert-butyl-4-methyl-3,4-dihydro-2H-benzo[1,4]oxazin-6-yl)ethanone

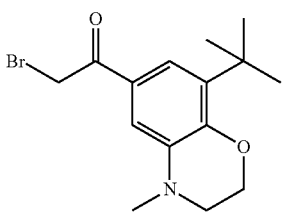

1-(8-tert-Butyl-4-methyl-3,4-dihydro-2H-benzo[1,4]oxazin-6-yl)ethanone (250 mg, purchased from Chembiotek, India) was heated to from 50° C. to 55° C. in a mixture of acetic acid (4 ml) and toluene (8 ml). At this temperature, bromine (200 mg dissolved in acetic acid) was cautiously added dropwise. After 2.5 h, the heating was removed, and the mixture was admixed at RT with ice-water and extracted three times with toluene. The combined organic phases were dried over sodium sulfate, filtered and concentrated. The crude product was purified using silica gel, so as to obtain 65 mg of the desired compound, as well as a further 43 mg of product which was slightly contaminated and 37 mg of reactant.

LC-MS rt: 1.81 min [M+H]⁺: 326.0 (met. a)

O1.030

2-Bromo-1-(3-isopropyl-5-methoxyphenyl)ethanone

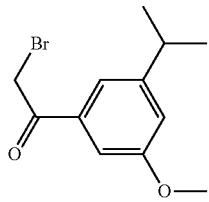

1-(3-Isopropyl-5-methoxyphenyl)ethanone (O2.030; 425 mg) was dissolved in methanol/THF 15 ml/15 ml) and admixed while stirring with phenyltrimethylammonium tribromide (831 mg). After stirring at RT for 3 h, the reaction mixture was added to 50 ml of 20% citric acid and stirred for 1 h. After adding water and EA, the EA phase was removed, dried and concentrated. The residue was dissolved in acetonitrile (50 ml), and 2 N sulfuric acid (15 ml) was added to the solution. After standing at RT for 2 h, the mixture was admixed with water and extracted with EA. The EA phase was washed with saturated sodium hydrogencarbonate solution, dried and concentrated. The residue was purified using silica gel (40 g cartridge, n-heptane/EA gradient of 0-50% within 30 min). 520 mg of the title compound were obtained.

LC-MS rt: 1.65 min [M+H]$^+$: 271.1 (met. a)

O1.031

2-Bromo-1-(3-cyclohexylmethoxy-5-ethoxyphenyl)ethanone

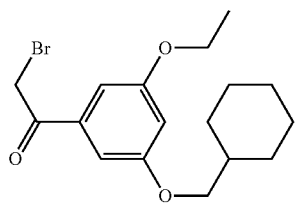

Proceeding from 1-(3-cyclohexylmethoxy-5-ethoxyphenyl)ethanone (O2.031, 1.76 g), the title compound was prepared analogously to O1.008. For further purification, however, the silica gel chromatography was followed by a further purification by means of preparative HPLC. 370 mg of the title compound were obtained.

LC-MS rt: 2.11 min [M+H]$^+$: 355.1 (met. a)

O1.032

2-Bromo-1-(3-bromo-5-methoxyphenyl)ethanone

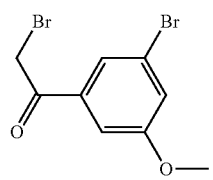

1-(3-Bromo-5-methoxyphenyl)ethanone (O2.032, 1.45 g) was dissolved in methanol/THF (40 ml/40 ml) and admixed while stirring with phenyltrimethylammonium tribromide (2.38 g). After stirring at RT for 24 h, water and EA were added. The EA phase was removed, dried and concentrated. The residue was dissolved in acetonitrile (50 ml), and 2 N sulfuric acid (15 ml) was added to the solution. After standing at RT for 1 h, the mixture was admixed with water and extracted twice with EA. The EA phase was washed with saturated sodium hydrogencarbonate solution, dried and concentrated. The residue was purified using silica gel (40 g cartridge, n-heptane/EA gradient of 0-50% within 30 min. 1.39 g of the title compound were obtained.

$^1$H NMR (500 MHz, DMSO-d6) [ppm]: 7.71 (1H), 7.48 (2H), 4.97 (2H), 3.84 (3H)

O1.034

2-Bromo-1-[3-(3,3-dimethylbutoxy)-5-ethoxyphenyl]ethanone

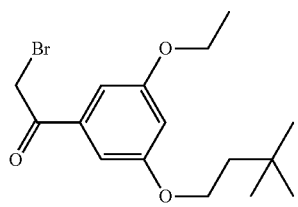

Proceeding from 1-[3-(3,3-dimethylbutoxy)-5-ethoxyphenyl]ethanone (O2.034; 950 mg), the title compound was obtained analogously to O1.031. 236 mg of the title compound were obtained, which was still somewhat contaminated.

LC-MS rt: 2.06 min [M+H]$^+$: 343.2 (met. a)

O1.035

2-Bromo-1-(3-cyclohexylmethoxy-5-methoxyphenyl)ethanone

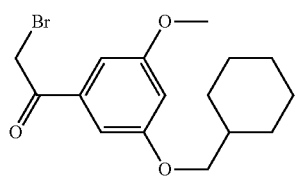

1-(3-Cyclohexylmethoxy-5-methoxyphenyl)ethanone (O2.035; 1.33 g) was converted analogously to O1.032. However, the mixture was stirred at RT only for 3 h instead of 24. 950 mg of the title compound were obtained. LC-MS rt: 2.03 min [M+H]$^+$: 341.2 (met. a)

O1.041

2-Bromo-1-(5-bromo-2,3-dimethoxyphenyl)ethanone

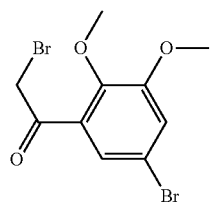

1-(5-Bromo-2,3-dimethoxyphenyl)ethanone (O2.041; 1.1 g) was converted analogously to O1.032. 1.21 g of the title compound were obtained.

LC-MS rt: 1.62 min [M+H]⁺: 337.0 (met. a)

O1.042

2-Bromo-1-(3-chloro-4,5-dimethoxyphenyl)ethanone

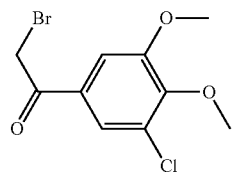

1-(3-Chloro-4,5-dimethoxyphenyl)ethanone (O2.042; 490 mg) was converted analogously to O1.032. 577 mg of the title compound were obtained.

LC-MS rt: 1.54 min [M+H]⁺: 293.0 (met. a)

O1.043

2-Bromo-1-[3-tert-butyl-5-(2-methoxyethoxy)phenyl]ethanone

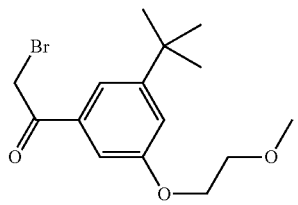

1-[3-tert-Butyl-5-(2-methoxyethoxy)phenyl]ethanone (O2.043; 1 g) was dissolved in methanol/THF (25 ml/25 ml), admixed with phenyltrimethylammonium tribromide (882 mg) while stirring and stirred at RT overnight. Then 50 ml of 20% citric acid solution were added and the mixture was stirred for 1 h. Subsequently, DCM (200 ml) was added and the mixture was extracted three times with DCM. Then the combined DCM phases were dried over magnesium sulfate, filtered and concentrated. The residue was purified using silica gel (40 g cartridge, n-heptane/EA gradient of 0-30% in 30 min). 1.31 g of the title compound were obtained.

LC-MS rt: 1.72 min [M+H]⁺: 329.2 (met. a)

O1.044

2-Bromo-1-[3-morpholin-4-yl-5-(pentafluorosulfanyl)phenyl]ethanone

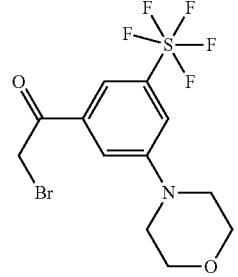

1-[3-Morpholin-4-yl-5-(pentafluorosulfanyl)phenyl]ethanone (O2.044; 1.1 g) was dissolved in methanol/THF (20/20 ml) and admixed while stirring with phenyltrimethylammonium tribromide (1.25 g). After stirring at RT for 27 h, 50 ml of 20% citric acid were added and the mixture was stirred for 1 h. After adding DCM (100 ml), the DCM phase was removed, dried and concentrated. The residue was dissolved in acetonitrile (100 ml), and 2 N sulfuric acid (20 ml) was added to the solution. After stirring at RT for 24 h, the mixture was admixed with water and extracted with EA. The EA phase was washed with saturated sodium hydrogencarbonate solution, dried and concentrated. The residue was purified using silica gel (80 g cartridge, n-heptane/EA gradient of 0-60% within 40 min). 866 mg of the title compound were obtained. LC-MS rt: 1.69 min [M+H]⁺: 410.0 (met. a)

O1.061

2-Bromo-1-[3-tert-butyl-5-(2-hydroxyethoxy)phenyl]ethanone

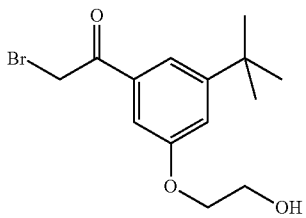

1-{3-tert-Butyl-5-[2-(tetrahydropyran-2-yloxy)ethoxy]phenyl}ethanone (O2.061; 3.9 g) was dissolved in methanol/THF (60 ml/60 ml) and admixed while stirring with phenyltrimethylammonium tribromide (5.03 g). After stirring at RT for 3 h, the mixture was added to 20% citric acid and stirred for 1 h. After adding EA, the EA phase was removed, dried and concentrated. The residue was purified using silica gel (80 g cartridge, n-heptane/EA gradient of 0-50% within 60 min). 2.56 g of the title compound were obtained.

LC-MS rt: 0.90 min [M+H]⁺: 315.0 (met. b)

| Number | | LC-MS rt | [M + H]+ | Comment:: |
|---|---|---|---|---|
| O1.070 | 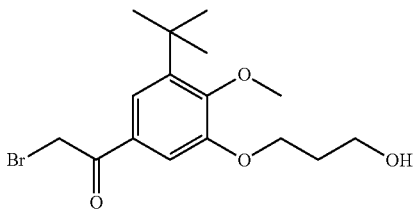 | 0.96 min | 345.1 (met. b) | Synthesis analogous to O1.071: O2.070 NUF3.153: 6.68 g; product: 3.3 g NUF3.154 |

O1.071

2-Bromo-1-[3-tert-butyl-5-(3-hydroxypropoxy)-4-methoxyphenyl]ethanone

1-{3-tert-Butyl-4-methoxy-5-[3-(tetrahydropyran-2-yloxy)propoxy]phenyl}ethanone (O2.071; 12.7 g) was dissolved in methanol/THF (200/200 ml) and admixed with phenyltrimethylammonium tribromide (13.1 g) while stirring. The mixture was stirred at RT for 1 h, then diluted with DCM and washed once with 5% sodium thiosulfate solution. The DCM phase was dried over magnesium sulfate, filtered and concentrated. The residue was taken up in acetonitrile (100 ml) and admixed with 48% hydrobromic acid (5.91 ml). The mixture was left to stand for 1 h, then admixed with water, extracted by shaking with EA, and the combined EA phases were dried over magnesium sulfate, filtered and concentrated. The residue was purified using silica gel (120 g cartridge, n-heptane/MtB ether gradient of 0-100% in 60 min). 3.29 g of the title compound were obtained.

LC-MS rt: 1.01 min [M+H]+: 359.1 (met. b)

O1.075

N-[3-(2-Bromoacetyl)-5-(pentafluorosulfanyl)phenyl]-2,2,2-trifluoro-N-methylacetamide

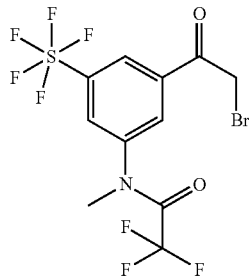

N-[3-Acetyl-5-(pentafluorosulfanyl)phenyl]-2,2,2-trifluoro-N-methylacetamide (O2.075; 1.03 g) was dissolved in a mixture of methanol (20 ml) and THF (20 ml). Phenyltrimethylammonium tribromide (1.05 g) was added while stirring. After stirring at RT for 5 h, the mixture was left to stand overnight, then further phenyltrimethylammonium tribromide (100 mg) was added and the mixture was heated to 60° C. for 2 h. After cooling, the reaction mixture was added to 2 N sulfuric acid and stirred for 10 min. Then the aqueous phase was extracted three times with EA. The combined organic phases were dried over magnesium sulfate and, after the desiccant had been filtered off, dried under reduced pressure. 1.2 g of the title compound were obtained, which had sufficient purity for the next reactions.

LC-MS rt: 1.72 min [M+H]+: 449.9 (met. a)

O2.004

4-[5-(1,1-Dimethoxyethyl)-2-methoxy-3-trifluoromethylphenyl]morpholine

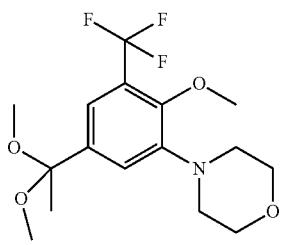

1-Bromo-5-(1,1-dimethoxyethyl)-2-methoxy-3-trifluoromethylbenzene (O3.004; 700 mg) was initially charged in dioxane (7 ml) and admixed successively with Pd(II) acetate (46 mg), cesium carbonate (2 g), 9,9-dimethyl-4,5-bis(diphenylphosphino)xanthene (118 mg) and morpholine (0.27 ml). Thereafter, the reaction mixture was heated to 90° C. for 7 h and then left to stand overnight. Subsequently, it was filtered and the filtrate was concentrated by rotary evaporation. The residue was purified using silica gel (50 g cartridge, n-heptane/EA gradient). 433 mg of the title compound were obtained.

LC-MS rt: 1.55 min [M+H]+: 304.0 (met. a)

O2.007

1-[3-Methoxy-5-(pentafluorosulfanyl)phenyl]ethanone

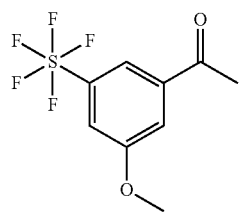

3,N-Dimethoxy-N-methyl-5-(pentafluorosulfanyl)benzamide (O3.007; 2.0 g) was dissolved in absolute THF (60 ml), and methylmagnesium bromide (5.2 ml, 3 M in diethyl ether) was added dropwise at 0° C. while stirring. After addition, the ice bath was removed and the mixture was stirred at RT for 2 h. 1 N hydrochloric acid was then added dropwise while cooling, followed by water and ethyl acetate. The organic phase was removed and the aqueous phase was extracted twice more with ethyl acetate. The combined extracts were dried over magnesium sulfate, filtered and concentrated. The residue was purified by means of preparative HPLC (met. A). The product-containing fractions were combined, freed of the acetonitrile and extracted three times with ethyl acetate. The combined extracts were dried over magnesium sulfate, filtered and concentrated. 1.63 g of the desired compound were obtained.

$^1$H NMR (400 MHz, DMSO-d6) [ppm]: 7.87 (1H), 7.75 (1H), 7.67 (1H), 3.91 (3H), 2.64 (3H)

O2.008

1-(3-tert-Butyl-5-ethoxymethylphenyl)ethanone

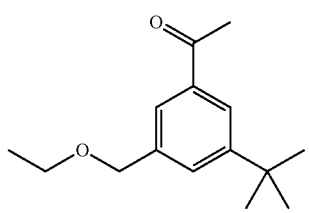

3-tert-Butyl-N-methoxy-5-methoxymethyl-N-methylbenzamide (O3.008; 854 mg) was converted analogously to O2.043. 550 mg of the title compound were obtained.

LC-MS rt: 1.70 min [M+H]$^+$: 235.3 (met. a)

O2.009

1-(3-tert-Butyl-5-cyclopropylmethoxymethylphenyl)ethanone

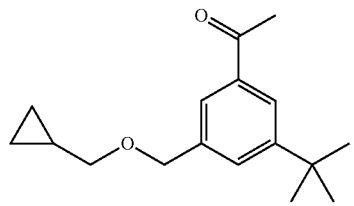

Proceeding from methyl 3-tert-butyl-5-hydroxymethylbenzoate and cyclopropylmethyl bromide, the title compound (600 mg) was prepared analogously to O5.008 to O2.008.

LC-MS rt: 1.81 min [M+H]$^+$: 261.2 (met. a)

O2.010

1-(3-tert-Butyl-4,5-diethoxyphenyl)ethanone

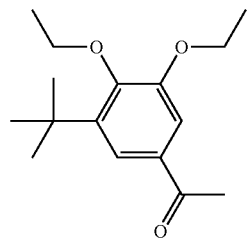

1-(3-tert-Butyl-4-ethoxy-5-hydroxyphenyl)ethanone (O3.010; 470 mg) and ethyl iodide (193 µl) were dissolved in DMF (6.2 ml), and sodium hydride (57 mg) was added. After stirring at RT for 0.5 h, the DMF was drawn off and the residue was taken up in EA, washed with water, dried and concentrated. The residue was purified using silica gel (40 g cartridge, n-heptane/EA gradient 0-30% within 60 min). 420 mg of the title compound were obtained. LC MS rt: 1.93 min [M+H]$^+$: 265.2 (met. a)

O2.011

1-(3-tert-Butyl-5-ethoxyphenyl)ethanone

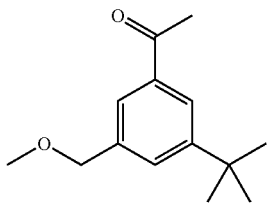

Methyl 3-tert-butyl-5-hydroxybenzoate (O6.043) was reacted with ethyl iodide analogously to O5.043 and converted to the title compound analogously to the sequence of O4.043 to O2.043. 390 mg were obtained.

LC-MS rt: 1.72 min [M+H]+: 221.3 (met. a)

O2.012

1-(3-tert-Butyl-5-propoxymethylphenyl)ethanone

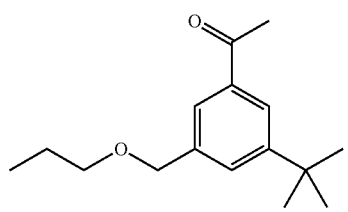

Proceeding from methyl 3-tert-butyl-5-hydroxymethylbenzoate and propyl iodide, the title compound (333 mg) was prepared analogously to O5.008 to O2.008.

LC-MS rt: 1.81 min [M+H]+: 261.2 (met. a)

O2.013

1-(3-tert-Butyl-4,5-bis(cyclopropylmethoxy)phenyl)ethanone

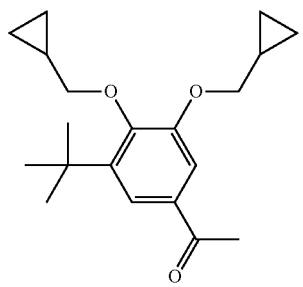

Proceeding from 2-bromo-6-tert-butyl-4-(1,1-dimethoxyethyl)phenol and cyclopropyl bromide, the title compound (547 mg) was prepared analogously to O4.010 to O2.010.

LC-MS rt: 2.10 min [M+H]+: 317.4 (met. a)

O2.014

1-(3-Methoxy-5-trifluoromethylphenyl)ethanone

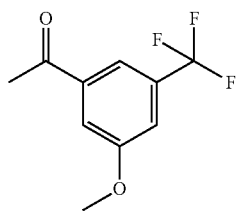

3,N-Dimethoxy-N-methyl-5-trifluoromethylbenzamide (O3.014, 460 mg) was initially charged in THF (15 ml) under at RT Ar dissolved. Thereafter, the mixture was cooled to 0° C., and methylmagnesium bromide (1.5 ml; 3 M in diethyl ether) was added dropwise. Subsequently, the ice bath was removed and the mixture was stirred at RT for 2 h. Then the mixture was admixed with 1 N hydrochloric acid while cooling with ice, diluted with water and extracted three times with EA. The combined EA phases were dried over sodium sulfate, filtered and concentrated. 349 mg of the title compound were isolated.

$^1$H NMR (500 MHz, DMSO-d6) [ppm]: 7.80 (1H), 7.73 (1H), 7.53 (1H), 3.92 (3H), 2.66 (3H)

O2.015

1-(3-tert-Butyl-5-methoxyphenyl)ethanone

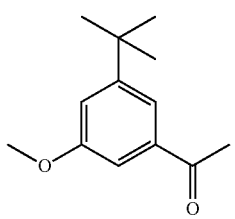

Methyl 3-tert-butyl-5-hydroxybenzoate (O6.043) was reacted with methyl iodide analogously to O5.043 and converted to the title compound analogously to the sequence of O4.043 to O2.043. 880 mg were obtained.

LC-MS rt: 1.65 min [M+H]+: 207.1 (met. a)

O2.016

1-(3-tert-Butyl-5-cyclopropylmethoxyphenyl)ethanone

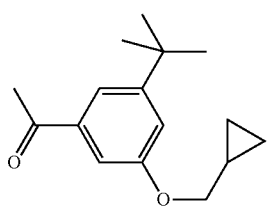

Methyl 3-tert-butyl-5-hydroxybenzoate (O6.043) was reacted with cyclopropylmethyl bromide analogously to O5.043, and converted to the title compound analogously to the sequence O4.043 to O2.043. 1.02 g were obtained.

LC-MS rt: 1.86 min [M+H]+: 247.1 (met. a)

O2.017

1-(3-tert-Butyl-5-cyclobutylmethoxyphenyl)ethanone

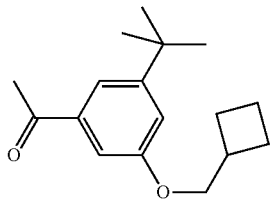

Methyl 3-tert-butyl-5-hydroxybenzoate (O6.043) was reacted with bromomethylcyclobutane analogously to O5.043 and converted to the title compound analogously to the sequence O4.043 to O2.043. 252 mg were obtained.

LC-MS rt: 2.07 min [M+H]$^+$: 261.2 (met. a)

O2.018

1-(3-Benzyloxymethyl-5-tert-butylphenyl)ethanone

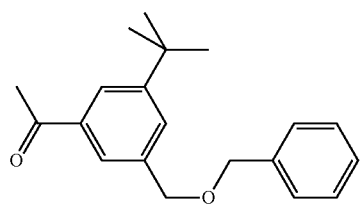

Methyl 3-tert-butyl-5-hydroxymethylbenzoate was reacted with benzyl bromide analogously to O5.043 and converted to the title compound analogously to the sequence O4.008 to O2.008. 638 mg were obtained.

LC-MS rt: 1.93 min [M+H]$^+$: 297.2 (met. a)

O2.019

1-(3-Cyclohexylmethoxy-4,5-dimethoxyphenyl)ethanone

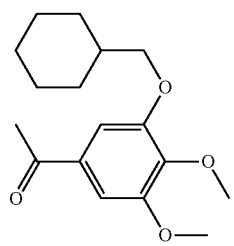

3-Cyclohexylmethoxy-4,5,N-trimethoxy-N-methylbenzamide (420 mg) was converted and worked up analogously to O2.059. No silica gel purification was performed. 370 mg were obtained.

LC-MS rt: 1.82 min [M+H]$^+$: 293.2 (met. a)

O2.020

1-(3-tert-Butyl-5-methoxymethylphenyl)ethanone

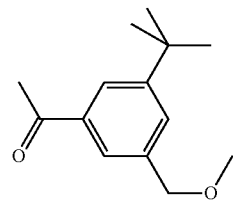

Methyl 3-tert-butyl-5-hydroxymethylbenzoate was reacted with methyl iodide analogously to O5.043, and converted to the title compound analogously to the sequence O4.008 to O2.008. 1.54 g were obtained.

LC-MS rt: 1.58 min [M+H]$^+$: 221.1 (met. a)

O2.021

1-(3-Chloro-5-methoxyphenyl)ethanone

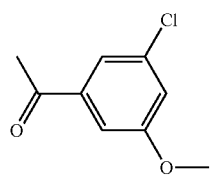

3-Chloro-5-methoxybenzoic acid (3 g) was reacted analogously to O3.043/O2.043 with thionyl chloride (23.3 ml) and N,O-dimethylhydroxylamine hydrochloride (1.57 g) and methylmagnesium bromide (8.91 ml). 2.42 g were obtained.

$^1$H NMR (500 MHz, DMSO-d6) [ppm]: 7.54 (1H), 7.40 (1H), 7.30 (1H), 3.84 (3H), 2.58 (3H)

O2.030

1-(3-Isopropyl-5-methoxyphenyl)ethanone

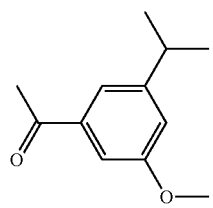

Methyl 3-hydroxy-5-isopropylbenzoate was reacted with methyl iodide analogously to O5.043 and converted to the title compound analogously to the sequence O4.043 to O2.043. 425 mg were obtained. LC-MS rt: 1.54 min [M+H]$^+$: 193.1 (met. a)

O2.031

1-(3-Cyclohexylmethoxy-5-ethoxyphenyl)ethanone

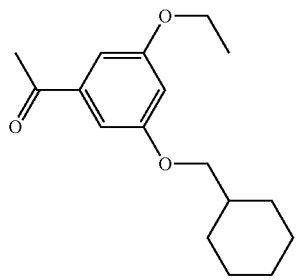

1-(3,5-Dihydroxyphenyl)ethanone (1.0 g) and ethyl bromide (0.531 ml) were dissolved at RT in DMF (20 ml), and sodium hydride (189 mg) was added. After stirring at 50° C. for 2 h, cyclohexylmethyl bromide (1.36 ml) was added, followed by further sodium hydride (315 mg). After stirring at 50° C. for another 2 h, the DMF was drawn off and the residue was taken up in EA, washed with water, dried, filtered and concentrated. The residue was purified using silica gel (80 g cartridge, n-heptane/EA gradient of 0-20% within 60 min). 378 mg of the title compound were obtained. LC-MS rt: 2.07 min [M+H]$^+$: 277.2 (met. a)

O2.032

1-(3-Bromo-5-methoxyphenyl)ethanone

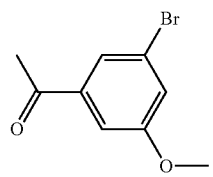

Methyl 3-bromo-5-methoxybenzoate (O5.032; 2.50 g) was converted to the title compound analogously to the sequence of O4.043, O3.043 and O2.059. 1.45 g were obtained.

LC-MS rt: 1.46 min [M+H]$^+$: 229.0 (met. a)

O2.034

1-[3-(3,3-Dimethylbutoxy)-5-ethoxyphenyl]ethanone

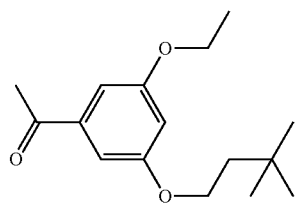

1-(3,5-Dihydroxyphenyl)ethanone (3.0 g) were converted analogously to O2.031. Instead of cyclohexylbromide, however, 1-bromo-3,3-dimethylbutane was used. After chromatography, 960 mg of the title compound were obtained.

LC-MS rt: 1.99 min [M+H]$^+$: 265.2 (met. a)

O2.035

1-(3-Cyclohexylmethoxy-5-methoxyphenyl)ethanone

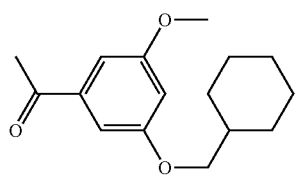

1-(3-Hydroxy-5-methoxyphenyl)ethanone (O3.033; 1.5 g) and bromomethylcyclohexane (1.76 g) were dissolved in DMF (20 ml), and sodium hydride (260 mg) was added. After stirring at 50° C. for 24 h, the DMF was drawn off. The residue was taken up in EA, washed with water, dried, filtered and concentrated. The residue was purified using silica gel (40 g cartridge, n-heptane/EA 0-50% within 30 min). 1.33 g of the title compound were obtained.

LC-MS rt: 1.93 min [M+H]$^+$: 263.2 (met. a)

O2.041

1-(5-Bromo-2,3-dimethoxyphenyl)ethanone

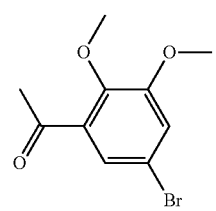

5-Bromo-2,3-dimethoxybenzoic acid (2 g) was converted to the benzamide derivative analogously to O3.043, and the latter to the title compound analogously to O2.059. 1.1 g of the title compound were obtained. LC-MS rt: 3.70 min [M+H]$^+$: 259.0 (met. d)

O2.042

1-(3-Chloro-4,5-dimethoxyphenyl)ethanone

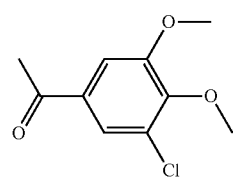

3-Chloro-4,5-dimethoxybenzoic acid (1 g) was converted to the benzamide derivative analogously to O3.043, and the latter to the title compound analogously to O2.059. 495 mg of the title compound were obtained. LC-MS rt: 1.55 min [M+H]⁺: 215.1 (met. a)

O2.043

1-[3-tert-Butyl-5-(2-methoxyethoxy)phenyl]ethanone

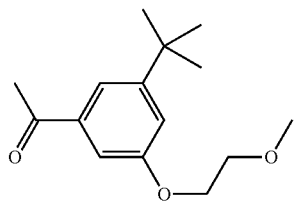

3-tert-Butyl-N-methoxy-5-(2-methoxyethoxy)-N-methyl-benzamide (O3.043; 1.35 g) was dissolved in THF (40 ml), methylmagnesium bromide (3.05 ml, 3 M in ether) was added dropwise at 0° C. and then the mixture was stirred at RT for 2 h. Then the mixture was admixed with 1 N hydrochloric acid (50 ml), diluted with water and extracted by shaking three times with EA. Then the combined EA phases were dried over magnesium sulfate, filtered and concentrated. The residue was purified using silica gel (40 g cartridge, n-heptane/EA gradient of 0-30% in 30 min). 1.0 g of the title compound were obtained.

LC-MS rt: 1.58 min [M+H]⁺: 251.3 (met. a)

O2.044

1-[3-Morpholin-4-yl-5-(pentafluorosulfanyl)phenyl]ethanone

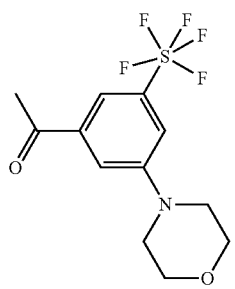

N-Methoxy-N-methyl-3-morpholin-4-yl-5-(pentafluorosulfanyl)benzamide (O3.044; 2.38 g) was converted and worked up analogously to O2.043. The purification was effected using silica gel (80 g cartridge, n-heptane/EA gradient of 0-70% within 40 min). 1.1 g of the title compound were obtained.

LC-MS rt: 1.57 min [M+H]⁺: 332.0 (met. a)

O2.059

1-[3-tert-Butyl-5-(3-hydroxypropoxy)phenyl]ethanone

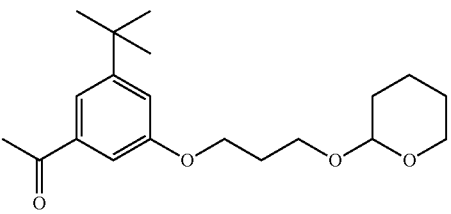

3-tert-Butyl-N-methoxy-N-methyl-5-[3-(tetrahydropyran-2-yloxy)propoxy]benzamide (O3.059; 5.49 g) was dissolved in THF (100 ml), cooled to 0° C. and admixed with lithium bis(trimethylsilyl)amide (14.47 ml, 1 M in MTB ether). After stirring at 0° C. for 30 min, methylmagnesium bromide (9.65 ml, 3 M in ether) was added dropwise. The cooling bath was removed and, after stirring at RT for 2 h, the mixture was diluted with water and extracted by shaking with EA. The EA phase was dried over magnesium sulfate, filtered and concentrated by rotary evaporation. The residue was purified using silica gel (200 g, n-heptane/EA 4:1). 3.4 g of the title compound were obtained.

¹H NMR (500 MHz, DMSO-d6) [ppm] (representative signals): 7.53 (1H); 7.28 (1H); 7.17 (1 H); 4.57 (1H, —O—C(—C)H—O—); 4.11 (2H); 2.57 (3H)

O2.061

1-{3-tert-Butyl-5-[2-(tetrahydropyran-2-yloxy)ethoxy]phenyl}ethanone

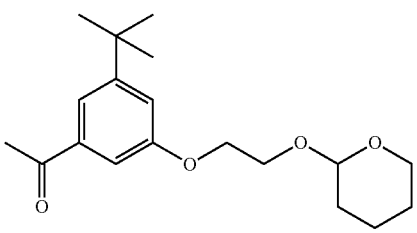

Proceeding from methyl 3-tert-butyl-5-hydroxybenzoate (O6.043) and 2-(2-bromoethoxy)-tetrahydropyran, the synthesis sequence O5.059 to O2.059 was followed. 3.9 g of the title compound were obtained.

¹H NMR (500 MHz, DMSO-d6) [ppm] (representative signals): 7.53 (1H), 7.31 (1H), 7.20 (1H), 4.66 (1H, —O—C(—C)H—O—), 4.20 (2H), 2.58 (3H)

O2.070

1-{3-tert-Butyl-4-methoxy-5-[2-(tetrahydropyran-2-yloxy)ethoxy]phenyl}ethanone

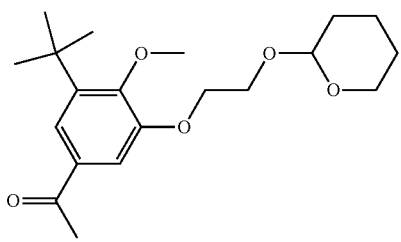

Analogously to O2.071, 1-(3-tert-butyl-5-hydroxy-4-methoxyphenyl)ethanone (O3.070; 5.0 g) was reacted with 2-(2-bromoethoxy)tetrahydropyran (5.64 g). However, the crude product was purified using silica gel (40 g cartridge, n-heptane/EA gradient of 0-50% within 60 min). 6.68 g of the title compound were obtained.

$^1$H NMR (500 MHz, DMSO-d6) [ppm] (representative signals): 7.50 (2H, aromatic), 4.70 (1H, —O—C(—C)H—O—), 3.90 (3H, —OCH$_3$), 2.54 (3H, acetyl)

O2.071

1-{3-tert-Butyl-4-methoxy-5-[3-(tetrahydropyran-2-yloxy)propoxy]phenyl}ethanone

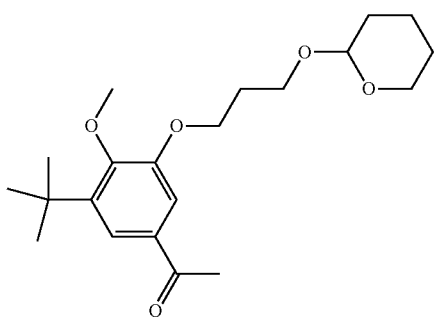

1-(3-tert-Butyl-5-hydroxy-4-methoxyphenyl)ethanone (O3.070; 6.9 g) and 2-(3-bromo-propoxy)tetrahydropyran (8.31 g) were dissolved in DMF (80 ml), and sodium hydride (894 mg) was added. After stirring at RT for 5 hours, the solvent was drawn off and the residue was taken up with EA. The EA phase was washed with water, dried and concentrated. 12.7 g of the title compound were obtained as a crude product in sufficient purity.

$^1$H NMR (400 MHz, DMSO-d6) [ppm] (representative signals): 4.57 (1H, —O—C(—C)H—O—), 2.54 (3H, acetyl)

O2.075

N-[3-Acetyl-5-(pentafluorosulfanyl)phenyl]-2,2,2-trifluoro-N-methylacetamide

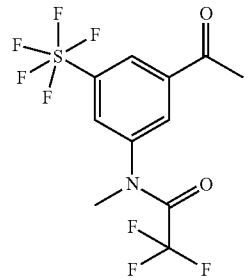

In a microwave insert, N-(3-acetyl-5-pentafluorosulfanylphenyl)-2,2,2-trifluoroacetamide (O3.075; 0.25 g) was dissolved in absolute dimethoxyethane (7.5 ml), powdered potassium carbonate was added and the mixture was admixed with iodomethane (80 μl). Subsequently, the mixture was heated in the microwave to 100° C. for 40 min. Once further N-(3-acetyl-5-pentafluorosulfanylphenyl)-2,2,2-trifluoroacetamide (4×250 mg) had been converted in the manner described, the five batches were worked up together, by decanting from potassium carbonate into 1 N hydrochloric acid with ice cooling. After repeatedly washing the potassium carbonate residue with dimethoxyethane, the aqueous phase was extracted five times with ethyl acetate. The combined extracts were dried over magnesium sulfate, filtered and concentrated. The residue was purified by means of preparative HPLC (met. A). The product-containing fractions were combined, freed of the acetonitrile and extracted five times with ethyl acetate. The combined extracts were dried over magnesium sulfate, filtered and concentrated. 1.03 g of the desired compound were obtained. LC-MS rt: 1.62 min [M+H]$^+$: 372.0 (met. a)

O3

O3.004

1-Bromo-5-(1,1-dimethoxyethyl)-2-methoxy-3-trifluoromethylbenzene

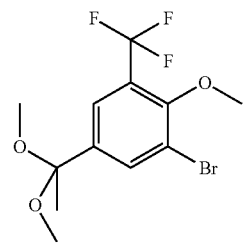

1-(3-Bromo-4-hydroxy-5-trifluoromethylphenyl)ethanone (O4.004; 6.8 g) was dissolved in methanol (50 ml) and admixed successively with DL-10-camphorsulfonic acid (111 mg) and trimethyl orthoformate (8 ml). After stirring at RT for 2 h, DMF (75 ml), potassium carbonate (4.98 g) and then slowly, while cooling with ice, iodomethane (3 ml) were added. After stirring at RT for 4 h, the reaction mixture was left to stand overnight and then admixed with n-heptane/water, and the organic phase was removed. The aqueous phase was extracted by shaking once more with n-heptane, and the combined organic phases were then dried over magnesium sulfate, filtered and concentrated. 7 g of the title compound were obtained in sufficient purity.

$^1$H NMR (500 MHz, DMSO-d6) [ppm]: 7.90 (1H), 7.62 (1H), 3.89 (3H), 3.10 (6H), 1.49 (3 H)

O3.007

3,N-Dimethoxy-N-methyl-5-(pentafluorosulfanyl)benzamide

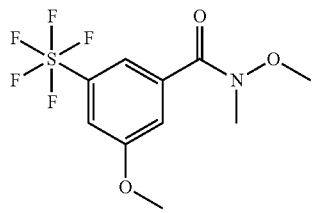

Methyl 3-methoxy-5-(pentafluorosulfanyl)benzoate (O4.007; 2.5 g) was dissolved in absolute THF (65 ml), and N,O-dimethylhydroxylamine hydrochloride (1.2 g) was added. Then the mixture was cooled to −15° C. and isopropylmagnesium bromide solution (13.59 ml, 2 M in THF) was added dropwise. After 20 min, the cooling bath was removed and the mixture was stirred at RT for 1 h. Then ammonium chloride solution was added and the aqueous phase was extracted three times with ethyl acetate. The combined extracts were dried over magnesium sulfate, filtered and concentrated. The crude product thus obtained still contained significant reactant, and was therefore converted and worked up again as described above. No reactant was present any longer in the residue which was then obtained. Purification was effected by means of preparative HPLC (met. A). The product-containing fractions were combined and freed of the acetonitrile, and the aqueous phase was extracted three times with EA. The combined extracts were dried over magnesium sulfate, filtered and concentrated. 1.78 g of the desired compound were obtained.

$^1$H NMR (400 MHz, CDCl$_3$) [ppm]: 7.70 (1H), 7.37 (1H), 7.24 (1H+CDCl$_3$), 3.88 (3H), 3.56 (3H)

O3.008

3-tert-Butyl-5-ethoxymethyl-N-methoxy-N-methyl-benzamide

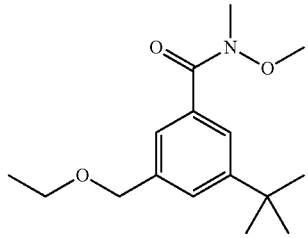

Analogously to O3.043, 3-tert-butyl-5-ethoxymethylbenzoic acid (O4.008; 1.15 g) was first converted to the acid chloride (1.24 g), and then the 3-tert-butyl-5-ethoxymethyl-benzoyl chloride obtained was converted further. 854 mg of the title compound were obtained.

LC-MS rt: 3.32 min [M+H]$^+$: 280.2 (met. d)

O3.010

1-(3-tert-Butyl-4-ethoxy-5-hydroxyphenyl)ethanone

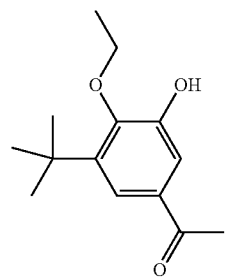

1-Bromo-3-tert-butyl-5-(1,1-dimethoxyethyl)-2-ethoxy-benzene (O4.010; 19.68 g) was converted analogously to O3.070. 5.15 g of the title compound were obtained.

LC-MS rt: 0.972 min [M+H]$^+$: 237.1 (met. b)

O3.014

3,N-Dimethoxy-N-methyl-5-trifluoromethylbenzamide

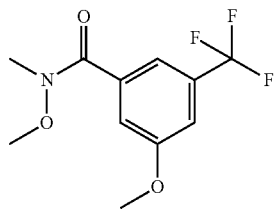

Methyl 3-methoxy-5-trifluoromethylbenzoate (O4.014, 1 g) and N,O-dimethylhydroxylamine (416 mg) were initially charged in THF (30 ml). Thereafter, the mixture was cooled to −15° C., and isopropylmagnesium chloride (3.2 ml; 2 M in THF) was added dropwise within 10 min. The mixture was stirred at −15° C. for another 20 min before the cooling bath was removed. After 3 h, the mixture was cooled again to −15° C. and further isopropylmagnesium chloride (3.2 ml) was added. After the cooling bath had been removed, the mixture was stirred at RT for another hour, then admixed with 20% ammonium chloride solution and extracted three times with EA. The combined EA phases were dried over sodium sulfate, filtered and concentrated. The residue was purified using silica gel (50 g cartridge, DCM as eluent). 465 mg of the title compound were obtained, as well as 427 mg of reactant.

LC-MS rt: 1.36 min [M+H]$^+$: 264.0 (met. a)

O3.033

1-(3-Hydroxy-5-methoxyphenyl)ethanone

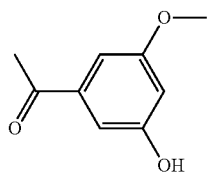

1-(3,5-Dihydroxyphenyl)ethanone (3 g) and methyl iodide (2.80 g) were dissolved in DMF (40 ml), and sodium hydride (568 mg) was added. After stirring at RT for 2 h, the DMF was drawn off. The residue was taken up in EA and washed with water, dried, filtered and concentrated. The residue was purified using silica gel (89 g cartridge, n-heptane/EA 0-50% within 30 min). 1.12 g of the title compound were obtained.

$^1$H NMR (500 MHz, DMSO-d6) [ppm]: 9.8 (1H); 6.93 (2H); 6.58 (1H); 3.76 (3H); 2.50 (3H+DMSO)

O3.043

3-tert-Butyl-N-methoxy-5-(2-methoxyethoxy)-N-methylbenzamide

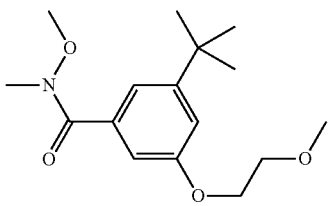

3-tert-Butyl-5-(2-methoxyethoxy)benzoic acid (O4.043; 1.9 g) was dissolved in thionyl chloride (10.9 ml), kept under reflux for 2 h and then concentrated. The resulting 3-tert-butyl-5-(2-methoxyethoxy)benzoyl chloride (2.04 g) was dissolved in DCM (20 ml) and admixed with dimethylhydroxylamine (734 mg), then Hünig's base (1.37 ml) was added and the mixture was stirred at RT for 1 h. Then the mixture was dried, the residue was taken up in EA, and the mixture was washed four times with water, dried over magnesium sulfate, filtered and concentrated by rotary evaporation. The residue was purified using silica gel (40 g cartridge, n-heptane/EA gradient of 0-50% in 40 min). 1.36 g of the title compound were obtained.

LC-MS rt: 1.43 min [M+H]$^+$: 296.3 (met. a)

O3.044

N-Methoxy-N-methyl-3-morpholin-4-yl-5-(pentafluorosulfanyl)benzamide

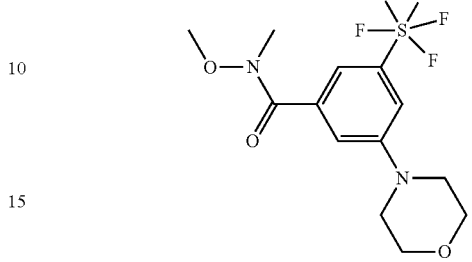

3-Amino-N-methoxy-N-methyl-5-(pentafluorosulfanyl) benzamide (O5.075; 6.3 g) was dissolved in DMF (80 ml), and cesium carbonate (10.1 g), sodium iodide (0.62 g) and bis(2-bromoethyl)ether (19.37 g) were added. The mixture was divided between 10 microwave vessels, each of which was heated to 130° C. for 3 h. Subsequently, the batches were combined and freed of solvent. The residue was taken up in EA and washed with water. The EA phase was dried and concentrated. The residue was purified using silica gel (120 g cartridge, n-heptane/EA gradient of 0-100% within 30 min). 2.48 g of the title compound were obtained.

LC-MS rt: 1.41 min [M+H]$^+$: 377.0 (met. a)

O3.059

3-tert-Butyl-N-methoxy-N-methyl-5-[3-(tetrahydropyran-2-yloxy)propoxy]benzamide

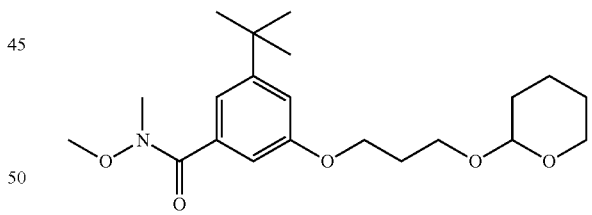

3-tert-Butyl-5-[3-(tetrahydropyran-2-yloxy)propoxy]benzoic acid (O4.059; 4.90 g) and N,O-dimethylhydroxylaminehydrochloride (1.42 g) were dissolved in DMF (80 ml) and admixed with Hünig's base (4.81 ml) and TOTU (4.78 g). After stirring for 2 h, the mixture was left to stand overnight. Then the DMF was drawn off, the mixture was partitioned between EA and saturated sodium hydrogencarbonate solution, and the EA phase was removed, dried over magnesium sulfate, filtered and concentrated. 5.49 g of the title compound were obtained.

$^1$H NMR (500 MHz, DMSO-d6) [ppm] (representative signals): 7.12 (1H), 7.01 (1H), 6.90 (1H), 4.56 (1H, —O—C(—C)H—O—), 4.06 (2H), 3.57 (3H), 3.22 (3H)

O3.070

1-(3-tert-Butyl-5-hydroxy-4-methoxyphenyl)ethanone

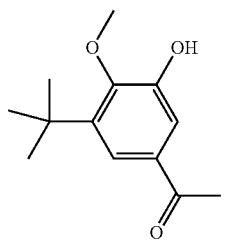

1-Bromo-3-tert-butyl-5-(1,1-dimethoxyethyl)-2-methoxybenzene (O4.070; 36.3 g) was dissolved in THF (1 l), n-butyllithium (52.6 ml; 2.5 M in hexane) was added dropwise at −75° C. under argon, and the mixture was stirred for a further 30 min. Then trimethyl borate (37.3 ml) was added dropwise and the mixture was allowed to come to RT within 2 h. Subsequently, sodium hydroxide (4.4 g, dissolved in 10 ml of water) and hydrogen peroxide solution (62.3 ml; 35% in water) were added successively. After stirring at RT for 2 h, the mixture was left to stand overnight. Then water and EA were added and the mixture was acidified with hydrochloric acid. After removing the EA phase, this was dried over magnesium sulfate and concentrated. The residue was purified using silica gel (330 g cartridge, n-heptane/EA gradient of 0-50% within 60 min). 14 g of the title compound were obtained.

LC-MS rt: 0.90 min [M+H]$^+$: 223.1 (met. b)

O3.075

N-(3-Acetyl-5-pentafluorosulfanylphenyl)-2,2,2-trifluoroacetamide

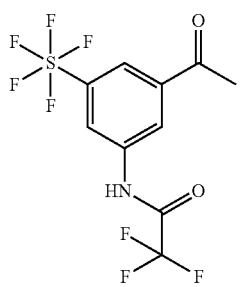

N-Methoxy-N-methyl-3-(pentafluorosulfanyl)-5-(2,2,2-trifluoroacetylamino)benzamide (O4.075; 1.65 g) was dissolved in THF (25 ml). At 0° C., lithium bis(trimethylsilyl)amide (0.9 ml) was added while stirring. After 30 min, methylmagnesium bromide (3.5 ml, 3 M in diethyl ether) was added dropwise. After the addition had ended, the ice bath was removed and the mixture was stirred at RT for 2 h. While cooling, 1 N hydrochloric acid, water and EA were then added. After removing the organic phase, the aqueous phase was extracted twice more with EA. The combined EA phases were dried with magnesium sulfate, filtered and concentrated. The crude product is a mixture of N-(3-acetyl-5-pentafluorosulfanyl-phenyl)-2,2,2-trifluoroacetamide and 1-[3-amino-5-(pentafluorosulfanyl)phenyl]ethanone, and so the crude product (1.3 g) was taken up in methylene chloride (60 ml) and admixed with triethylamine (155 μl). Thereafter, trifluoroacetic anhydride (160 μl) was added while stirring. After stirring at RT for 3 h, water and saturated sodium hydrogencarbonate solution were added, the phases were separated and the DCM phase was washed three times more with water. The DCM phase was dried with magnesium sulfate, filtered and concentrated. 1.3 g of the title compound were obtained.

LC-MS rt: 1.61 min [M+H]$^+$: 358.0 (met. a)

O4

O4.004

1-(3-Bromo-4-hydroxy-5-trifluoromethylphenyl)ethanone

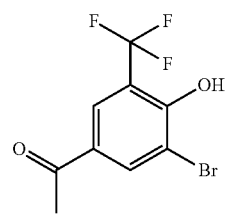

1-(4-Hydroxy-3-trifluoromethylphenyl)ethanone (5 g) was initially charged in acetonitrile (150 ml) at RT while stirring, and cooled to −10° C. At this temperature, N-bromosuccinimide (4.5 g, dissolved in 100 ml of acetonitrile) was added dropwise. Then the cooling bath was removed and the mixture was stirred for a further 5 h. After standing overnight, ¾ of the solvent was drawn off and the residue was admixed with n-heptane/water. The organic phase was removed and washed once with 5% sodium thiosulfate solution and once with water. The precipitate formed was filtered off with suction, washed and dried. 6.9 g of the title compound were obtained in sufficient purity. LC-MS rt: 1.35 min [M+H]$^+$: 283.0 (met. a)

O4.007

Methyl 3-methoxy-5-(pentafluorosulfanyl)benzoate

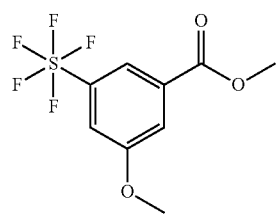

3-Hydroxy-5-(pentafluorosulfanyl)benzoic acid (O5.007; 3.0 g) was dissolved in absolute DMF (75 ml). Then iodomethane (3.6 ml) was added while stirring, followed by finely powdered potassium carbonate (6.3 g). After stirring at 40° C. for 5 hours, the mixture was cooled and admixed with water (250 ml). The mixture was then extracted four times with ether (100 ml). The combined extracts were each washed once with 1 N sodium hydroxide solution (75 ml) and water (100 ml), dried over magnesium sulfate, filtered and concentrated. 2.9 g of the desired compound were obtained.

$^1$H NMR (400 MHz, CDCl$_3$) [ppm]: 8.00 (1H), 7.70 (1H), 7.47 (1H), 3.96 (3H), 3.90 (3H)

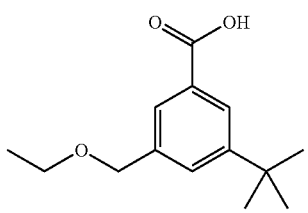

O4.008

3-tert-Butyl-5-ethoxymethylbenzoic acid

Methyl 3-tert-butyl-5-ethoxymethylbenzoate (O5.008; 1.18 g) was converted analogously to O4.043. However, the crude product obtained was subsequently purified using silica gel (50 g cartridge, n-heptane/EA gradient of 0-50% within 30 min). 1.15 g of the title compound were obtained.

$^1$H NMR (400 MHz, DMSO-d$_6$) [ppm]: 12.90 (1H), 7.86 (1H), 7.73 (1H), 7.57 (1H), 4.50 (2H), 3.50 (1H), 1.30 (9H), 1.16 (3H)

O4.010

1-Bromo-3-tert-butyl-5-(1,1-dimethoxyethyl)-2-ethoxybenzene

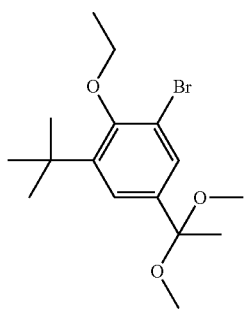

2-Bromo-6-tert-butyl-4-(1,1-dimethoxyethyl)phenol (20 g; for synthesis see CA02515715) was alkylated with ethyl iodide analogously to the conditions of O4.070. 19.67 g of the title compound were obtained.

$^1$H NMR (500 MHz, DMSO-d6) [ppm]: 7.46 (1H), 7.33 (1H), 4.03 (2H), 3.06 (6H), 1.43 (3H), 1.38 (3H), 1.35 (9H)

O4.014

Methyl 3-methoxy-5-trifluoromethylbenzoate

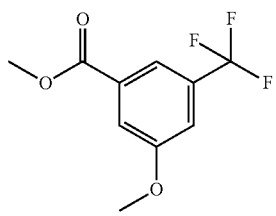

3-Hydroxy-5-trifluoromethylbenzoic acid (2 g) was initially charged at RT in DMF (15 ml) while stirring, and admixed dropwise with methyl iodide (3.0 ml). After adding potassium carbonate (5.6 g), the mixture was stirred for 5 h and left to stand overnight. It was then admixed with water and extracted three times with MtB ether. The combined MTB ether phases were dried over sodium sulfate, filtered and concentrated. 2.29 g of the title compound were obtained.

$^1$H NMR (500 MHz, DMSO-d6) [ppm]: 7.76 (1H), 7.70 (1H), 7.55 (1H), 3.91 (3H), 3.89 (3 H)

O4.043

3-tert-Butyl-5-(2-methoxyethoxy)benzoic acid

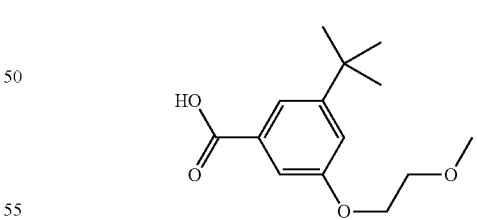

Methyl 3-tert-butyl-5-(2-methoxyethoxy)benzoate (O5.043; 2.0 g) was dissolved in methanol (30 ml) and THF (60 ml), and lithium hydroxide solution (30 ml, 1 M in water) was added. The mixture was heated to 40° C. and stirred for 3 h. Then the organic solvents were drawn off and the aqueous phase was adjusted to pH 3 with 1 N hydrochloric acid. The mixture was extracted with EA, dried, filtered and concentrated. 1.9 g of the title compound were obtained.

LC-MS rt: 1.40 min [M+H−H$_2$O]$^+$: 235.3 (met. a)

O4.059

3-tert-Butyl-5-[3-(tetrahydropyran-2-yloxy)propoxy]benzoic acid

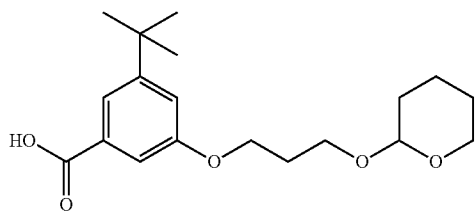

Methyl 3-tert-butyl-5-[3-(tetrahydropyran-2-yloxy)propoxy]benzoate (O5.059; 5.37 g) was dissolved in methanol (80 ml) and THF (160 ml), and lithiumhydroxide solution (61.28 ml, 1 M in water) was added. After stirring at 40° C. for 2 h, the mixture was dried, and the residue was taken up with water and freeze-dried. The product obtained was stirred with DCM, filtered and dried. 4.9 g of product were obtained.

$^1$H NMR (500 MHz, DMSO-d6) [ppm] (representative signals): 7.52 (1H), 7.26 (1H), 6.80 (1H), 4.57 (1H, —O—C(—C)H—O—), 4.02 (2H)

O4.070

1-Bromo-3-tert-butyl-5-(1,1-dimethoxyethyl)-2-methoxybenzene

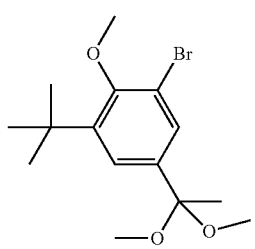

1-Bromo-3-tert-butyl-5-(1,1-dimethoxyethyl)-2-methoxybenzene was synthesized analogously to patent application CA 02515715.

$^1$H NMR (500 MHz, DMSO-d6) [ppm]: 7.47 (1H), 7.33 (1H), 3.85 (3H), 3.07 (6H), 1.43 (3H), 1.35 (9H)

O4.075

N-Methoxy-N-methyl-3-(pentafluorosulfanyl)-5-(2,2,2-trifluoroacetylamino)benzamide

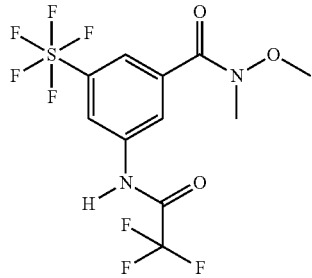

3-Amino-N-methoxy-N-methyl-5-pentafluorosulfanylbenzamide (O5.075; 1.45 g) was dissolved in methylene chloride (15 ml), and, while stirring, triethylamine (0.8 ml) followed by trifluoroacetic anhydride (0.85 ml) were added with exclusion of moisture. After stirring at RT for 3 h and standing overnight, water and saturated sodium hydrogencarbonate solution were added, the phases were separated and the methylene chloride phase was washed three times more with water, dried over magnesium sulfate, filtered and concentrated. The product obtained (1.75 g) was used in the next stage without further purification.

LC-MS rt: 1.53 min [M+H]$^+$: 403.0 (met. a)

O5

O5.007

3-Hydroxy-5-(pentafluorosulfanyl)benzoic acid

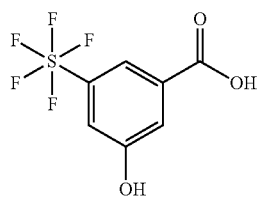

3-Amino-5-pentafluorosulfanylbenzoic acid (O6.007; 3.9 g) was dissolved in 35% sulfuric acid (120 ml) and cooled to −5° C., and a solution of sodium nitrite (1.1 g) in water (100 ml) was added dropwise within 10 min. After 40 min, further nitrite solution was added (2 ml), and another 2 ml and 1 ml after a further 20 min in each case. Then the cooling bath was removed and the mixture was heated to 100° C. After 5 h, the mixture was cooled and the solution was decanted. The clear, acidic solution was extracted five times with ethyl acetate. The combined extracts were dried over magnesium sulfate, filtered and concentrated. The crude product was recrystallized from ethyl acetate/heptane. 3.6 g of the desired compound were obtained.

$^1$H NMR (400 MHz, DMSO-d$_6$) [ppm]: 10.72 (1H); 7.71 (1H); 7.57 (1H); 7.46 (1H);

O5.008

Methyl 3-tert-butyl-5-ethoxymethylbenzoate

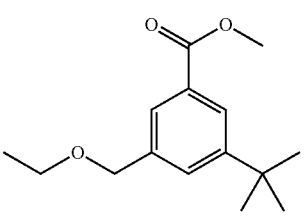

Methyl 3-tert-butyl-5-hydroxymethylbenzoate (2.0 g) was alkylated with ethyl iodide analogously to the conditions of O5.043. 1.18 g of the title compound were obtained.

LC-MS rt: 3.81 min [M+H]$^+$: 250.2 (met. d)

O5.032

Methyl 3-Bromo-5-methoxybenzoate

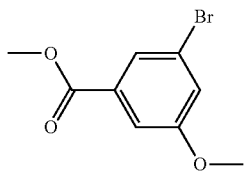

Methyl 3-bromo-5-hydroxybenzoate (O6.032; 2.52 g) was alkylated with methyl iodide and worked up analogously to the conditions of O5.043. 2.5 g of the title compound were obtained.

LC-MS rt: 1.58 min [M+H]$^+$: 245.0 (met. a)

O5.043

Methyl 3-tert-butyl-5-(2-methoxyethoxy)benzoate

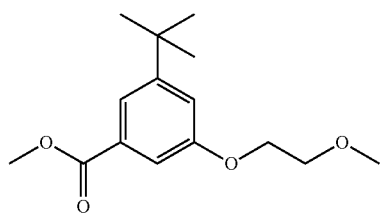

Methyl 3-tert-butyl-5-hydroxybenzoate (O6.043; 2.18 g) and 1-bromo-2-methoxyethane (1.18 ml) were dissolved in DMF (30 ml) and sodium hydride (301 mg) was added while stirring. After stirring at RT for 2 h, the solvent was drawn off. The residue was taken up in EA, and the mixture was washed with water, dried and concentrated. The residue was purified using silica gel (80 g cartridge, n-heptane/MtB ether gradient of 0-30% in 60 min). 2.0 g of the title compound were obtained.

LC-MS rt: 1.69 min [M+H−HOCH$_3$]$^+$: 235.2 (met. a)

O5.059

Methyl 3-tert-butyl-5-[3-(tetrahydropyran-2-yloxy)propoxy]benzoate

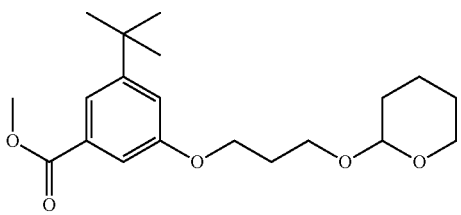

Methyl 3-tert-butyl-5-hydroxybenzoate (O6.043; 3.22 g) and 2-(3-bromopropoxy)-tetrahydropyran (4.14 g) were dissolved in DMF (30 ml), and sodium hydride (445 mg) was added. After stirring at RT for 3 h, the mixture was left to stand overnight. Then the DMF was drawn off and the residue was taken up in EA, washed with water, dried, filtered and concentrated. 5.37 g of product were obtained.

$^1$H NMR (500 MHz, DMSO-d6) [ppm] (representative signals): 7.56 (1H), 7.28 (1H), 7.19 (1H), 4.57 (1H, —O—C(—C)H—O—), 4.10 (2H)

O5.075

3-Amino-N-methoxy-N-methyl-5-pentafluorosulfanylbenzamide

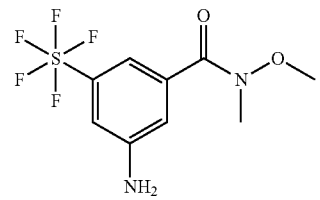

N-Methoxy-N-methyl-5-nitro-3-pentafluorosulfanylbenzamide (O6.075; 4.2 g) was dissolved in methanol (120 ml), and Raney nickel (about 700 mg) was added. With a hydrogen balloon attached, hydrogenation was effected on a magnetic stirrer. After 5 h, the catalyst was filtered off and washed with methanol. The filtrate was concentrated under reduced pressure and the residue was purified by means of preparative chromatography. The product-containing fractions were combined, freed of the acetonitrile, basified with sodium hydrogencarbonate solution and extracted three times with ethyl acetate. The combined extracts were dried over magnesium sulfate, filtered and concentrated. 1.73 g of the desired compound were obtained.

LC-MS rt: 1.27 min [M+H]$^+$: 307.0 (met. a)

O6

O6.007

3-Amino-5-pentafluorosulfanylbenzoic acid

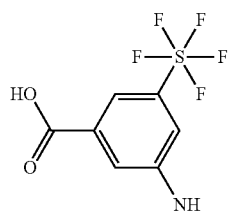

3-Pentafluorosulfanylbenzoic acid (15 g) was dissolved in fuming nitric acid (120 ml) and stirred at RT with exclusion of moisture. Then concentrated sulfuric acid (7.5 ml) was added and the mixture was stirred at 75° C. After stirring at 75° C. for 8 h, the mixture was left to stand overnight, then further sulfuric acid (1.5 ml) was added and the mixture was heated to 75° C. while stirring for 8 h. After being left to stand overnight, the mixture was added to ice-water and stirred for 2 h. Then the precipitate was filtered off with suction and dried under high vacuum. 13.7 g of 3-pentafluorosulfanyl-5-nitrobenzoic acid were obtained.

Subsequently, the 3-pentafluorosulfanyl-5-nitrobenzoic acid (5 g) was dissolved in methanol (300 ml), Raney nickel (about 750 mg) was added and hydrogenation was effected under a hydrogen atmosphere (hydrogen balloon). After 3 h, the catalyst was filtered off and the filter residue was washed thoroughly with methanol. The filtrate was concentrated and dried. The residue was purified using silica gel (2×50 g cartridge, n-heptane/EA gradient of 0-100% within 60 min). 3.9 g of the title compound were obtained.

$^1$H NMR (400 MHz, DMSO-d$_6$) [ppm]: 13.30 (1H); 7.37 (2H); 7.23 (1H); 5.98 (2H)

O6.043

Methyl 3-tert-butyl-5-hydroxybenzoate

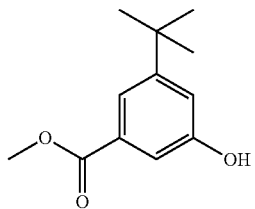

3-tert-Butyl-5-hydroxybenzoic acid (O7.043; 1.93 g) was dissolved in methanol (20 ml), and thionyl chloride (0.937 ml) was slowly added dropwise while stirring. After stirring at 65° C. for 1 h, the mixture was dried, the residue was taken up in DCM, and the solution was washed with saturated sodium hydrogencarbonate solution, dried over MgSO$_4$, filtered and concentrated by rotary evaporation. 2.19 g of the title compound were obtained.

LC-MS rt: 1.44 min [M+H]$^+$: 209.2 (met. a)

O6.075

N-Methoxy-N-methyl-5-nitro-3-pentafluorosulfanyl-benzamide

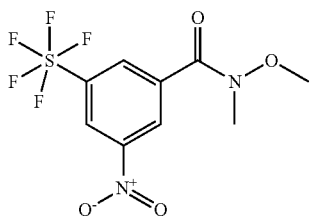

3-Pentafluorosulfanylbenzoic acid (5.0 g) was dissolved in fuming nitric acid (20 ml) and stirred at RT with exclusion of moisture. Then concentrated sulfuric acid (3 ml) was added and the mixture was stirred at 75° C. After stirring at 75° C. for 5 h, further sulfuric acid (2 ml) was added and the mixture was stirred at 75° C. for a further 2 h. After being left to stand overnight, the mixture was poured onto ice-water and stirred for 2 h. Then the precipitate was filtered off with suction and dried under high vacuum. 4.2 g of 3-pentafluorosulfanyl-5-nitrobenzoic acid were obtained. A further 900 mg were obtained from the mother liquor after extracting three times with methylene chloride, drying the combined methylene chloride phases over magnesium sulfate and concentrating the solvent. Subsequently, 4.0 g of the 3-pentafluorosulfanyl-5-nitrobenzoic acid were dissolved in thionyl chloride (25 ml) while stirring and kept under reflux with exclusion of moisture for 10 h. After standing overnight at RT, excess thionyl chloride was removed under reduced pressure, and the residue obtained was dissolved in dichloromethane (50 ml) and admixed while stirring with N,O-dimethylhydroxylamine× HCl (1.25 g) and diethylisopropylamine (1.66 g). After stirring at RT for 1 h, the mixture was concentrated under reduced pressure, and the residue was dissolved in ethyl acetate and washed five times with water. The organic phase was dried over magnesium sulfate, filtered and concentrated. The 4.2 g of crude product obtained were used directly in the next stage. LC-MS rt: 1.50 min [M+H]$^+$: 337.0 (met. a)

O7

O7.043

3-tert-Butyl-5-hydroxybenzoic acid

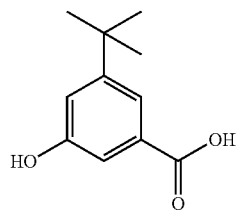

3-Bromo-5-tert-butylbenzoic acid (5 g) was dissolved in THF (180 ml), and n-butyllithium (18.7 ml, 2.5 M in hexane) was added dropwise under argon and at −75° C., and stirred for a further 30 min. Then trimethyl borate (6.63 ml) was added dropwise and the mixture was allowed to come to RT within 1 h. Thereafter, sodium hydroxide (0.778 g), dissolved in 2 ml of water, and hydrogen peroxide (12.89 ml, 30%) were added in succession. After stirring at RT for 3 h, the mixture was left to stand over the weekend. Then water and EA were added, the mixture was adjusted to pH 3 with 1 N hydrochloric acid and the EA phase was removed. This phase was washed three times with water, dried, filtered and concentrated. The residue was purified using silica gel (120 g cartridge, n-heptane/MtB ether gradient of 0-50% in 60 min). 1.94 g of the title compound were obtained.

LC-MS rt: 1.18 min [M+H]$^+$: 195.1 (met. a)

Example 1

1-{2-[3-Acetylamino-5-(pentafluorosulfanyl)phenyl]-2-oxoethyl}-3-amino-6-ethoxy-[1,2,4]triazolo[4,3-b]pyridazin-1-ium trifluoroacetate

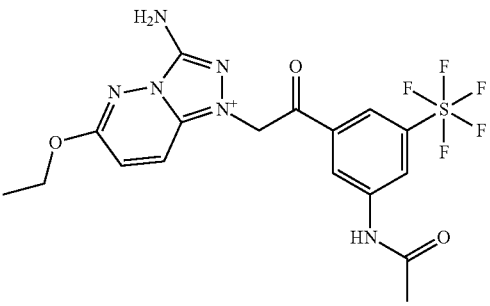

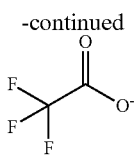

a) 3-Nitro-5-pentafluorosulfanylbenzoic acid

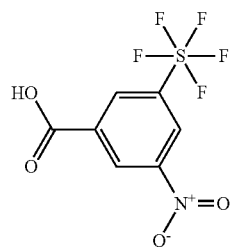

3-Pentafluorosulfanylbenzoic acid (5.0 g) was dissolved in fuming nitric acid (20 ml) and stirred at RT with exclusion of moisture. Then concentrated sulfuric acid (3 ml) was added and the mixture was stirred at 75° C. After stirring at 75° C. for 5 h, further sulfuric acid (1.5 ml) was added and, after stirring at 75° C. for 2 h, left to stand overnight. Then the mixture was added to ice-water and stirred for 2 h. The precipitate formed was filtered off with suction and dried under high vacuum. 4.2 g of 3-pentafluorosulfanyl-5-nitrobenzoic acid were obtained. A further 900 mg were obtained from the mother liquor after extracting three times with methylene chloride, drying the combined methylene chloride phases over magnesium sulfate and concentrating the solvent. The precipitate was used in the next stage without further purification.

$^{1}$H NMR (400 MHz, DMSO-$d_6$) [ppm]: 8.82 (1H); 8.80 (1H); 8.62 (1H)

b) N-Methoxy-N-methyl-5-nitro-3-pentafluorosulfanylbenzamide

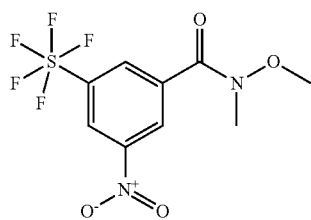

3-Nitro-5-pentafluorosulfanylbenzoic acid (4.0 g) was dissolved in thionyl chloride (25 ml) while stirring and kept under reflux with exclusion of moisture for 10 h. After standing overnight, excess thionyl chloride was removed under reduced pressure at RT, and the resulting residue was dissolved in dichloromethane (50 ml) and admixed with N,O-dimethylhydroxylamine hydrochloride (1.25 g) and diethylisopropylamine (1.66 g) while stirring. After stirring at RT for 1 h, the mixture was concentrated under reduced pressure, and the residue was dissolved in ethyl acetate and washed 5 times with water. The organic phase was dried over magnesium sulfate, filtered and concentrated. The resulting crude product (4.2 g) was used directly in the next stage.

LC-MS rt: 1.50 min [M+H]$^{+}$: 337.0 c) 3-Amino-N-methoxy-N-methyl-5-pentafluorosulfanylbenzamide

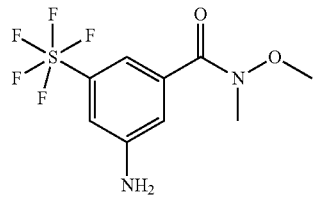

N-Methoxy-N-methyl-5-nitro-3-pentafluorosulfanylbenzamide (4.2 g) was dissolved in methanol (120 ml), and Raney nickel (approx. 700 mg) was added. With a hydrogen balloon attached, hydrogenation was effected on a magnetic stirrer. After 5 h, the catalyst was filtered off and washed with methanol. The filtrate was concentrated under reduced pressure and the residue was purified by means of preparative HPLC. The product-containing fractions were combined, freed of the acetonitrile, basified with sodium hydrogencarbonate solution and extracted three times with ethyl acetate. The combined extracts were dried over magnesium sulfate, filtered and concentrated. 1.73 g of the desired compound were obtained.

LC-MS rt: 1.27 min [M+H]$^{+}$: 307.0 d) 3-Acetylamino-N-methoxy-N-methyl-5-(pentafluorosulfanyl)benzamide

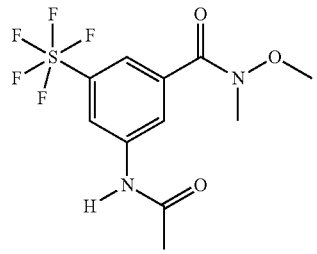

3-Amino-N-methoxy-N-methyl-5-pentafluorosulfanylbenzamide (1.2 g) was dissolved in methylene chloride (15 ml), and triethylamine (0.7 ml) followed by acetic anhydride (1.75 ml) were added while stirring with exclusion of moisture. After stirring at RT for 3 h, water and saturated sodium hydrogencarbonate solution were added, the phases were separated and the methylene chloride phase was washed three times more with water, dried over magnesium sulfate, filtered and concentrated. The resulting product (1.3 g) was used in the next stage without further purification.

LC-MS rt: 1.26 min [M+H]$^{+}$: 349.0 e) N-[3-Acetyl-5-(pentafluorosulfanyl)phenyl]acetamide

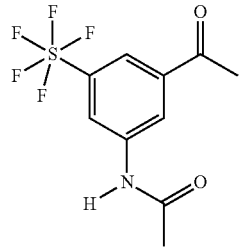

3-Acetylamino-N-methoxy-N-methyl-5-(pentafluorosulfanyl)benzamide (1.2 g) was dissolved in absolute THF (30 ml) and stirred at 0° C. with lithium hexamethyldisilazide (721 µl; density: 0.8 g/1; 23% in tent-butyl methyl ether) for 30 min. At 0° C., methylmagnesium bromide (2.87 ml, 3 M in diethyl ether) was then added dropwise while stirring. After stirring at RT for 2.5 h, further methylmagnesium bromide (1 ml, 3 M in diethyl ether) was added and the mixture was stirred again for 2.5 h. For workup, 1 N hydrochloric acid was added dropwise while cooling with ice, followed by water and ethyl acetate. The organic phase was removed and the water phase was extracted twice more with ethyl acetate. The combined ethyl acetate phases were dried over sodium sulfate, filtered and concentrated. The crude product (1.03 g) was combined with a crude product prepared in the same way (75 mg) and purified using silica gel with dichloromethane-methanol as the eluent. 860 mg of the desired compound were obtained. LC-MS rt: 1.34 min [M+H]$^+$: 304.0 f) N-[3-(2-Bromoacetyl)-5-(pentafluorosulfanyl)phenyl]acetamide

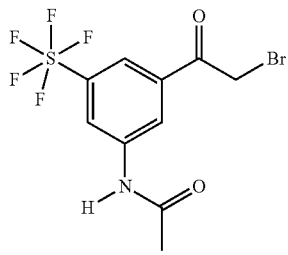

N-[3-Acetyl-5-(pentafluorosulfanyl)phenyl]acetamide (859 mg) was dissolved in a mixture of methanol (10 ml) and THF (10 ml) and phenyltrimethylammonium tribromide (1.065 g) was added in portions while stirring. After stirring at RT for 2 h, the mixture was heated to 40° C. for a further 3 h. After cooling, the reaction mixture was added to 2 N sulfuric acid and the aqueous phase was extracted 3 times with ethyl acetate. The combined extracts were dried over sodium sulfate, filtered and concentrated. The crude product was purified using silica gel with ethyl acetate/heptane as the eluent. 480 mg of the desired compound were obtained.

LC-MS rt: 1.47 min [M+H]$^+$: 382.0 g) 6-Chloro-[1,2,4]triazolo[4,3-b]pyridazin-3-ylamine as the hydrobromide and 6-chloro-[1,2,4]triazolo[4,3-b]pyridazin-3-ylamine

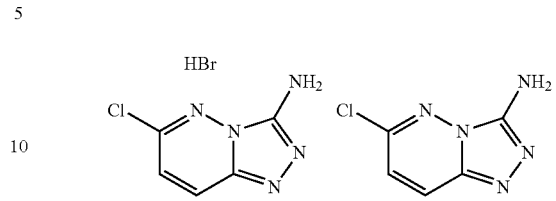

(6-Chloropyridazin-3-yl)hydrazine (1 g) was dissolved in a mixture of ethanol (22.5 ml) and water (9 ml) at RT while stirring. Thereafter, cyanogen bromide (2.8 ml, 5 M in acetonitrile) was added dropwise while stirring. After stirring for 6 h and leaving to stand overnight, the precipitate was filtered off with suction and dried. In this way, 1.14 g of the desired product were obtained.

LC-MS rt: 0.24 min [M+H]$^+$: 170.1

Further product was obtained in the form of the free base, by basifying the mother liquor with saturated potassium carbonate solution. The precipitate formed was filtered off with suction and dried (326 mg).

LC-MS rt: 0.24 min [M+H]$^+$: 170.1 h) 6-Ethoxy-[1,2,4]triazolo[4,3-b]pyridazin-3-ylamine

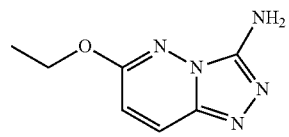

6-Chloro-[1,2,4]triazolo[4,3-b]pyridazin-3-ylamine (1.1 g) was taken up in a large amount of water and alkalized with saturated potassium carbonate solution. The solid which precipitated out was filtered off with suction and dried (388 mg). Repeated extraction of the mother liquor with dichloromethane, drying of the combined organic phases over sodium sulfate, filtration and concentration afforded a further 228 mg of product in total. The resulting free base (616 mg) was dissolved in absolute ethanol (40 ml) and admixed with solid sodium ethoxide (990 mg) in portions. After stirring at 55° C. for 2 h, water was added and the aqueous phase was extracted three times with dichloromethane. The combined extracts were dried over sodium sulfate, filtered and concentrated. 709 mg of the desired compound were obtained.

LC-MS rt: 0.51 min [M+H]$^+$: 180.1 i) 1-{2-[3-Acetylamino-5-(pentafluorosulfanyl)phenyl]-2-oxoethyl}-3-amino-6-ethoxy-[1,2,4]triazolo[4,3-b]pyridazin-1-ium trifluoroacetate 6-Ethoxy-[1,2,4]triazolo[4,3-b]pyridazin-3-ylamine (40 mg) was initially charged in absolute DMF (3.5 ml) while stirring, and N-[3-(2-bromoacetyl)-5-(pentafluorosulfanyl)-phenyl]acetamide, dissolved in absolute DMF (1.5 ml), was added dropwise. After stirring at RT for 5 h and leaving to stand overnight, the solvent was drawn off and the residue was purified by means of preparative HPLC, the 1-substituted compound sought eluting before the 2-substituted compound. The clean, product-containing fractions were combined, freed of the acetonitrile and freeze-dried. 13 mg of the desired compound were obtained. The fractions contaminated with the 2-substituted isomer were likewise combined, freed of the acetonitrile and freeze-dried. The residue was then purified using silica gel with a dichloromethane/methanol gradient, the 1-substituted compound sought eluting after the 2-substituted compound. The clean, product-containing fractions were combined and dried. The residue was taken up with acetonitrile and water, and freeze-dried. A further 20 mg of the desired compound were obtained.

LC-MS rt: 1.10 min [M+H]⁺: 481.0

Example 4

3-Amino-1-[2-(3-tert-butyl-4-methoxy-5-morpholin-4-ylphenyl)-2-oxoethyl]-6-trifluoromethyl-[1,2,4]triazolo[4,3-a]pyridin-1-ium trifluoroacetate

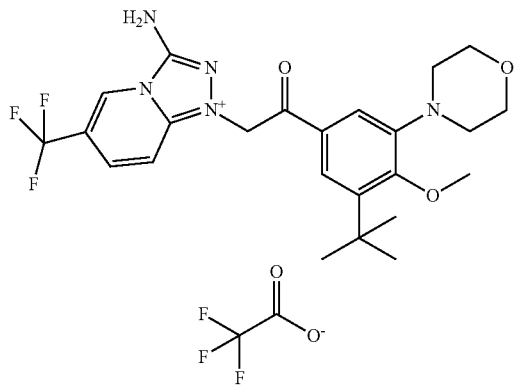

6-Trifluoromethyl-[1,2,4]triazolo[4,3-a]pyridin-3-ylamine hydrobromide (W1.301; 309 mg) was dissolved in a little water, alkalized with saturated potassium carbonate solution and extracted three times with EA. The combined EA phases were dried over magnesium sulfate, filtered and concentrated. 212 mg of the free base were obtained, which were dissolved in DMF (5 ml) while stirring at RT. Within 15 min, 2-bromo-1-(3-tert-butyl-4-methoxy-5-morpholin-4-ylphenyl)ethanone (O1.003; 427 mg dissolved in 1 ml of DMF) was added slowly. The mixture was stirred at RT for 7 h and then left to stand overnight. Subsequently, it was stirred at 40° C. for 2 h and at 60° C. for 3 h. Then the solvent was drawn off and the residue was purified by means of preparative HPLC. The fractions comprising the desired product were combined, freed of the ACN and freeze-dried. 90 mg of the title compound were obtained.

LC-MS rt: 1.34 min [M+H]⁺: 492.1

Further examples are detailed in the table below. They were carried out by couplings, carried out analogously to example 11) or example 4, of triazolopyridazinenes or -pyridines of the "W1." or "W2." type with the appropriate acetophenone derivatives of the "O1." type. The 2-alkylation product, which occurs with the same mass in the mass spectrum and is obtained as an impurity was removed by means of preparative HPLC, in which the desired 1-alkylation product normally eluted first under the conditions selected, while the 2-alkylation product eluted thereafter. Should a further separation using silica gel have been necessary (see example 1i), the sequence of elution was reversed using the DCM/methanol eluent mixture. The 2-alkylation product eluted first, the 1-alkylation product second.

| Example | Structure | Name | LC-MS rt [min] | [M]⁺ or [M + H]⁺ |
|---|---|---|---|---|
| Ex.: 002 | 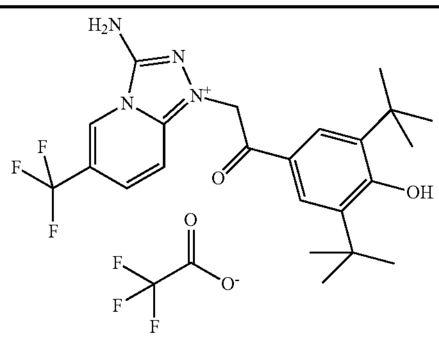 | 3-Amino-1-[2-(3,5-di-tert-butyl-4-hydroxyphenyl)-2-oxoethyl]-6-trifluoromethyl-[1,2,4]triazolo[4,3-a]pyridin-1-ium trifluoroacetate | 1.38 | 449.1 (met. a) |
| Ex.: 003 | 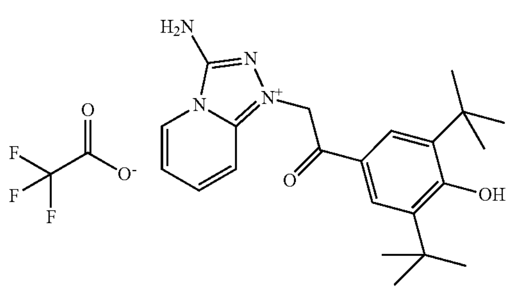 | 3-Amino-1-[2-(3,5-di-tert-butyl-4-hydroxyphenyl)-2-oxoethyl]-[1,2,4]triazolo[4,3-a]pyridin-1-ium trifluoroacetate | 1.23 | 381.2 (met. a) |

| Example | Structure | Name | LC-MS rt [min] | [M]+ or [M + H]+ |
|---|---|---|---|---|
| Ex.: 004 | 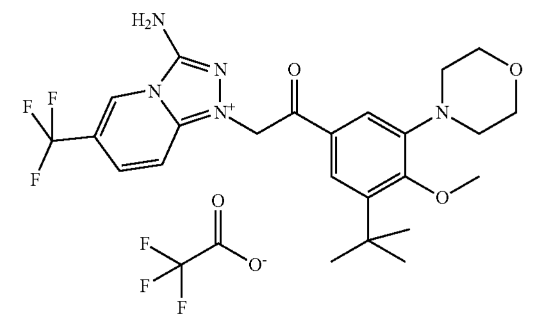 | 3-Amino-1-[2-(3-tert-butyl-4-methoxy-5-morpholin-4-ylphenyl)-2-oxoethyl]-6-trifluoromethyl-[1,2,4]triazolo[4,3-a]pyridin-1-ium trifluoroacetate | 1.34 | 492.1 (met. a) |
| Ex.: 005 | 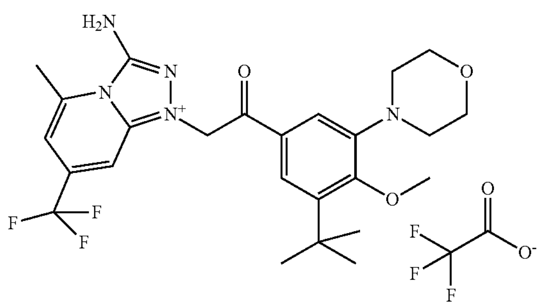 | 3-Amino-1-[2-(3-tert-butyl-4-methoxy-5-morpholin-4-ylphenyl)-2-oxoethyl]-5-methyl-7-trifluoromethyl-[1,2,4]triazolo[4,3-a]pyridin-1-ium trifluoroacetate | 1.38 | 506.2 (met. a) |
| Ex.: 006 | 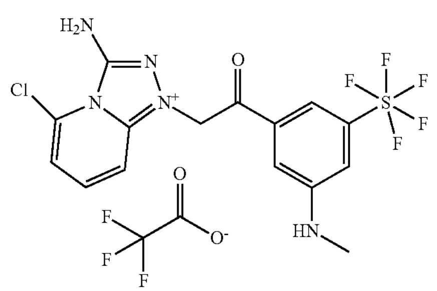 | 3-Amino-5-chloro-1-{2-[3-methylamino-5-(pentafluorosulfanyl)phenyl]-2-oxoethyl}-[1,2,4]triazolo[4,3-a]pyridin-1-ium trifluoroacetate | 1.14 | 442.0 (met. a) |
| Ex.: 007 | 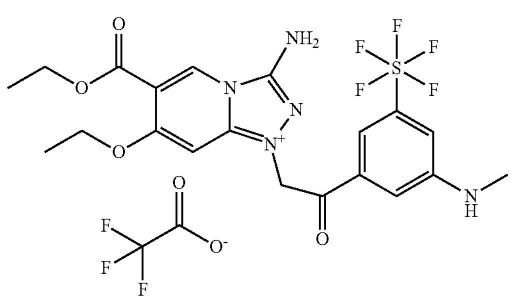 | 3-Amino-7-ethoxy-6-ethoxycarbonyl-1-{2-[3-methylamino-5-(pentafluorosulfanyl)phenyl]-2-oxoethyl}-[1,2,4]triazolo[4,3-a]pyridin-1-ium trifluoroacetate | 1.30 | 524.2 (met. a) |
| Ex.: 008 | 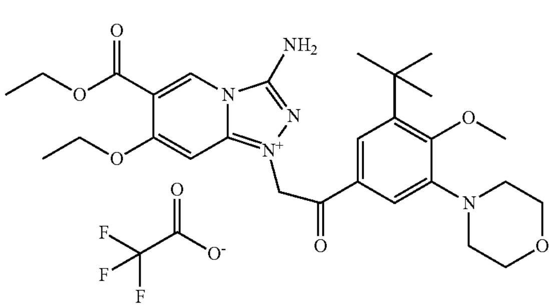 | 3-Amino-1-[2-(3-tert-butyl-4-methoxy-5-morpholin-4-yl-phenyl)-2-oxoethyl]-7-ethoxy-6-ethoxycarbonyl-[1,2,4]triazolo[4,3-a]pyridin-1-ium trifluoroacetate | 1.36 | 540.3 (met. a) |

-continued

| Example | Structure | Name | LC-MS rt [min] | [M]+ or [M + H]+ |
|---|---|---|---|---|
| Ex.: 009 | 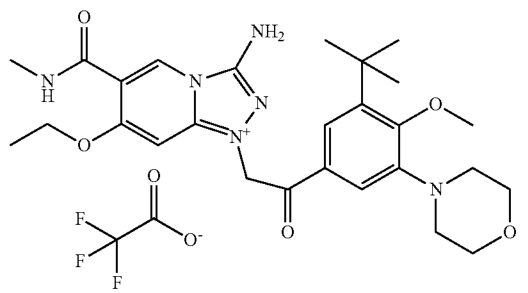 | 3-Amino-1-[2-(3-tert-butyl-4-methoxy-5-morpholin-4-yl-phenyl)-2-oxoethyl]-7-ethoxy-6-methylcarbamoyl-[1,2,4]triazolo[4,3-a]pyridin-1-ium trifluoroacetate | 1.28 | 525.3 (met. a) |
| Ex.: 010 | 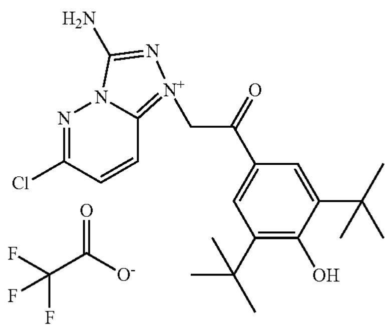 | 3-Amino-6-chloro-1-[2-(3,5-di-tert-butyl-4-hydroxyphenyl)-2-oxoethyl]-[1,2,4]triazolo[4,3-b]pyridazin-1-ium trifluoroacetate | 1.26 | 416.1 (met. a) |
| Ex.: 011 | 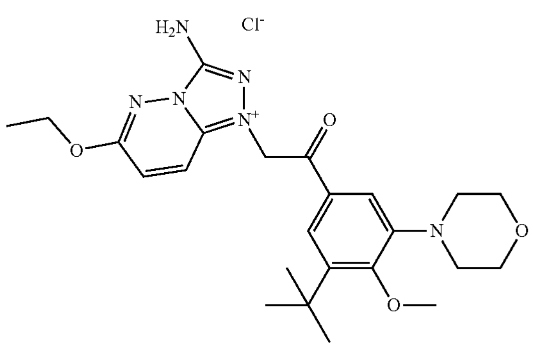 | 3-Amino-1-[2-(3-tert-butyl-4-methoxy-5-morpholin-4-ylphenyl)-2-oxoethyl]-6-ethoxy-[1,2,4]triazolo[4,3-b]pyridazin-1-ium chloride | 1.32 | 469.2 (met. a) |
| Ex.: 012 | 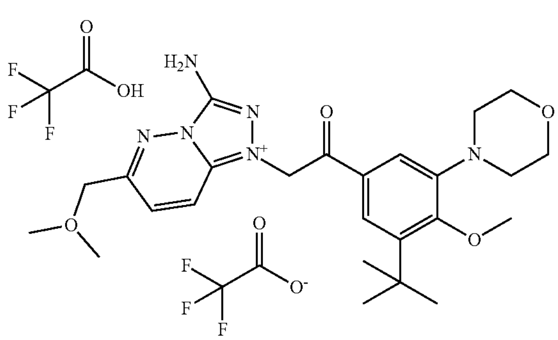 | 3-Amino-1-[2-(3-tert-butyl-4-methoxy-5-morpholin-4-yl-phenyl)-2-oxoethyl]-6-isopropoxy-[1,2,4]triazolo[4,3-b]pyridazin-1-ium trifluoroacetate | 1.35 | 483.3 (met. a) |

-continued

| Example | Structure | Name | LC-MS rt [min] | [M]⁺ or [M + H]⁺ |
|---|---|---|---|---|
| Ex.: 013 | 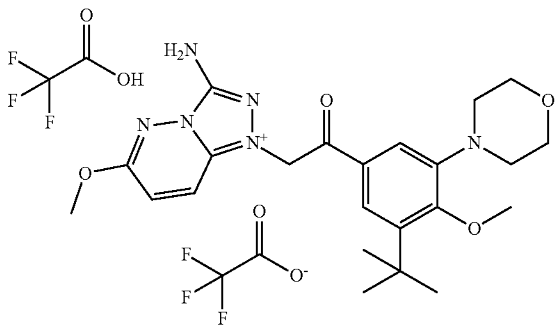 | 3-Amino-1-[2-(3-tert-butyl-4-methoxy-5-morpholin-4-ylphenyl)-2-oxoethyl]-6-methoxy-[1,2,4]triazolo[4,3-b]pyridazin-1-ium trifluoroacetate | 1.24 | 455.1 (met. a) |
| Ex.: 014 | 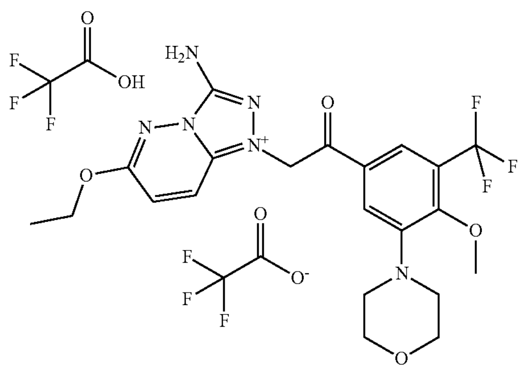 | 3-Amino-6-ethoxy-1-[2-(4-methoxy-3-morpholin-4-yl-5-trifluoromethylphenyl)-2-oxoethyl]-[1,2,4]triazolo[4,3-b]pyridazin-1-ium trifluoroacetate | 1.17 | 481.1 (met. a) |
| Ex.: 015 | 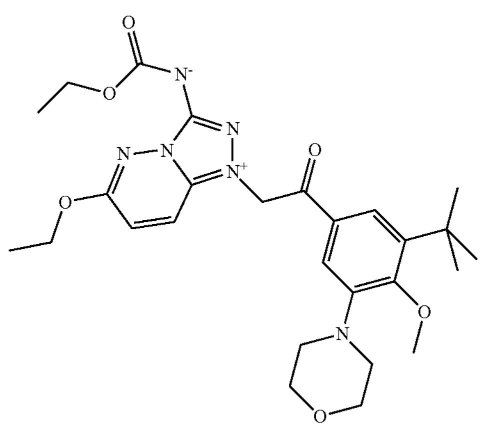 | 1-[2-(3-tert-butyl-4-methoxy-5-morpholin-4-ylphenyl)-2-oxoethyl]-6-ethoxy-3-ethoxycarbonylamino-[1,2,4]triazolo[4,3-b]pyridazin-1-ium | 1.34 | 541.3 (met. a) |
| Ex.: 016 | 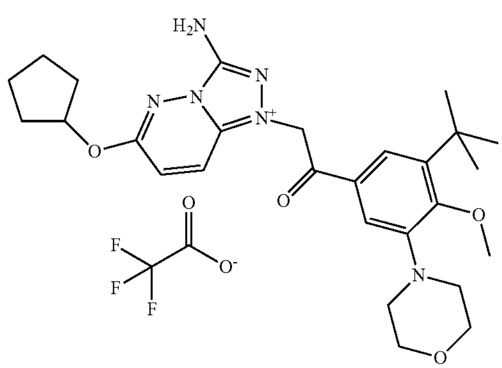 | 3-Amino-1-[2-(3-tert-butyl-4-methoxy-5-morpholin-4-yl-phenyl)-2-oxoethyl]-6-cyclopentyloxy-[1,2,4]triazolo[4,3-b]pyridazin-1-ium trifluoroacetate | 1.42 | 509.2 (met. a) |

-continued

| Example | Structure | Name | LC-MS rt [min] | [M]+ or [M + H]+ |
|---|---|---|---|---|
| Ex.: 017 | 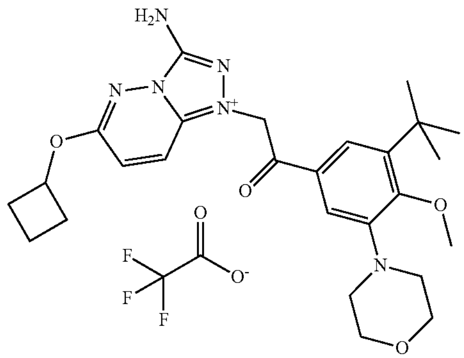 | 3-Amino-1-[2-(3-tert-butyl-4-methoxy-5-morpholin-4-yl-phenyl)-2-oxoethyl]-6-cyclobutoxy-[1,2,4]triazolo[4,3-b]pyridazin-1-ium trifluoroacetate | 1.36 | 495.2 (met. a) |
| Ex.: 018 | 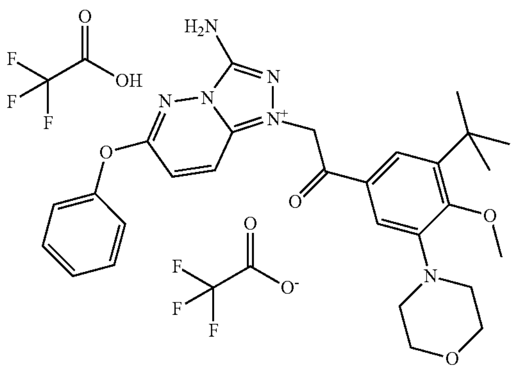 | 3-Amino-1-[2-(3-tert-butyl-4-methoxy-5-morpholin-4-yl-phenyl)-2-oxoethyl]-6-phenoxy-[1,2,4]triazolo[4,3-b]pyridazin-1-ium trifluoroacetate | 1.34 | 517.3 (met. a) |
| Ex.: 019 | 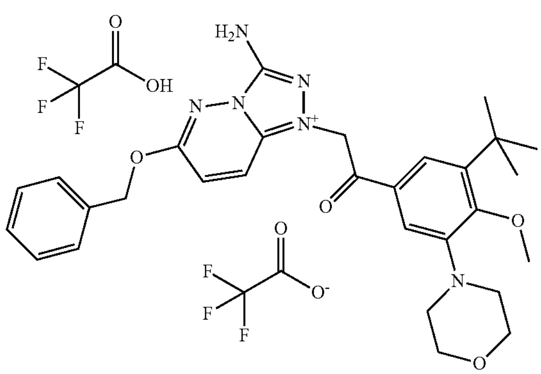 | 3-Amino-6-benzyloxy-1-[2-(3-tert-butyl-4-methoxy-5-morpholin-4-ylphenyl)-2-oxoethyl]-[1,2,4]triazolo[4,3-b]pyridazin-1-ium trifluoroacetate | 1.39 | 531.2 (met. a) |
| Ex.: 020 | 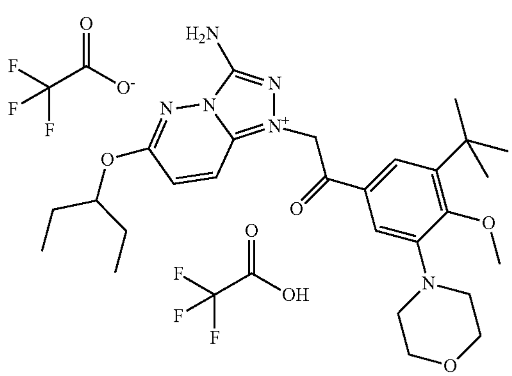 | 3-Amino-1-[2-(3-tert-butyl-4-methoxy-5-morpholin-4-ylphenyl)-2-oxoethyl]-6-(1-ethyl-propoxy)-[1,2,4]triazolo[4,3-b]pyridazin-1-ium trifluoroacetate | 1.46 | 511.2 (met. a) |

-continued

| Example | Structure | Name | LC-MS rt [min] | [M]+ or [M + H]+ |
|---|---|---|---|---|
| Ex.: 021 | 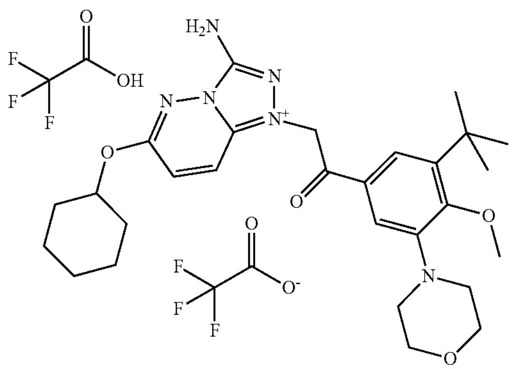 | 3-Amino-1-[2-(3-tert-butyl-4-methoxy-5-morpholin-4-ylphenyl)-2-oxoethyl]-6-cyclohexyloxy-[1,2,4]triazolo[4,3-b]pyridazin-1-ium trifluoroacetate | 1.44 | 523.2 (met. a) |
| Ex.: 022 | 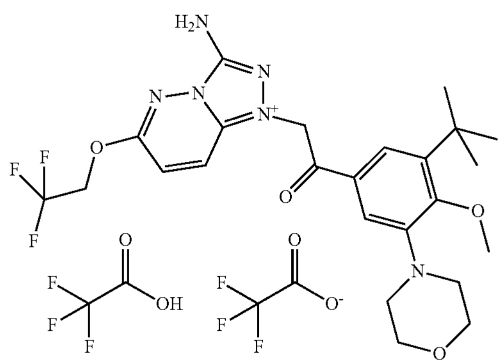 | 3-Amino-1-[2-(3-tert-butyl-4-methoxy-5-morpholin-4-yl-phenyl)-2-oxoethyl]-6-(2,2,2-trifluoroethoxy)-[1,2,4]triazolo[4,3-b]pyridazin-1-ium trifluoroacetate | 1.32 | 523.2 (met. a) |
| Ex.: 023 | 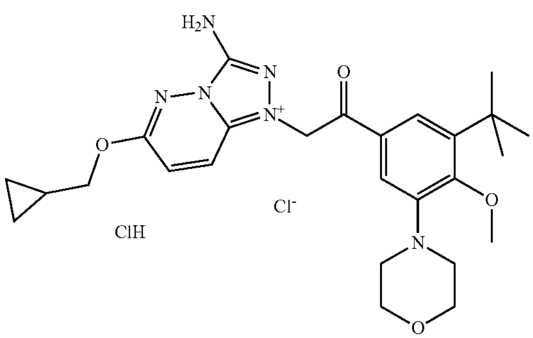 | 3-Amino-1-[2-(3-tert-butyl-4-methoxy-5-morpholin-4-yl-phenyl)-2-oxoethyl]-6-cyclopropylmethoxy-[1,2,4]triazolo[4,3-b]pyridazin-1-ium chloride hydrochloride | 1.35 | 495.1 (met. a) |
| Ex.: 024 | 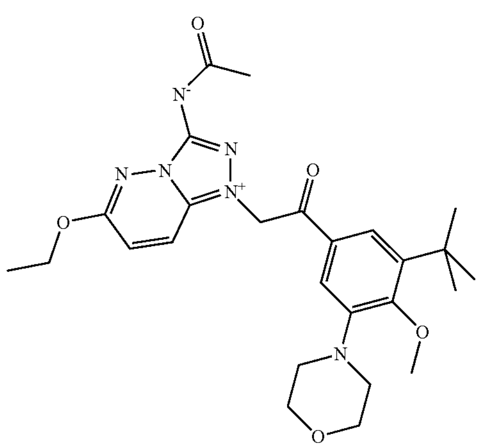 | 3-Acetylamino-1-[2-(3-tert-butyl-4-methoxy-5-morpholin-4-yl-phenyl)-2-oxoethyl]-6-ethoxy-[1,2,4]triazolo[4,3-b]pyridazin-1-ium | 1.27 | 511.4 (met. a) |

-continued

| Example | Structure | Name | LC-MS rt [min] | [M]+ or [M + H]+ |
|---|---|---|---|---|
| Ex.: 025 | 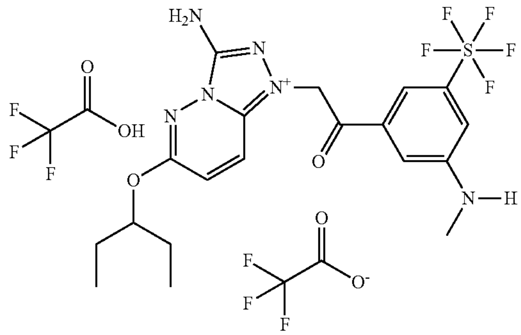 | 3-Amino-6-(1-ethylpropoxy)-1-{2-[3-methylamino-5-(pentafluorosulfanyl)phenyl]-2-oxoethyl}-[1,2,4]triazolo[4,3-b]pyridazin-1-ium trifluoroacetate | 1.32 | 495.1 (met. a) |
| Ex.: 026 | 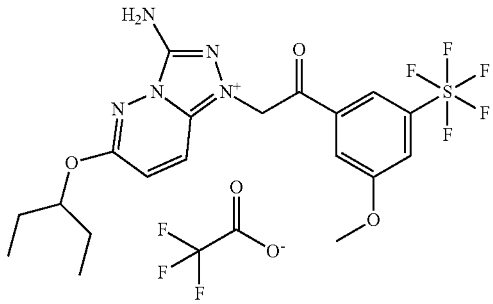 | 3-Amino-6-(1-ethylpropoxy)-1-{2-[3-methoxy-5-(pentafluorosulfanyl)phenyl]-2-oxoethyl}-[1,2,4]triazolo[4,3-b]pyridazin-1-ium trifluoroacetate | 1.35 | 496.1 (met. a) |
| Ex.: 027 | 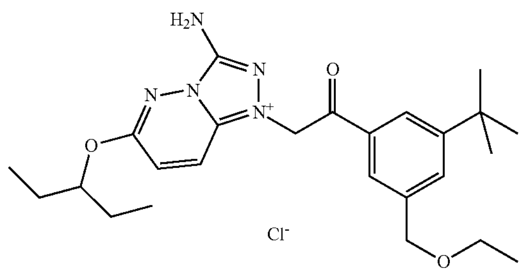 | 3-Amino-1-[2-(3-tert-butyl-5-ethoxymethylphenyl)-2-oxoethyl]-6-(1-ethylpropoxy)-[1,2,4]triazolo[4,3-b]pyridazin-1-ium chloride | 0.91 | 454.3 (met. b) |
| Ex.: 028 | 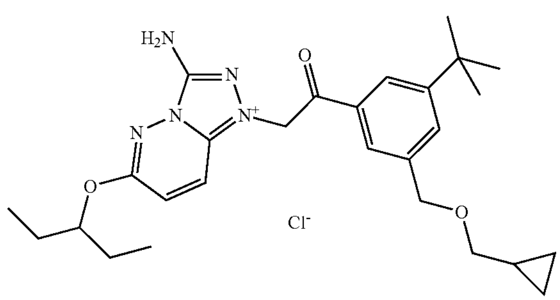 | 3-Amino-1-[2-(3-tert-butyl-5-cyclopropylmethoxymethyl-phenyl)-2-oxoethyl]-6-(1-ethylpropoxy)-[1,2,4]triazolo[4,3-b]pyridazin-1-ium chloride | 1.51 | 480.1 (met. a) |
| Ex.: 029 | 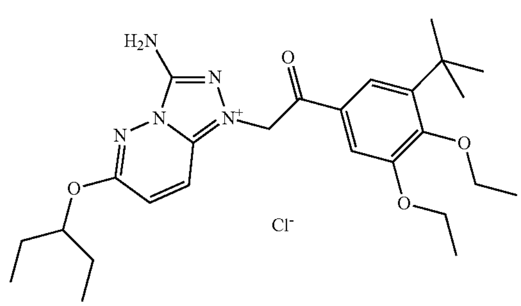 | 3-Amino-1-[2-(3-tert-butyl-4,5-diethoxyphenyl)-2-oxoethyl]-6-(1-ethylpropoxy)-[1,2,4]triazolo[4,3-b]pyridazin-1-ium chloride | 1.58 | 484.1 (met. a) |

-continued

| Example | Structure | Name | LC-MS rt [min] | [M]+ or [M + H]+ |
|---|---|---|---|---|
| Ex.: 030 | 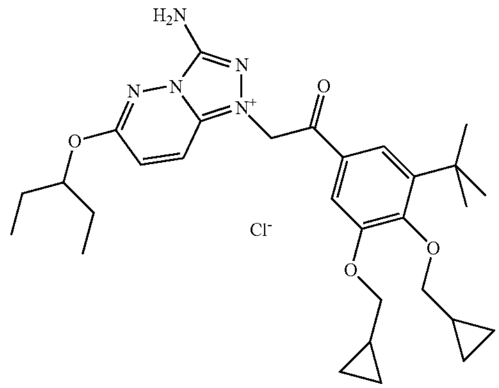 | 3-Amino-1-[2-(3-tert-butyl-4,5-bis-cyclopropylmethoxyphenyl)-2-oxoethyl]-6-(1-ethylpropoxy)-[1,2,4]triazolo[4,3-b]pyridazin-1-ium chloride | 1.64 | 536.5 (met. a) |
| Ex.: 031 | 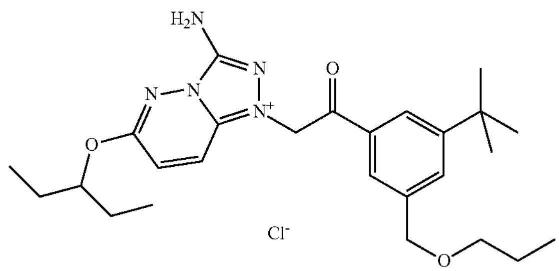 | 3-Amino-1-[2-(3-tert-butyl-5-propoxymethylphenyl)-2-oxoethyl]-6-(1-ethylpropoxy)-[1,2,4]triazolo[4,3-b]pyridazin-1-ium chloride | 0.94 | 468.2 (met. b) |
| Ex.: 032 | 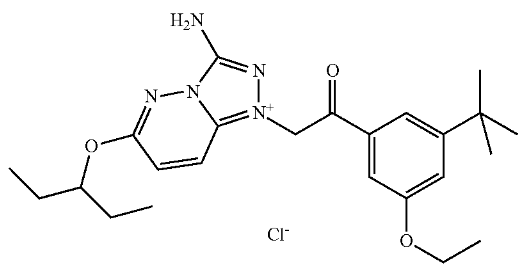 | 3-Amino-1-[2-(3-tert-butyl-5-ethoxyphenyl)-2-oxoethyl]-6-(1-ethylpropoxy)-[1,2,4]triazolo[4,3-b]pyridazin-1-ium chloride | 0.92 | 440.2 (met. b) |
| Ex.: 033 | 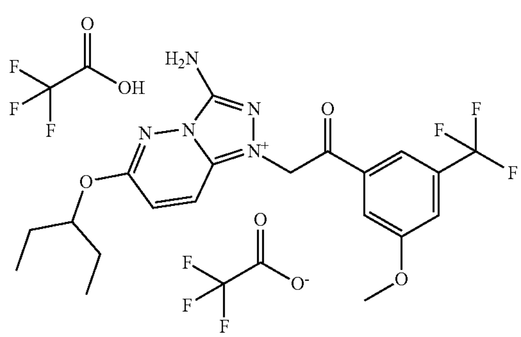 | 3-Amino-6-(1-ethylpropoxy)-1-[2-(3-methoxy-5-trifluoromethylphenyl)-2-oxoethyl]-[1,2,4]triazolo[4,3-b]pyridazin-1-ium trifluoroacetate | 1.31 | 438.1 (met. a) |
| Ex.: 034 | 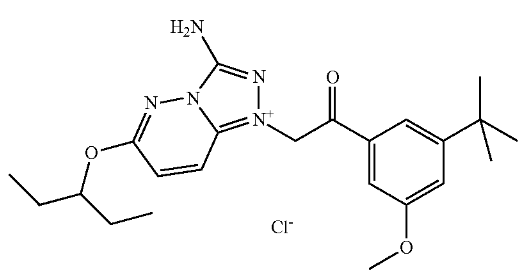 | 3-Amino-1-[2-(3-tert-butyl-5-methoxyphenyl)-2-oxoethyl]-6-(1-ethylpropoxy)-[1,2,4]triazolo[4,3-b]pyridazin-1-ium chloride | 0.89 | 426.2 (met. b) |

-continued

| Example | Structure | Name | LC-MS rt [min] | [M]⁺ or [M + H]⁺ |
|---|---|---|---|---|
| Ex.: 035 | 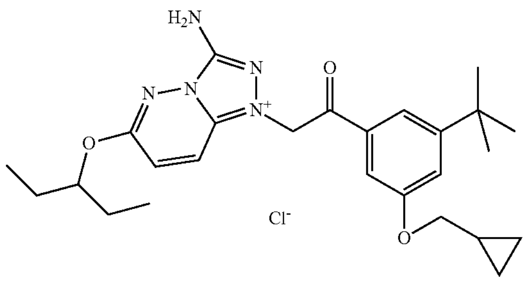 | 3-Amino-1-[2-(3-tert-butyl-5-cyclopropylmethoxyphenyl)-2-oxoethyl]-6-(1-ethylpropoxy)-[1,2,4]triazolo[4,3-b]pyridazin-1-ium chloride | 0.95 | 466.3 (met. b) |
| Ex.: 036 | 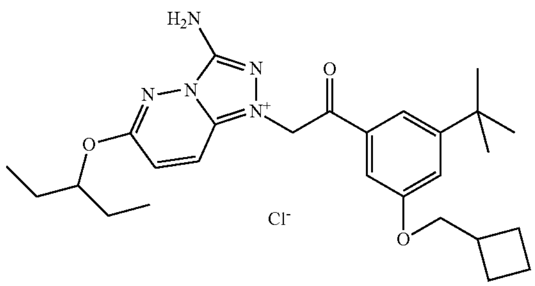 | 3-Amino-1-[2-(3-tert-butyl-5-cyclobutylmethoxyphenyl)-2-oxoethyl]-6-(1-ethylpropoxy)-[1,2,4]triazolo[4,3-b]pyridazin-1-ium chloride | 0.99 | 480.2 (met. b) |
| Ex.: 037 | 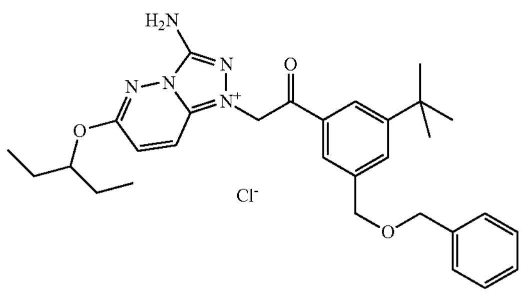 | 3-Amino-1-[2-(3-benzyloxymethyl-5-tert-butylphenyl)-2-oxoethyl]-6-(1-ethylpropoxy)-[1,2,4]triazolo[4,3-b]pyridazin-1-ium chloride | 0.97 | 516.3 (met. b) |
| Ex.: 038 | 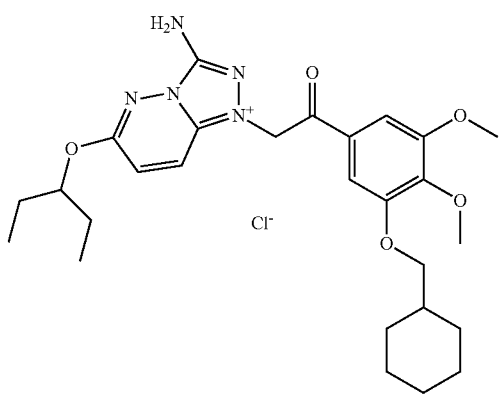 | 3-Amino-1-[2-(3-cyclohexylmethoxy-4,5-dimethoxyphenyl)-2-oxoethyl]-6-(1-ethylpropoxy)-[1,2,4]triazolo[4,3-b]pyridazin-1-ium chloride | 1.49 | 512.5 (met. a) |
| Ex.: 039 | 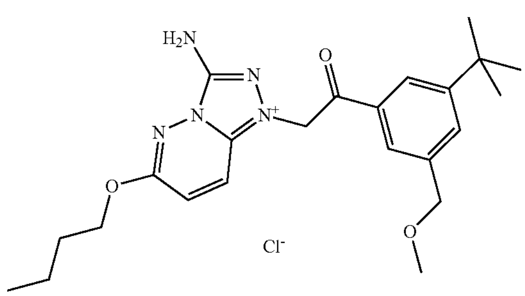 | 3-Amino-6-butoxy-1-[2-(3-tert-butyl-5-methoxymethylphenyl)-2-oxoethyl]-[1,2,4]triazolo[4,3-b]pyridazin-1-ium chloride | 1.31 | 426.3 (met. a) |

-continued

| Example | Structure | Name | LC-MS rt [min] | [M]+ or [M + H]+ |
|---|---|---|---|---|
| Ex.: 040 | 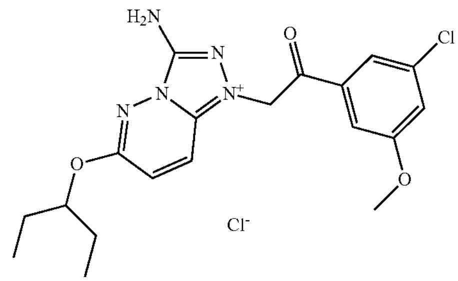 | 3-Amino-1-[2-(3-chloro-5-methoxyphenyl)-2-oxoethyl]-6-(1-ethylpropoxy)-[1,2,4]triazolo[4,3-b]pyridazin-1-ium chloride | 1.25 | 404.2 (met. a) |
| Ex.: 041 | 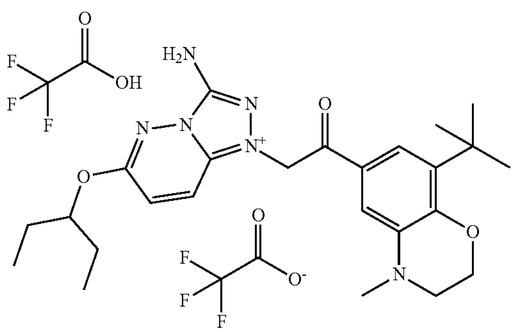 | 3-Amino-1-[2-(8-tert-butyl-4-methyl-3,4-dihydro-2H-benzo[1,4]oxazin-6-yl)-2-oxoethyl]-6-(1-ethylpropoxy)-[1,2,4]triazolo[4,3-b]pyridazin-1-ium trifluoroacetate | 1.41 | 467.3 (met. a) |
| Ex.: 042 | 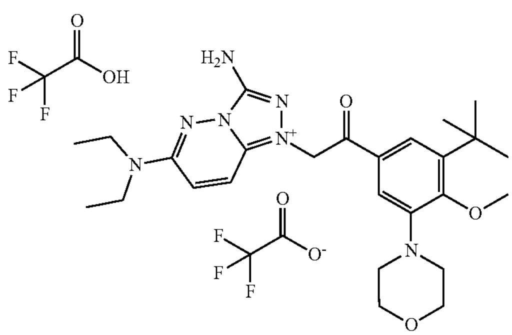 | 3-Amino-1-[2-(3-tert-butyl-4-methoxy-5-morpholin-4-ylphenyl)-2-oxoethyl]-6-diethylamino-[1,2,4]triazolo[4,3-b]pyridazin-1-ium trifluoroacetate | 1.42 | 496.4 (met. a) |
| Ex.: 043 | 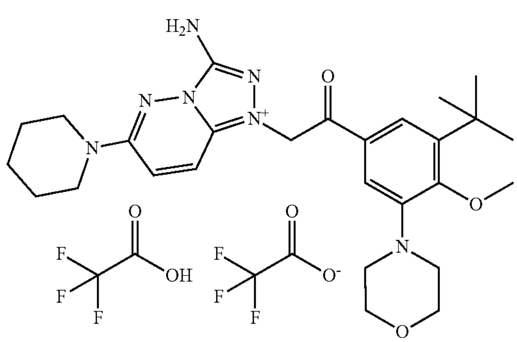 | 3-Amino-1-[2-(3-tert-butyl-4-methoxy-5-morpholin-4-ylphenyl)-2-oxoethyl]-6-piperidin-1-yl-[1,2,4]triazolo[4,3-b]pyridazin-1-ium trifluoroacetate | 1.35 | 508.3 (met. a) |

-continued

| Example | Structure | Name | LC-MS rt [min] | [M]+ or [M + H]+ |
|---|---|---|---|---|
| Ex.: 044 | 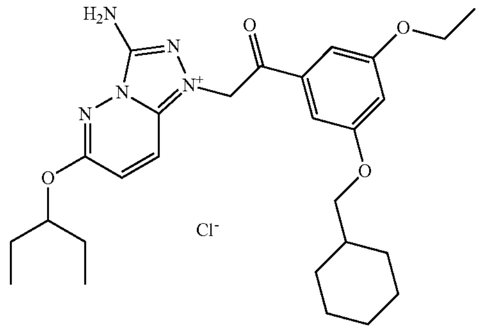 | 3-Amino-1-[2-(3-cyclohexylmethoxy-5-ethoxyphenyl)-2-oxoethyl]-6-(1-ethylpropoxy)-[1,2,4]triazolo[4,3-b]pyridazin-1-ium chloride | 1.00 | 496.3 (met. b) |
| Ex.: 045 | 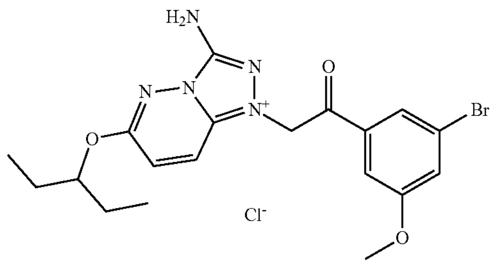 | 3-Amino-1-[2-(3-bromo-5-methoxyphenyl)-2-oxoethyl]-6-(1-ethylpropoxy)-[1,2,4]triazolo[4,3-b]pyridazin-1-ium chloride | 0.82 | 448.1 (met. b) |
| Ex.: 046 | 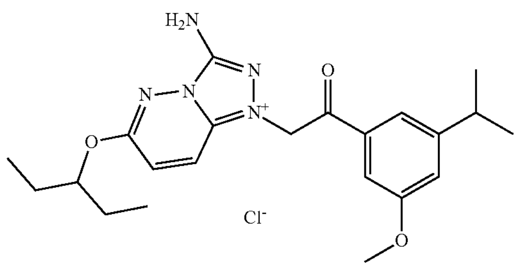 | 3-Amino-6-(1-ethylpropoxy)-1-[2-(3-isopropyl-5-methoxyphenyl)-2-oxoethyl]-[1,2,4]triazolo[4,3-b]pyridazin-1-ium chloride | 0.86 | 412.5 (met. b) |
| Ex.: 047 | 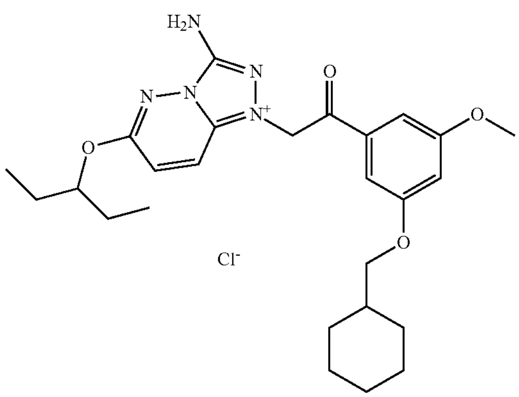 | 3-Amino-1-[2-(3-cyclohexylmethoxy-5-methoxyphenyl)-2-oxoethyl]-6-(1-ethylpropoxy)-[1,2,4]triazolo[4,3-b]pyridazin-1-ium chloride | 0.98 | 482.2 (met. b) |
| Ex.: 048 | 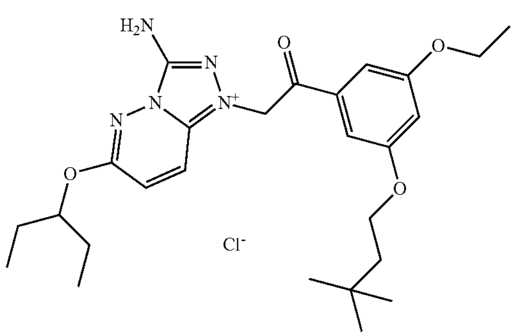 | 3-Amino-1-{2-[3-(3,3-dimethylbutoxy)-5-ethoxyphenyl]-2-oxoethyl}-6-(1-ethylpropoxy)-[1,2,4]triazolo[4,3-b]pyridazin-1-ium chloride | 1.54 | 484.4 (met. a) |

-continued

| Example | Structure | Name | LC-MS rt [min] | [M]+ or [M + H]+ |
|---|---|---|---|---|
| Ex.: 049 | 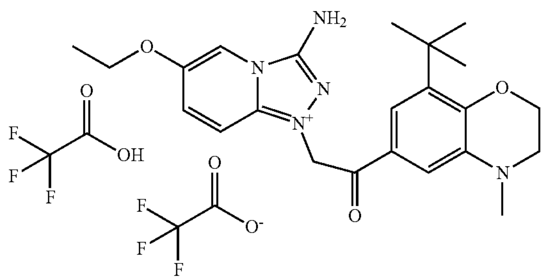 | 3-Amino-1-[2-(8-tert-butyl-4-methyl-3,4-dihydro-2H-benzo[1,4]oxazin-6-yl)-2-oxoethyl]-6-ethoxy-[1,2,4]triazolo[4,3-a]pyridin-1-ium trifluoroacetate | 1.22 | 424.2 (met. a) |
| Ex.: 050 | 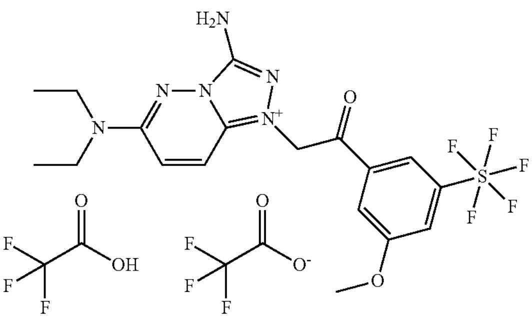 | 3-Amino-6-diethylamino-1-{2-[3-methoxy-5-(pentafluorosulfanyl)-phenyl]-2-oxoethyl}-[1,2,4]triazolo[4,3-b]pyridazin-1-ium trifluoroacetate | 1.27 | 481.1 (met. a) |
| Ex.: 051 | 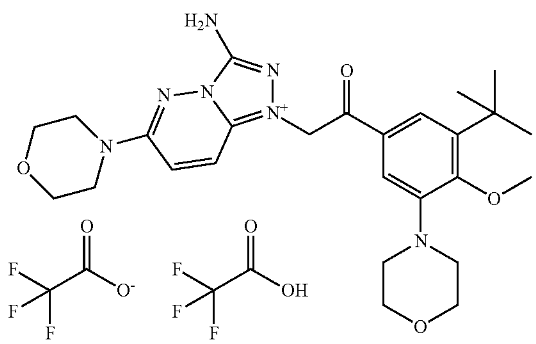 | 3-Amino-1-[2-(3-tert-butyl-4-methoxy-5-mopholin-4-ylphenyl)-2-oxoethyl]-6-morpholin-4-yl-[1,2,4]triazolo[4,3-b]pyridazin-1-ium trifluoroacetate | 1.22 | 510.2 (met. a) |
| Ex.: 052 | 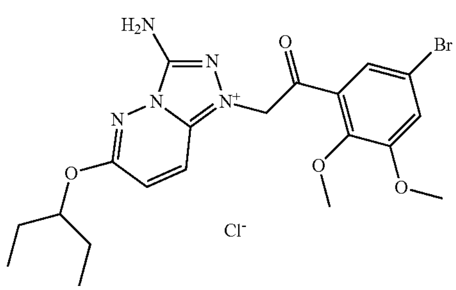 | 3-Amino-1-[2-(5-bromo-2,3-dimethoxyphenyl)-2-oxoethyl]-6-(1-ethylpropoxy)-[1,2,4]triazolo[4,3-b]pyridazin-1-ium chloride | 1.32 | 478.2 (met. a) |
| Ex.: 053 | 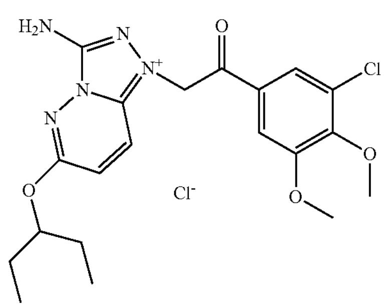 | 3-Amino-1-[2-(3-chloro-4,5-dimethoxyphenyl)-2-oxoethyl]-6-(1-ethylpropoxy)-[1,2,4]triazolo[4,3-b]pyridazin-1-ium chloride | 1.29 | 434.1 (met. a) |

-continued

| Example | Structure | Name | LC-MS rt [min] | [M]+ or [M + H]+ |
|---|---|---|---|---|
| Ex.: 054 | 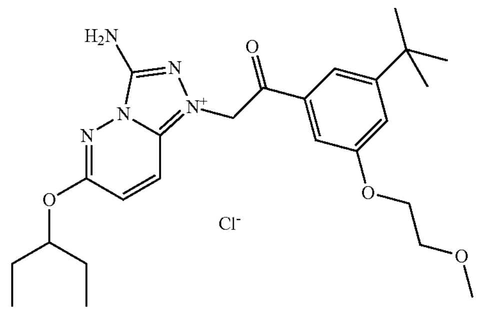 | 3-Amino-1-{2-[3-tert-butyl-5-(2-methoxyethoxy)phenyl]-2-oxoethyl}-6-(1-ethylpropoxy)-[1,2,4]triazolo[4,3-b]pyridazin-1-ium chloride | 1.40 | 470.3 (met. a) |
| Ex.: 055 | 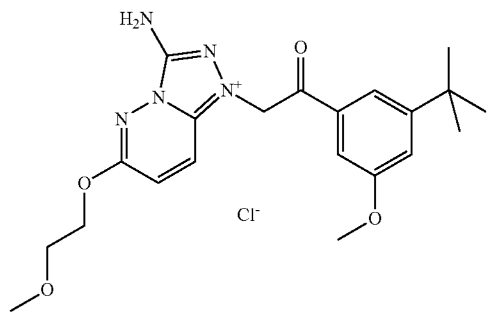 | 3-Amino-1-[2-(3-tert-butyl-5-methoxyphenyl)-2-oxoethyl]-6-(2-methoxyethoxy)-[1,2,4]triazolo[4,3-b]pyridazin-1-ium chloride | 0.78 | 414.2 (met. b) |
| Ex.: 056 | 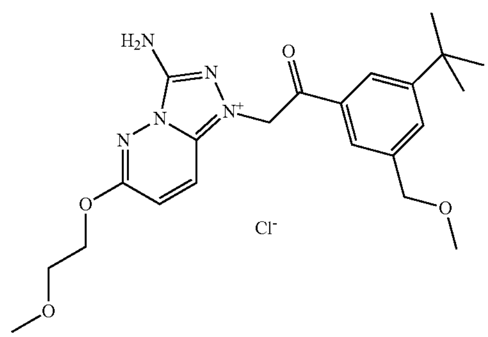 | 3-Amino-1-[2-(3-tert-butyl-5-methoxymethylphenyl)-2-oxoethyl]-6-(2-methoxyethoxy)-[1,2,4]triazolo[4,3-b]pyridazin-1-ium chloride | 1.19 | 428.3 (met. a) |
| Ex.: 057 | 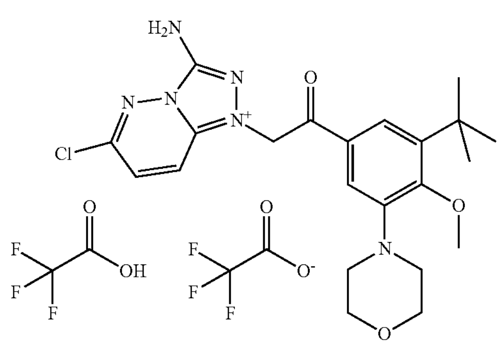 | 3-Amino-1-[2-(3-tert-butyl-4-methoxy-5-morpholin-4-ylphenyl)-2-oxoethyl]-6-chloro-[1,2,4]triazolo[4,3-b]pyridazin-1-ium trifluoroacetate | 1.45 | 459.2 (met. a) |

| Example | Structure | Name | LC-MS rt [min] | [M]+ or [M + H]+ |
|---|---|---|---|---|
| Ex.: 058 | 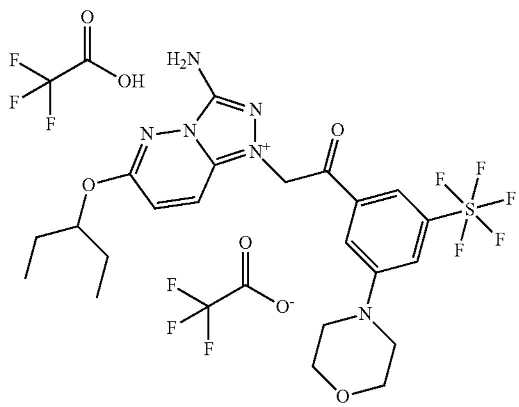 | 3-Amino-6-(1-ethylpropoxy)-1-{2-[3-morpholin-4-yl-5-(pentafluorosulfanyl)phenyl]-2-oxoethyl}-[1,2,4]triazolo[4,3-b]pyridazin-1-ium trifluoroacetate | 1.33 | 551.2 (met. a) |
| Ex.: 059 | 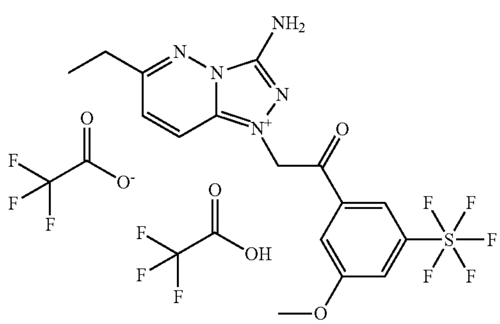 | 3-Amino-6-ethyl-1-{2-[3-methoxy-5-(pentafluorosulfanyl)phenyl]-2-oxoethyl}-[1,2,4]triazolo[4,3-b]pyridazin-1-ium trifluoroacetate | 1.16 | 438.0 (met. a) |
| Ex.: 060 | 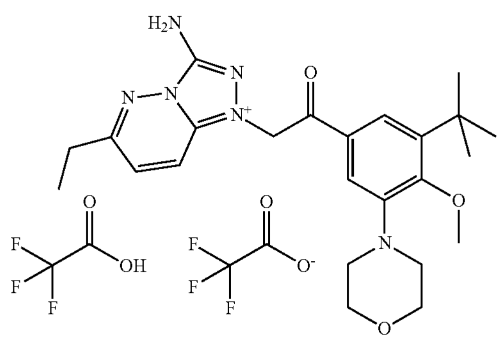 | 3-Amino-1-[2-(3-tert-butyl-4-methoxy-5-morpholin-4-ylphenyl)-2-oxoethyl]-6-ethyl-[1,2,4]triazolo[4,3-b]pyridazin-1-ium trifluoroacetate | 1.24 | 453.3 (met. a) |
| Ex.: 061 | 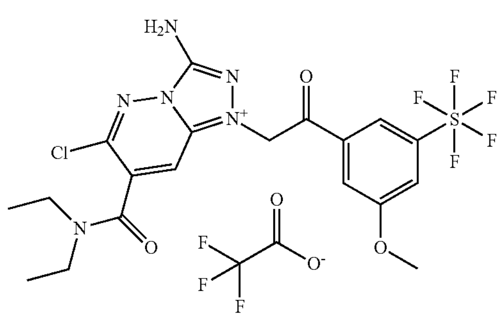 | 3-Amino-6-chloro-7-diethylcarbamoyl-1-{2-[3-methoxy-5-(pentafluorosulfanyl)phenyl]-2-oxoethyl}-[1,2,4]triazolo[4,3-b]pyridazin-1-ium trifluoroacetate | 1.46 | 543.1 (met. a) |

-continued

| Example | Structure | Name | LC-MS rt [min] | [M]+ or [M + H]+ |
|---|---|---|---|---|
| Ex.: 062 | 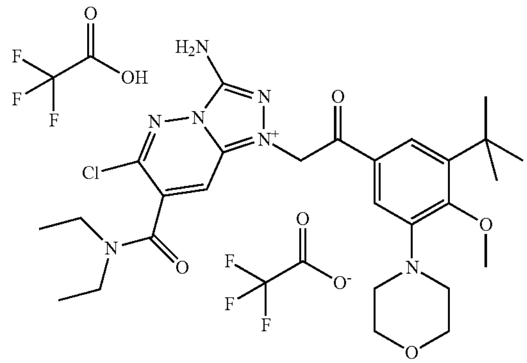 | 3-Amino-1-[2-(3-tert-butyl-4-methoxy-5-morpholin-4-ylphenyl)-2-oxoethyl]-6-chloro-7-diethylcarbamoyl-[1,2,4]triazolo[4,3-b]pyridazin-1-ium trifluoroacetate | 1.55 | 558.3 (met. a) |
| Ex.: 063 | 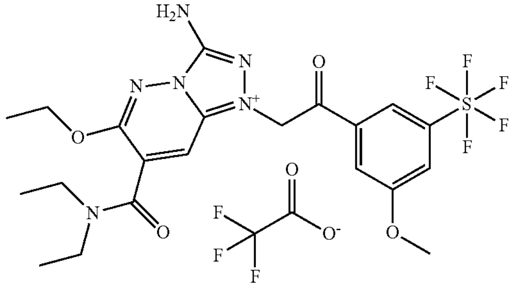 | 3-Amino-7-diethylcarbamoyl-6-ethoxy-1-{2-[3-methoxy-5-(pentafluorosulfanyl)phenyl]-2-oxoethyl}-[1,2,4]triazolo[4,3-b]pyridazin-1-ium trifluoroacetate | 1.24 | 553.2 (met. a) |
| Ex.: 064 | 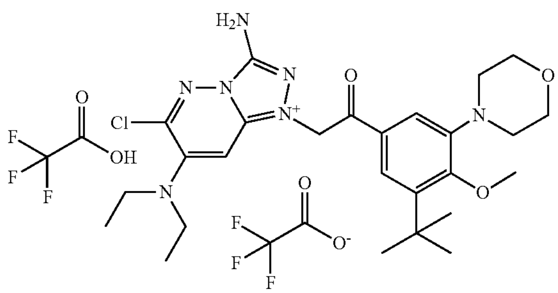 | 3-Amino-1-[2-(3-tert-butyl-4-methoxy-5-morpholin-4-ylphenyl)-2-oxoethyl]-6-chloro-7-diethylamino-[1,2,4]triazolo[4,3-b]pyridazin-1-ium trifluoroacetate | 1.37 | 530.2 (met. a) |
| Ex.: 065 | 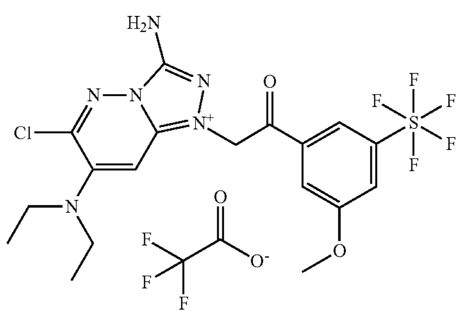 | 3-Amino-6-chloro-7-diethylamino-1-{2-[3-methoxy-5-(pentafluorosulfanyl)phenyl]-2-oxoethyl}-[1,2,4]triazolo[4,3-b]pyridazin-1-ium trifluoroacetate | 1.28 | 515.0 (met. a) |
| Ex.: 066 | 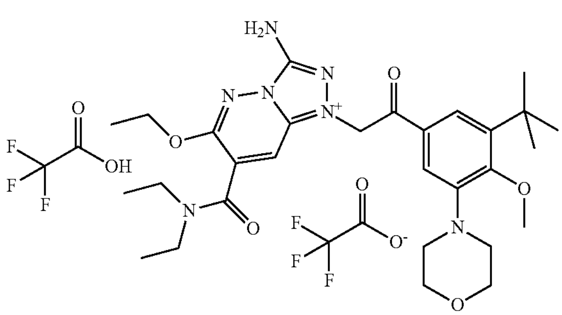 | 3-Amino-1-[2-(3-tert-butyl-4-methoxy-5-morpholin-4-ylphenyl)-2-oxoethyl]-7-diethylcarbamoyl-6-ethoxy-[1,2,4]triazolo[4,3-b]pyridazin-1-ium trifluoroacetate | 1.31 | 568.2 (met. a) |

| Example | Structure | Name | LC-MS rt [min] | [M]+ or [M + H]+ |
|---|---|---|---|---|
| Ex.: 067 | 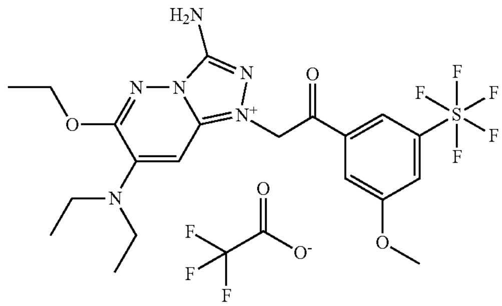 | 3-Amino-7-diethylamino-6-ethoxy-1-{2-[3-methoxy-5-(pentafluorosulfanyl)phenyl]-2-oxoethyl}-[1,2,4]triazolo[4,3-b]pyridazin-1-ium trifluoroacetate | 1.62 | 525.2 (met. a) |
| Ex.: 068 | 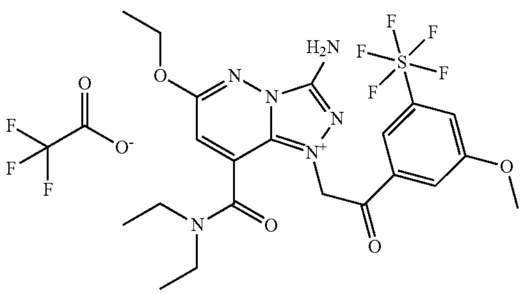 | 3-Amino-8-diethylcarbamoyl-6-ethoxy-1-{2-[3-methoxy-5-(pentafluorosulfanyl)phenyl]-2-oxoethyl}-[1,2,4]triazolo[4,3-b]pyridazin-1-ium trifluoroacetate | 1.26 | 553.2 (met. a) |
| Ex.: 069 | 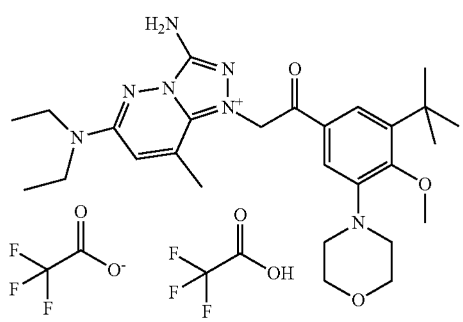 | 3-Amino-1-[2-(3-tert-butyl-4-methoxy-5-morpholin-4-ylphenyl)-2-oxoethyl]-6-diethylamino-8-methyl-[1,2,4]triazolo[4,3-b]pyridazin-1-ium trifluoroacetate | 1.05 | 510.4 (met. b) |
| Ex.: 070 | 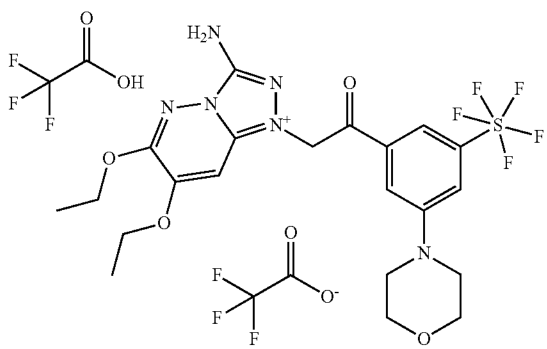 | 3-Amino-6,7-diethoxy-1-{2-[3-morpholin-4-yl-5-(pentafluorosulfanyl)phenyl]-2-oxoethyl}-[1,2,4]triazolo[4,3-b]pyridazin-1-ium trifluoroacetate | 0.96 | 553.2 (met. b) |

-continued

| Example | Structure | Name | LC-MS rt [min] | [M]+ or [M + H]+ |
|---|---|---|---|---|
| Ex.: 071 | 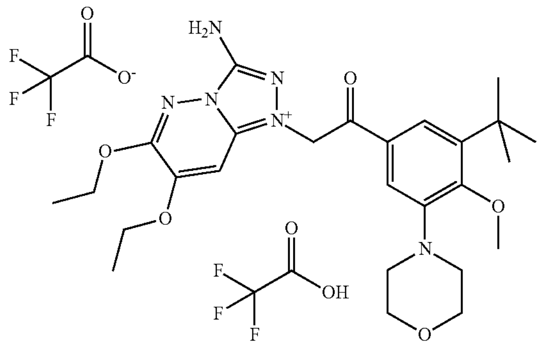 | 3-Amino-1-[2-(3-tert-butyl-4-methoxy-5-morpholin-4-ylphenyl)-2-oxoethyl]-6,7-diethoxy-[1,2,4]triazolo[4,3-b]pyridazin-1-ium trifluoroacetate | 1.00 | 513.3 (met. b) |
| Ex.: 072 | 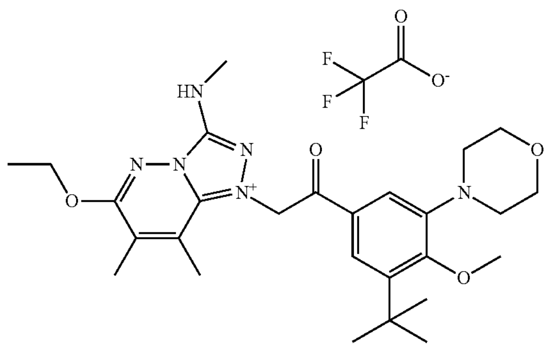 | 1-[2-(3-tert-Butyl-4-methoxy-5-morpholin-4-ylphenyl)-2-oxoethyl]-6-ethoxy-7,8-dimethyl-3-methylamino-[1,2,4]triazolo[4,3-b]pyridazin-1-ium trifluoroacetate | 1.04 | 511.4 (met. b) |
| Ex.: 073 | 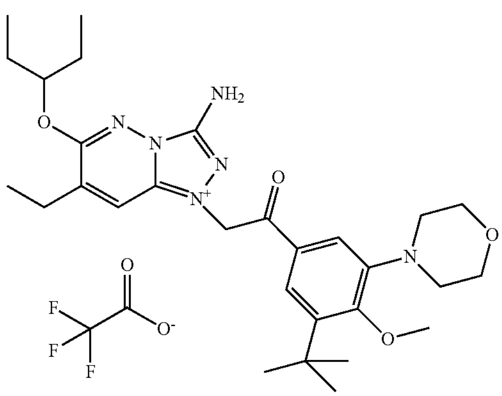 | 3-Amino-1-[2-(3-tert-butyl-4-methoxy-5-morpholin-4-ylphenyl)-2-oxoethyl]-7-ethyl-6-(1-ethylpropoxy)-[1,2,4]triazolo[4,3-b]pyridazin-1-ium trifluoroacetate | 1.09 | 539.4 (met. b) |
| Ex.: 074 | 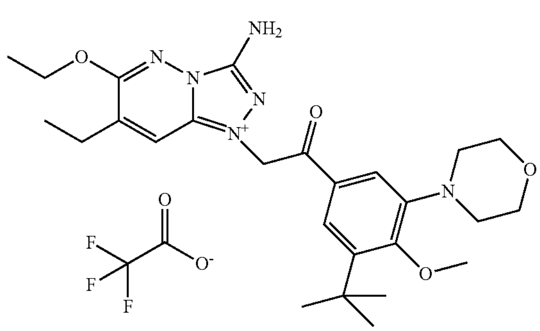 | 3-Amino-1-[2-(3-tert-butyl-4-methoxy-5-morpholin-4-ylphenyl)-2-oxoethyl]-6-ethoxy-7-ethyl-[1,2,4]triazolo[4,3-b]pyridazin-1-ium trifluoroacetate | 1.03 | 497.3 (met. b) |

-continued

| Example | Structure | Name | LC-MS rt [min] | [M]⁺ or [M + H]⁺ |
|---|---|---|---|---|
| Ex.: 075 | 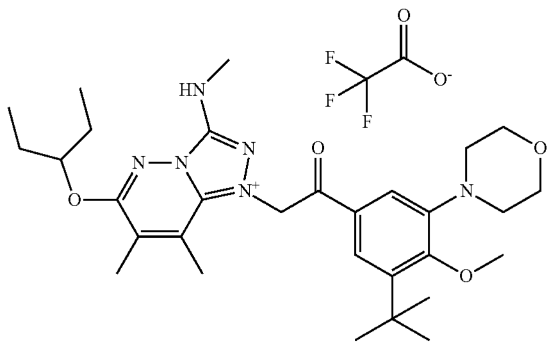 | 1-[2-(3-tert-Butyl-4-methoxy-5-morpholin-4-ylphenyl)-2-oxoethyl]-6-(1-ethylpropoxy)-7,8-dimethyl-3-methylamino-[1,2,4]triazolo[4,3-b]pyridazin-1-ium trifluoroacetate | 1.11 | 553.4 (met. b) |
| Ex.: 076 | 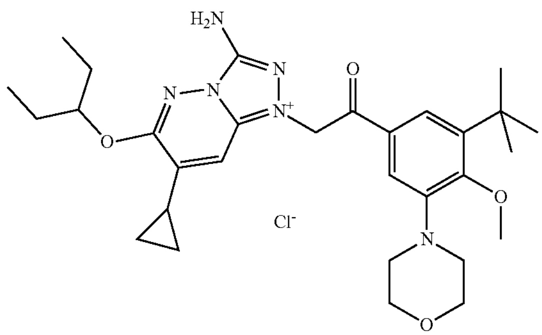 | 3-Amino-1-[2-(3-tert-butyl-4-methoxy-5-morpholin-4-ylphenyl)-2-oxoethyl]-7-cyclopropyl-6-(1-ethylpropoxy)-[1,2,4]triazolo[4,3-b]pyridazin-1-ium chloride | 1.10 | 551.4 (met. b) |
| Ex.: 077 | 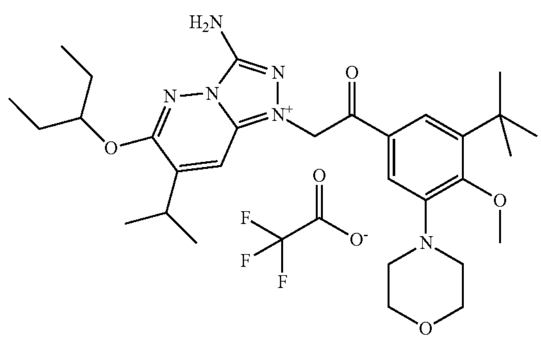 | 3-Amino-1-[2-(3-tert-butyl-4-methoxy-5-morpholin-4-ylphenyl)-2-oxoethyl]-6-(1-ethylpropoxy)-7-isopropyl-[1,2,4]triazolo[4,3-b]pyridazin-1-ium trifluoroacetate | 1.12 | 553.4 (met. b) |
| Ex.: 078 | 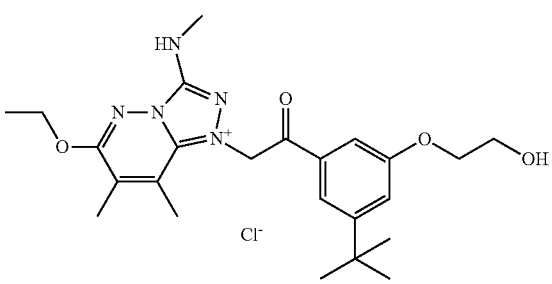 | 1-{2-[3-tert-Butyl-5-(2-hydroxyethoxy)phenyl]-2-oxoethyl}-6-ethoxy-7,8-dimethyl-3-methylamino-[1,2,4]triazolo[4,3-b]pyridazin-1-ium chloride | 0.95 | 456.3 (met. b) |
| Ex.: 079 | 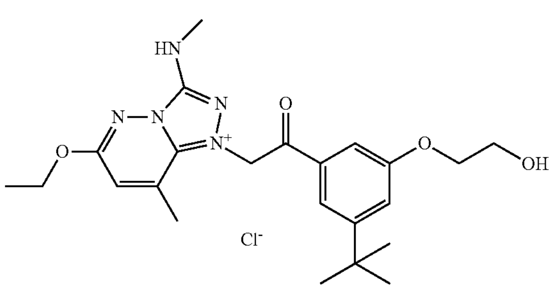 | 1-{2-[3-tert-Butyl-5-(2-hydroxyethoxy)phenyl]-2-oxoethyl}-6-ethoxy-8-methyl-3-methylamino-[1,2,4]triazolo[4,3-b]pyridazin-1-ium chloride | 0.93 | 442.3 (met. b) |

-continued

| Example | Structure | Name | LC-MS rt [min] | [M]+ or [M + H]+ |
|---|---|---|---|---|
| Ex.: 080 | 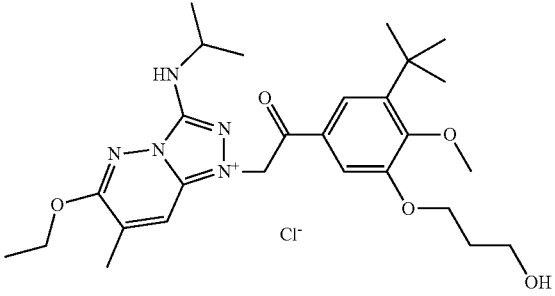 | 1-{2-[3-tert-Butyl-5-(3-hydroxypropoxy)-4-methoxyphenyl]-2-oxoethyl}-6-ethoxy-3-isopropylamino-7-methyl-[1,2,4]triazolo[4,3-b]pyridazin-1-ium chloride | 1.03 | 514.4 (met. b) |
| Ex.: 081 | 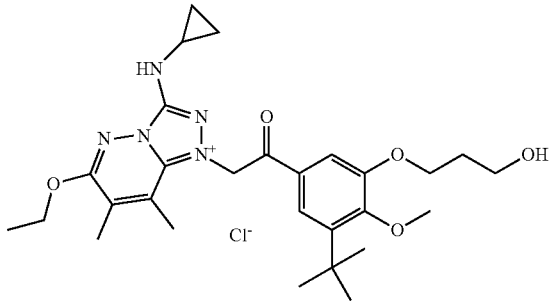 | 1-{2-[3-tert-Butyl-5-(3-hydroxypropoxy)-4-methoxyphenyl]-2-oxoethyl}-3-cyclopropylamino-6-ethoxy-7,8-dimethyl-[1,2,4]triazolo[4,3-b]pyridazin-1-ium chloride | 1.03 | 526.4 (met. b) |
| Ex.: 082 | 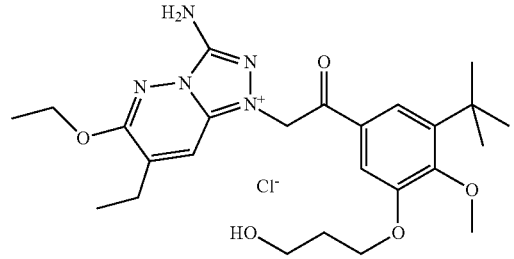 | 3-Amino-1-{2-[3-tert-butyl-5-(3-hydroxypropoxy)-4-methoxyphenyl]-2-oxoethyl}-6-ethoxy-7-ethyl-[1,2,4]triazolo[4,3-b]pyridazin-1-ium chloride | 0.97 | 486.3 (met. b) |
| Ex.: 083 | 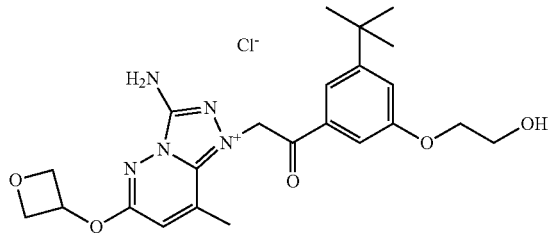 | 3-Amino-1-{2-[3-tert-butyl-5-(2-hydroxyethoxy)phenyl]-2-oxoethyl}-8-methyl-6-(oxetan-3-yloxy)-[1,2,4]triazolo[4,3-b]pyridazin-1-ium chloride | 1.08 | 456.2 (met. a) |
| Ex.: 084 | 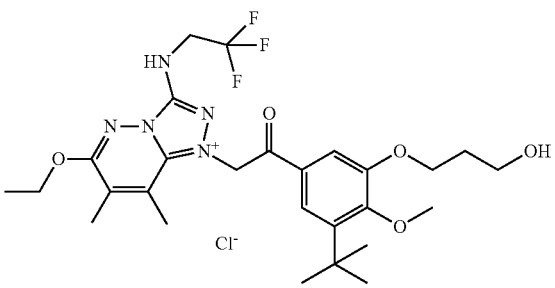 | 1-{2-[3-tert-Butyl-5-(3-hydroxypropoxy)-4-methoxyphenyl]-2-oxoethyl}-6-ethoxy-7,8-dimethyl-3-(2,2,2-trifluoroethylamino)-[1,2,4]triazolo[4,3-b]pyridazin-1-ium chloride | 1.02 | 568.3 (met. b) |

| Example | Structure | Name | LC-MS rt [min] | [M]+ or [M + H]+ |
|---|---|---|---|---|
| Ex.: 085 | 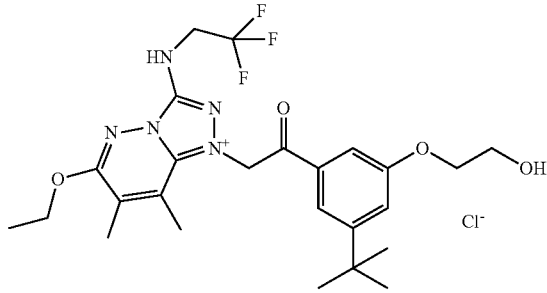 | 1-{2-[3-tert-Butyl-5-(2-hydroxyethoxy)phenyl]-2-oxo-ethyl}-6-ethoxy-7,8-dimethyl-3-(2,2,2-trifluoroethylamino)-[1,2,4]triazolo[4,3-b]pyridazin-1-ium chloride | 0.99 | 524.3 (met. b) |
| Ex.: 086 | 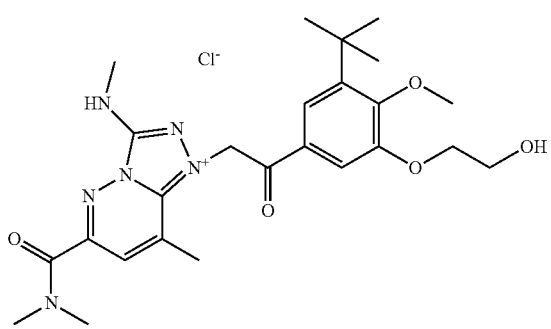 | 1-{2-[3-tert-Butyl-5-(2-hydroxyethoxy)-4-methoxyphenyl]-2-oxoethyl}-6-dimethylcarbamoyl-8-methyl-3-methylamino-[1,2,4]triazolo[4,3-b]pyridazin-1-ium chloride | 0.74 | 499.2 (met. b) |

Pharmacological Examples

PAR1 determination method: inhibition of PAR1-mediated platelet aggregation The pharmacological testing of the substances took place in platelet aggregation induced by TRAP (thrombin receptor-activating peptide) in 96-well format. For this purpose, blood was taken from healthy volunteer donors in 20 ml syringes containing 2 ml of 3.13% sodium citrate solution. After centrifugation at 150×g for 20 minutes, the platelet-rich plasma (PRP) was separated off and mixed with 1 µl of PGE1 solution (500 µg/ml in ethanol)/ml of PRP. Incubation at RT for 5 minutes was followed by centrifugation at 120×g for 15 minutes to remove the leukocytes. The leukocyte-free PRP was transferred in 5 ml portions into 15 ml PP tubes and centrifuged at 360×g for 15 minutes in order to pellet the platelets. The plasma was then decanted off and the platelet sediment from 5 ml of PRP was resuspended in 1 ml of Tyrode's (120 mM NaCl, 2.6 mM KCl, 12 mM $NaHCO_3$, 0.39 mM $NaH_2PO_4 \times H_2O$, 10 mM HEPES, 0.35% BSA, 5.5 mM glucose, pH 7.4) and adjusted with Tyrode's to a platelet count of $3 \times 10^5$/microliter (1 L). 13 ml of this cell suspension were then mixed with 866 µL of 10 mM $CaCl_2$ solution, and 120 µL thereof were pipetted into each well of a 96-well plate containing 15 µL of the substance to be tested. After incubation at RT in the dark for 30 minutes, 15 µL of a TRAP solution (70-100 µM) were added as agonist, and kinetics were recorded at 650 nm in a SpectraMax 340 at 37° C. for 20 minutes while shaking The areas under the curves of negative control (Tyrode's/DMSO) and positive control (15 µl of agonist/DMSO) were calculated and the difference was fixed as the 100% value. The substances to be tested were pipetted as serial dilutions in duplicate determination, the AUC was likewise determined for each substance concentration, and the % inhibition of the AUC compared with the control was calculated. On the basis of the % inhibition, the $IC_{50}$ was calculated by nonlinear regression analysis according to the 4-parameter equation. Table 1 shows the results.

TABLE 1

| Compound from example | Inhibition of platelet aggregation $IC_{50}$ [micro M] | Compound from example | Inhibition of platelet aggregation $IC_{50}$ [micro M] |
|---|---|---|---|
| 1 | <0.014 | 3 | 1.08 |
| 4 | 0.126 | 8 | 4.4 |
| 26 | 0.005 | 32 | 0.006 |
| 38 | 0.24 | 39 | 0.037 |

PAR1 Binding Test

The synthesized substances were examined in a PAR1 binding test. This tested whether the substances can inhibit the binding of a radioactively labeled PAR1 agonist known from the literature at the PAR1 receptor (Ho-Sam Ahn, Mol Pharm, 51:350-356, 1997).

The human PAR1 receptor was expressed transiently in High Five insect cells. From these cells, after 48 hours, a membrane preparation was produced by standard methods, aliquoted into 10 mM Tris-HCl; 0.3 mM EDTA; 1 mM EGTA; 250 mM sucrose pH 7.5, and stored at −80° C.

The substances were preincubated with the membrane at RT for 15 minutes, then the radioligand (ALA-(para-F-Phe)-Arg-ChA-homoArg-(3,4-$^3$H-Tyr)-$NH_2$; approx. 40 Ci/mMol) was added. The end concentration of the radioligand in the test buffer (50 mM Tris-HCl; 10 mM $MgCl_2$; 1 mM EGTA; 0.1% BSA; 2% DMSO) was 20 nM, that of the membrane 1 mg/ml. After an incubation time of 60 minutes, 25 µL of the mixture were transferred to a 96-well Multi-ScreenHTS FB microtiter filtration plate (from Millipore), which had been pretreated beforehand with a 0.75% aqueous polyethyleneimine solution for 5 hours at RT. Thereafter, with vacuum extraction, each well was washed four times with 300 µL of buffer (50 mM Tris-HCl; 10 mM $MgCl_2$; 1 mM EGTA). The plate was then dried overnight, 100 µl of scintillator per well were added, and the plate was analyzed after 6 hours in a Wallac MicroBeta (from PerkinElmer) liquid scintillation counter. The nonspecific binding was determined in the presence of 100 μM SCH79797 (PAR-1 antagonist; from Tocris, Cat. No. 1592) and subtracted from all measurements. The 100% value used was a control without inhibitor. The % inhibition values of a substance dilution series were used to calculate the $IC_{50}$ with the aid of nonlinear regression analysis according to the 4-parameter equation.

Table 2 shows the results.

TABLE 2

| Compound from example | Inhibition of binding $IC_{50}$ [micro M] | Compound from example | Inhibition of binding $IC_{50}$ [micro M] |
|---|---|---|---|
| 27 | 0.152 | 54 | 0.085 |
| 29 | 0.136 | 60 | 2.1 |
| 35 | 0.132 | 72 | 1.7 |
| 40 | 0.601 | 76 | 1.4 |
| 46 | 0.114 | 82 | 8.4 |
| 47 | 10 | | |

What is claimed is:
1. A compound of formula I

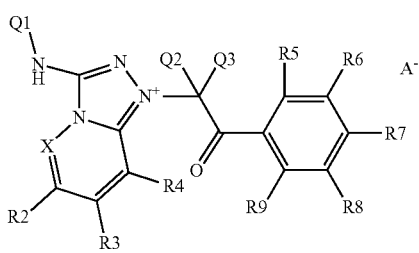

(I)

or a stereoisomeric or tautomeric form thereof, or a physiologically compatible salt of any of them, where
X is N,
A⁻ is an anion of an organic or inorganic acid,
Q1 is a hydrogen atom, —($C_1$-$C_6$)-alkyl, —($C_3$-$C_6$)-cycloalkyl, —($C_0$-$C_4$)-alkylene-C(O)—O—R11, —($C_0$-$C_4$)-alkylene-C(O)—N(R11)-R12, —($C_0$-$C_4$)-alkylene-C(O)—R11, —OH, —O—($C_1$-$C_8$)-alkyl or —O—($C_3$-$C_6$)-cycloalkyl, where alkyl and cycloalkyl are each unsubstituted or mono-, di- or trisubstituted independently by —($C_1$-$C_4$)-alkyl, —($C_3$-$C_8$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine,
Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine,
R1, R2, R3 and R4 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_8$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-N(R11)-C(O)—O—R12, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —NO₂, —SO₂CH₃, —SO₂CF₃, —SF₅, —Si[—($C_1$-$C_4$)-alkyl]₃, —($C_1$-$C_6$)-alkylene-O—($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —O—($C_1$-$C_4$)-alkylene-($C_3$-$C_6$)-cycloalkyl, —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl or —O—($C_1$-$C_6$)-alkylene-O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine, or
R1 and R2, R2 and R3 or R3 and R4, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine,
R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —SO₂OH₃ or —SO₂CF₃, where some or all of the hydrogen atoms in alkyl, alkylene or cycloalkyl may be replaced by fluorine, or
R11 and R12 in the "N(R11)-R12" and "N(R11)-C(O)—R12" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine,
R5, R6, R7, R8 and R9 are the same or different and are each independently a hydrogen atom, —($C_1$-$C_6$)-alkyl, —($C_3$-$C_6$)-cycloalkyl, OH, —CN, —NO₂, —O—($C_1$-$C_8$)-alkyl, —O—($C_3$-$C_6$)-cycloalkyl, —($C_0$-$C_4$)-alkylene-(CO)—N(R21)-R22, —SO₂CH₃, —SO₂CF₃, —($C_0$-$C_4$)-alkylene-C(O)—O—R21, halogen, —SF₅, —($C_0$-$C_4$)-alkylene-C(O)—R21, —($C_0$-$C_4$)-alkylene-N(R21)—R22, —($C_0$-$C_4$)-alkylene-N(R21)-C(O)—R22, —($C_1$-$C_6$)-alkylene-O—($C_1$-$C_6$)-alkyl, —Si[—($C_1$-$C_4$)-alkyl]₃, —($C_0$-$C_6$)-alkylene-O—($C_1$-$C_6$)-alkylene-O—($C_1$-$C_6$)-alkyl, —($C_4$-$C_{15}$)-Het, —($C_0$-$C_6$)- alkylene-O—($C_0$-$C_6$)-alkylene-($C_3$-$C_6$)-cycloalkyl or —($C_0$-$C_6$)-alkylene-O—($C_0$-$C_6$)-alkylene-($C_6$-$C_{14}$)-aryl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where some or all of the hydrogen atoms in alkyl, alkylene or cycloalkyl may be replaced by fluorine, or R5 and R6, R6 and R7, R7 and R8 or R8 and R9, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

2. A compound as claimed in claim 1, wherein

X is N, $A^-$ is an anion of an organic or inorganic acid,

Q1 is a hydrogen atom, —($C_1$-$C_6$)-alkyl, —($C_3$-$C_6$)-cycloalkyl, —($C_0$-$C_4$)-alkylene-C(O)—O—R11, —($C_0$-$C_4$)-alkylene-C(O)—N(R11)-R12, —($C_0$-$C_4$)-alkylene-C(O)—R11, —OH, —O—($C_1$-$C_6$)-alkyl or —O—($C_3$-$C_6$)-cycloalkyl, where alkyl and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine, R1, R2, R3 and R4 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_6$)—cycloalkyl, —($C_0$-$C_4$)-alkylene-C(O)—N(R11)-R12, —($C_0$-$C_4$)-alkylene-N(R11)-C(O)-β—R12, —($C_0$-$C_4$)-alkylene-C(O)—O—R11, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —$SO_2CF_3$, —$SF_5$, —Si[—($C_1$-$C_4$)-alkyl]$_3$, —($C_1$-$C_6$)-alkylene-O—($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —O—($C_1$-$C_4$)-alkylene-($C_3$-$C_6$)-cycloalkyl, —($C_4$-$C_{15}$)-Het where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, where some or all of the hydrogen atoms in alkyl, alkylene or cycloalkyl may be replaced by fluorine, with the proviso that at least one R1, R2, R3 or R4 is not a hydrogen atom or R1 and R2, R2 and R3 or R3 and R4, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R4, R5, R6, R7, R8 and R9 are the same or different and are each independently a hydrogen atom, —($C_1$-$C_6$)-alkyl, —($C_3$-$C_6$)-cycloalkyl, OH,
—CN, —$NO_2$, —O—($C_1$-$C_8$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$,
—($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —($C_0$-$C_6$)-alkylene-O—($C_1$-$C_6$)-alkylene-O—($C_1$-$C_6$)-alkyl, —Si[($C_1$-$C_4$)-alkyl]$_3$, —($C_0$-$C_6$)-alkylene-O—($C_1$-$C_4$)-alkylene-($C_3$-$C_6$)-cycloalkyl, —($C_0$-$C_6$)-alkylene-O—($C_0$-$C_6$)-alkylene-($C_6$-$C_{14}$)-aryl or —($C_4$-$C_{15}$)-Het,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or
—O—($C_3$-$C_6$)-cycloalkyl,
—($C_4$-$C_{15}$)-Het where Het is unsubstituted or mono-, di-, tri-, tetra- or pentasubstituted independently by halogen, —($C_1$-$C_4$)-alkyl,
—($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine,
with the proviso that at least one R5, R6, R7, R8 or R9 is not a hydrogen atom, or
R5 and R6, R6 and R7, R7 and R8 or R8 and R9, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or
—O—($C_3$-$C_6$)-cycloalkyl, where some or all of the hydrogen atoms in the 5- to 8-membered ring formed, and in alkyl or cycloalkyl, may be replaced by fluorine,
R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or
R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

3. A compound as claimed in claim 1, wherein
X is N,
$A^-$ is an anion of an organic or inorganic acid,
Q1 is a hydrogen atom, —($C_1$-$C_6$)-alkyl, —($C_3$-$C_6$)-cycloalkyl, —($C_0$-$C_4$)-alkylene-C(O)—O—R11, —($C_0$-$C_4$)-alkylene-C(O)—N(R11)-R12, —($C_0$-$C_4$)-alkylene-C(O)—R11, —OH, —O—($C_1$-$C_6$)-alkyl or —O—($C_3$-$C_6$)-cycloalkyl, where alkyl and cycloalkyl are each unsubstituted or mono-, di- or trisubstituted independently by —($C_1$-$C_4$)-alkyl,
—($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine,
Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine,
R1, R2, R3 and R4 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-N(R11)-C(O)—O—R12, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —Si[—($C_1$-$C_4$)-alkyl]$_3$, —($C_1$-$C_6$)-alkylene-O—($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl, —O—($C_1$-$C_4$)-alkylene-($C_3$-$C_6$)-cycloalkyl, —($C_4$-$C_{15}$)-Het or —O—($C_1$-$C_6$)-alkylene-O—($C_1$-$C_6$)-alkylene-O—($C_1$-$C_6$)-alkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
where some or all of the hydrogen atoms in alkyl, alkylene or cycloalkyl may be replaced by fluorine,
with the proviso that at least one R1, R2, R3 or R4 is not a hydrogen atom or
R1 and R2, R2 and R3 or R3 and R4, together with the ring atoms to which they are each bonded, form a ring selected from the group of 2,3,5,6,7,8-hexahydro-1,2,3a,4,5,8-hexaaza-cyclopenta[b]naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaazacyclopenta[a]-naphthalene; 2,3-dihydro-5,7-dioxa-1,2,3a,4-tetraazas-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine and 2,3,6a,9a-tetrahydro-[1,3]dioxolo[4,5-d][1,2,4]triazolo[4,3-b]pyridazine, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine,
R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl,
—($C_0$-$C_4$)-alkylene-($C_4$-$C_{15}$)-Het, —$SO_2CH_3$ or —$SO_2CF_3$,
where some or all of the hydrogen atoms in alkyl, alkylene or cycloalkyl may be replaced by fluorine, or
R11 and R12 in the "N(R11)-R12" and "N(R11)-C(O)—R12" fragments represent a 5- to 8-membered ring, selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in the 5- to 8-membered ring formed, and in alkyl or cycloalkyl, may be replaced by fluorine, R4, R5, R6, R7, R8 and R9 are the same or different and are each independently a hydrogen atom, —$(C_1$-$C_6)$-alkyl, —$(C_3$-$C_6)$-cycloalkyl, OH, —CN, —$NO_2$, —O—$(C_1$-$C_8)$-alkyl, —O—$(C_3$-$C_6)$-cycloalkyl, —$SO_2CH_3$, —$SO_2CF_3$, —$(C_0$-$C_4)$-alkylene-(CO)—N(R21)-R22, —$(C_0$-$C_4)$-alkylene-C(O)—O—R21, halogen, —$SF_5$, —$(C_0$-$C_4)$-alkylene-C(O)—R21, —$(C_0$-$C_4)$-alkylene-N(R21)-R22, —$(C_0$-$C_4)$-alkylene-N(R21)-0(O)—R22, —$(C_1$-$C_6)$-alkylene-O—$(C_1$-$C_6)$-alkyl, —$(C_0$-$C_6)$-alkylene-O—$(C_1$-$C_6)$-alkylene-O—$(C_1$-$C_6)$-alkyl, —Si[—$(C_1$-$C_4)$-alkyl]$_3$, —$(C_0$-$C_6)$-alkylene-O—$(C_1$-$C_4)$-alkylene-$(C_3$-$C_6)$-cycloalkyl, —$(C_0$-$C_6)$-alkylene-O—$(C_0$-$C_6)$-alkylene-$(C_6$-$C_{14})$-aryl or —$(C_4$-$C_{15})$-Het, where alkyl, alkylene and cycloalkyl are each unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl, —$(C_6$-$C_{14})$-aryl where aryl is unsubstituted or mono-, di-, tri-, tetra- or pentasubstituted independently by halogen, —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, —$(C_4$-$C_{15})$-Het where Het is unsubstituted or mono-, di-, tri-, tetra- or pentasubstituted independently by halogen, —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, or —O—$(C_3$-$C_6)$-cycloalkyl, where some or all of the hydrogen atoms in alkyl, alkylene or cycloalkyl may be replaced by fluorine, with the proviso that at least one R5, R6, R7, R8 or R9 is not a hydrogen atom, or R5 and R6, R6 and R7, R7 and R8 or R8 and R9, together with the ring atoms to which they are each bonded, form a 5- to 8-membered ring selected from the group of 2,3-dihydrobenzo[1,4]dioxin; 3,4-dihydro-2H-benzo[1,4]oxazine; 1,2,3,4-tetrahydroquinoxaline; benzo[1,3]dioxole; 3,4-dihydro-2H-benzo[1,4]thiazine and 2,3,4,5-tetrahydro-1H-benzo[b][1,4]diazepine, where the ring is unsubstituted or mono- or disubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in the 5- to 8-membered ring formed, and in alkyl or cycloalkyl, may be replaced by fluorine, R21 and R22 are each independently a hydrogen atom, —$(C_1$-$C_6)$-alkyl, —$(C_3$-$C_6)$-cycloalkyl, —$(C_0$-$C_4)$-alkylene-$(C_6$-$C_{14})$-aryl, —$(C_0$-$C_4)$-alkylene-$(C_4$-$C_{15})$-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in the 5- to 8-membered ring formed, and in alkyl or cycloalkyl, may be replaced by fluorine.

4. A compound as claimed in claim 1, wherein

X is N,

A$^-$ is an anion of an organic or inorganic acid,

Q1 is a hydrogen atom, —$(C_1$-$C_6)$-alkyl, —$(C_3$-$C_6)$-cycloalkyl, —$(C_0$-$C_4)$-alkylene-C(O)—O—R11, —$(C_0$-$C_4)$-alkylene-C(O)—N(R11)-R12, —$(C_0$-$C_4)$-alkylene-C(O)—R11, —OH, —O—$(C_1$-$C_6)$-alkyl or —O—$(C_3$-$C_6)$-cycloalkyl, where alkyl and cycloalkyl are each unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in alkyl or cycloalkyl may be replaced by fluorine, Q2 and Q3 are the same or different and are each independently a hydrogen atom, —$(C_1$-$C_6)$-alkyl or —$(C_3$-$C_6)$-cycloalkyl, where some or all of the hydrogen atoms in alkyl or cycloalkyl may be replaced by fluorine, R1, R2, R3 and R4 are the same or different and are each independently a hydrogen atom, —$(C_1$-$C_4)$-alkyl, —O—$(C_1$-$C_8)$-alkyl, —O—$(C_3$-$C_6)$-cycloalkyl, —$(C_0$-$C_4)$-alkylene-C(O)—N(R11)-R12, —$(C_0$-$C_4)$-alkylene-C(O)—O—R11, —$CF_3$, —$(C_0$-$C_4)$-alkylene-N(R11)—C(O)—O—R12, —$(C_0$-$C_4)$-alkylene-N(R11)-R12, chlorine, —O—$(C_1$-$C_6)$-alkylene-O—$(C_1$-$C_6)$-alkyl, —O—$(C_0$-$C_4)$-alkylene-$(C_6$-$C_{14})$-aryl or —$(C_4$-$C_{15})$-Het where Het is selected from the group of acridinyl, azepinyl, azetidinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrol, thienopyridin, thienothiazolyl, thienothiophenyl, thiomorpholinyl, triazinyl, 1,2,3-triazolyl, 1,2,4-triazolyl, 1,2,5-triazolyl, 1,3,4-triazolyland xanthenyl, where alkylene is unsubstituted or monosubstituted by —$(C_1$-$C_4)$-alkyl or —$(C_3$-$C_6)$-cycloalkyl, or some or all of the hydrogen atoms in alkylene are replaced by fluorine, R11 and R12 are each independently a hydrogen atom or —$(C_1$-$C_6)$-alkyl, R5, R6, R7, R8 and R9 are the same or different and are each independently a hydrogen atom, —(C$_1$-C$_6$)-alkyl, OH, —O—(C$_1$-C$_8$)-alkyl, chlorine, bromine, —SF$_5$, —(C$_0$-C$_4$)-alkylene-N(R21)-R22, —(C$_4$-C$_{15}$)-Het, —(C$_0$-C$_4$)-alkylene-N(R21)-C(O)—R22, —CF$_3$—(C$_0$-C$_6$)-alkylene-O—(C$_1$-C$_6$)-alkyl, —(C$_0$-C$_6$)-alkylene-O—(C$_1$-C$_4$)-alkylene-(C$_3$-C$_6$)-cycloalkyl or —(C$_0$-C$_6$)-alkylene-O—(C$_0$-C$_6$)-alkylene-(C$_6$-C$_{14}$)-aryl, where alkylene is unsubstituted or monosubstituted by —O—(C$_1$-C$_6$)-alkyl, with the proviso that at least one R5, R6, R7, R8 or R9 is not a hydrogen atom, R5 and R6, R6 and R7, R7 and R8 or R8 and R9, together with the ring atoms to which they are each bonded, form a morpholine ring, where the ring is unsubstituted or monosubstituted by —(C$_1$-C$_4$)-alkyl, R21 and R22 are each independently a hydrogen atom or —(C$_1$-C$_6$)-alkyl.

5. A compound as claimed in claim 1, wherein the compound is a physiologically compatible salt of:

1-{2-[3-acetylamino-5-(pentafluorosulfanyl)phenyl]-2-oxoethyl}-3-amino-6-ethoxy-[1,2,4]triazolo[4,3-b]pyridazin-1-ium, 3-amino-6-chloro-1-[2-(3,5-di-tert-butyl-4-hydroxyphenyl)-2-oxoethyl]-[1,2,4]triazolo[4,3-b]pyridazin-1-ium, 3-amino-1-[2-(3-tert-butyl-4-methoxy-5-morpholin-4-ylphenyl)-2-oxoethyl]-6-ethoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-isopropoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-methoxy-[1,2,4]triazolo[4,3-b]pyridazin-1-ium, 3-amino-6-ethoxy-1-[2-(4-methoxy-3-morpholin-4-yl-5-trifluoromethylphenyl)-2-oxoethyl]-[1,2,4]triazolo[4,3-b]pyridazin-1-ium, 1-{2-[3-acetylamino-5-(pentafluorosulfanyl)phenyl]-2-oxoethyl}-3-amino-6-ethoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclopentyloxy-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclobutoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-phenoxy-[1,2,4]triazolo[4,3-b]pyridazin-1-ium, 3-amino-6-benzyloxy-1-[2-(3-tert-butyl-4-methoxy-5-morpholin-4-ylphenyl)-2-oxoethyl]-[1,2,4]triazolo[4,3-b]pyridazin-1-ium, 3-amino-1-[2-(3-tert-butyl-4-methoxy-5-morpholin-4-ylphenyl)-2-oxoethyl]-6-(1-ethylpropoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclohexyloxy-[1,2,4]triazolo[4,3-b]pyridazin-1-ium, 3-amino-1-[2-(3-tert-butyl-4-methoxy-5-morpholin-4-yl-phenyl)-2-oxoethyl]-6-(2,2,2-trifluoroethoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-cyclopropyl-methoxy-[1,2,4]triazolo[4,3-b]pyridazin-1-ium, 3-amino-1-[2-(3-tert-butyl-4-methoxy-5-morpholin-4-ylphenyl)-2-oxoethyl]-6-ethoxy-[1,2,4]triazolo[4,3-b]pyridazin-1-ium, 3-amino-6-(1-ethylpropoxy)-1-{2-[3-methylamino-5-(pentafluorosulfanyl)phenyl]-2-oxoethyl}-[1,2,4]triazolo[4,3-b]pyridazin-1-ium, 3-amino-6-(1-ethylpropoxy)-1-{2-[3-methoxy-5-(pentafluorosulfanyl)phenyl]-2-oxoethyl}-[1,2,4]triazolo[4,3-b]pyridazin-1-ium, 3-amino-1-[2-(3-tert-butyl-5-ethoxymethylphenyl)-2-oxoethyl]-6-(1-ethylpropoxy)-[1,2,4]triazolo[4,3-b]pyridazin-1-ium, 3-amino-1-[2-(3-tert-butyl-5-cyclopropylmethoxymethylphenyl)-2-oxoethyl]-6-(1-ethylpropoxy)-[1,2,4]triazolo[4,3-b]pyridazin-1-ium, 3-amino-1-[2-(3-tert-butyl-4,5-diethoxyphenyl)-2-oxoethyl]-6-(1-ethylpropoxy)-[1,2,4]triazolo[4,3-b]pyridazin-1-ium, 3-amino-1-[2-(3-tert-butyl-4,5-biscyclopropylmethoxyphenyl)-2-oxoethyl]-6-(1-ethylpropoxy)-[1,2,4]triazolo[4,3-b]pyridazin-1-ium, 3-amino-1-[2-(3-tert-butyl-5-propoxymethylphenyl)-2-oxoethyl]-6-(1-ethylpropoxy)-[1,2,4]triazolo[4,3-b]pyridazin-1-ium, 3-amino-1-[2-(3-tert-butyl-5-ethoxyphenyl)-2-oxoethyl]-6-(1-ethylpropoxy)-[1,2,4]triazolo-[4,3-b]pyridazin-1-ium, 3-amino-6-(1-ethylpropoxy)-1-[2-(3-methoxy-5-trifluoromethyl phenyl)-2-oxoethyl]-[1,2,4]triazolo[4,3-b]pyridazin-1-ium, 3-amino-1-[2-(3-tert-butyl-5-methoxyphenyl)-2-oxoethyl]-6-(1-ethylpropoxy)-[1,2,4]triazolo[4,3-b]pyridazin-1-ium, 3-amino-1-[2-(3-tert-butyl-5-cyclopropylmethoxyphenyl)-2-oxoethyl]-6-(1-ethylpropoxy)-[1,2,4]triazolo[4,3-b]pyridazin-1-ium, 3-amino-1-[2-(3-tert-butyl-5-cyclobutylmethoxyphenyl)-2-oxoethyl]-6-(1-ethyl-propoxy)-[1,2,4]triazolo[4,3-b]pyridazin-1-ium, 3-amino-1-[2-(3-benzyloxymethyl-5-tert-butylphenyl)-2-oxoethyl]-6-(1-ethylpropoxy)-[1,2,4]triazolo[4,3-b]pyridazin-1-ium, 3-amino-1-[2-(3-cyclohexylmethoxy-4,5-dimethoxyphenyl)-2-oxoethyl]-6-(1-ethylpropoxy)-[1,2,4]triazolo[4,3-b]pyridazin-1-ium, 3-amino-6-butoxy-1-[2-(3-tert-butyl-5-methoxymethylphenyl)-2-oxoethyl]-[1,2,4]triazolo[4,3-b]pyridazin-1-ium, 3-amino-1-[2-(3-chloro-5-methoxyphenyl)-2-oxoethyl]-6-(1-ethylpropoxy)-[1,2,4]triazolo-[4,3-b]pyridazin-1-ium, 3-amino-1-[2-(8-tert-butyl-4-methyl-3,4-dihydro-2H-benzo[1,4]oxazin-6-yl)-2-oxoethyl]-6-(1-ethylpropoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-diethylamino-[1,2,4]triazolo[4,3-b]pyridazin-1-ium, 3-amino-1-[2-(3-tert-butyl-4-methoxy-5-morpholin-4-ylphenyl)-2-oxoethyl]-6-piperidin-1-yl-[1,2,4]triazolo[4,3-b]pyridazin-1-ium, 3-amino-1-[2-(3-cyclohexylmethoxy-5-ethoxyphenyl)-2-oxo-ethyl]-6-(1-ethylpropoxy)-[1,2,4]triazolo[4,3-b]pyridazin-1-ium, 3-amino-1-[2-(3-bromo-5-methoxyphenyl)-2-oxoethyl]-6-(1-ethylpropoxy)-[1,2,4]triazolo-[4,3-b]pyridazin-1-ium, 3-amino-6-(1-ethylpropoxy)-1-[2-(3-isopropyl-5-methoxy-phenyl)-2-oxoethyl]-[1,2,4]triazolo[4,3-b]pyridazin-1-ium, 3-amino-1-[2-(3-cyclohexylmethoxy-5-methoxyphenyl)-2-oxoethyl]-6-(1-ethylpropoxy)-[1,2,4]triazolo[4,3-b]pyridazin-1-ium, 3-amino-1-{2-[3-(3,3-dimethylbutoxy)-5-ethoxyphenyl]-2-oxoethyl}-6-(1-ethylpropoxy)-[1,2,4]triazolo[4,3-b]pyridazin-1-ium, 3-amino-6-diethylamino-1-{2-[3-methoxy-5-(pentafluorosulfanyl)phenyl]-2-oxoethyl}-[1,2,4]triazolo[4,3-b]pyridazin-1-ium, 3-amino-1-[2-(3-tert-butyl-4-methoxy-5-morpholin-4-ylphenyl)-2-oxoethyl]-6-morpholin-4-yl-[1,2,4]triazolo[4,3-b]pyridazin-1-ium, 3-amino-1-[2-(5-bromo-2,3-dimethoxyphenyl)-2-oxoethyl]-6-(1-ethylpropoxy)-[1,2,4]triazolo[4,3-b]pyridazin-1-ium, 3-amino-1-[2-(3-chloro-4,5-dimethoxy-phenyl)-2-oxoethyl]-6-(1-ethylpropoxy)-[1,2,4]-triazolo[4,3-b]pyridazin-1-ium, 3-amino-1-{2-[3-tert-butyl-5-(2-methoxyethoxy)phenyl]-2-oxoethyl}-6-(1-ethylpropoxy)-[1,2,4]triazolo[4,3-b]pyridazin-1-ium, 3-amino-1-[2-(3-tert-butyl-5-methoxyphenyl)-2-oxoethyl]-6-(2-methoxyethoxy)-[1,2,4]triazolo[4,3-b]pyridazin-1-ium, 3-amino-1-[2-(3-tert-butyl-5-methoxymethylphenyl)-2-oxoethyl]-6-(2-methoxy-ethoxy)-[1,2,4]triazolo[4,3-b]pyridazin-1-ium, 3-amino-1-[2-(3-tert-butyl-4-methoxy-5-morpholin-4-ylphenyl)-2-oxoethyl]-6-chloro-[1,2,4]triazolo[4,3-b]pyridazin-1-ium, 3-amino-6-(1-ethylpropoxy)-1-{2-[3-morpholin-4-yl-5-(pentafluorosulfanyl)phenyl]-2-oxoethyl}-[1,2,4]triazolo[4,3-b]pyridazin-1-ium, 3-amino-6-ethyl-1-{2-[3-methoxy-5-(pentafluorosulfanyl)phenyl]-2-oxoethyl}-[1,2,4]triazolo[4,3-b]pyridazin-1-ium, 3-amino-1-[2-(3-tert-butyl-4-methoxy-5-morpholin-4-ylphenyl)-2-oxoethyl]-6-ethyl-[1,2,4]triazolo[4,3-b]pyridazin-1-ium, 3-amino-6-chloro-7-diethylcarbamoyl-1-{2-[3-methoxy-5-(pentafluorosulfanyl)phenyl]-2-oxoethyl}-[1,2,4]triazolo[4,3-b]pyridazin-1-ium or 3-amino-1-[2-(3-tert-butyl-4-methoxy-5-morpholin-4-ylphenyl)-2-oxoethyl]-6-chloro-7-diethylcarbamoyl-[1,2,4]triazolo[4,3-b]pyridazin-1-ium.

6. A pharmaceutical composition comprising at least one compound as claimed in claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,198,272 B2 | Page 1 of 3 |
| APPLICATION NO. | : 12/851219 | |
| DATED | : June 12, 2012 | |
| INVENTOR(S) | : Uwe Heinelt et al. | |

It is certified that error appears in the above-identified patent and that said Letters Patent is hereby corrected as shown below:

On page 2, in column 1, under "Other Publications", line 3, delete "Letter," and insert -- Letters, --, therefor.

In column 4, line 2, delete "alkylene-β-" and insert -- alkylene-O- --, therefor.

In column 4, line 53, delete "alkylene-β-" and insert -- alkylene-O- --, therefor.

In column 6, line 56, delete "(C(O)" and insert -- (CO) --, therefor.

In column 8, line 5, delete "alkylene-β-" and insert -- alkylene-O- --, therefor.

In column 20, line 51, delete "tribomide," and insert -- tribromide, --, therefor.

In column 21, line 10, delete "  " and insert --  --, therefor.

In column 21, line 27-34, delete " 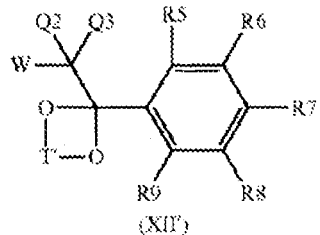 " and insert -- 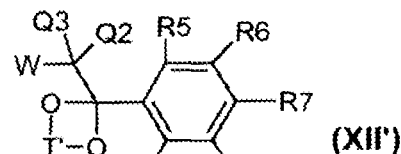 --, therefor.

Signed and Sealed this
Twenty-third Day of October, 2012

David J. Kappos
*Director of the United States Patent and Trademark Office*

CERTIFICATE OF CORRECTION (continued)
U.S. Pat. No. 8,198,272 B2

In column 21, line 51-58, delete " 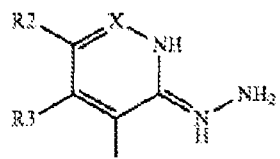 " and insert -- 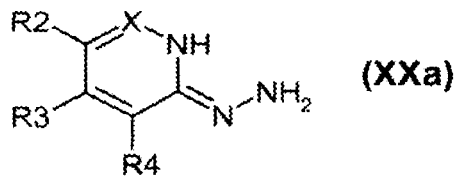 --, therefor.

In column 27, line 51, delete "J'rshere" and insert -- J'shere --, therefor.

In column 28, line 17, after "H₂O" insert -- +0.05% --.

In column 28, line 27, after "H₂O" insert -- +0.05% --.

In column 29, line 31, delete "Hiinig's" and insert -- Hünig's --, therefor.

In column 48, line 11, delete "trifluormethyl" and insert -- trifluoromethyl --, therefor.

In column 49, line 17, delete "(Chlorpyridazin" and insert -- (Chloropyridazin --, therefor.

In column 69, line 44-45, delete "trifluormethylphenyl" and insert -- trifluoromethylphenyl --, therefor.

In column 73, line 34, delete "trifluormethylphenyl" and insert -- trifluoromethylphenyl --, therefor.

In column 106, line 46-55, delete " 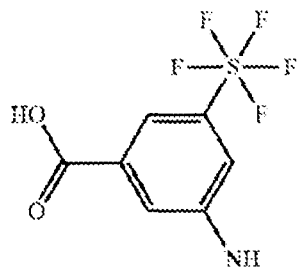 " and insert -- 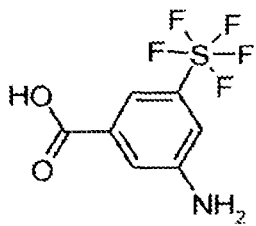 --, therefor.

CERTIFICATE OF CORRECTION (continued)
U.S. Pat. No. 8,198,272 B2

In column 115-116, in Table, Example 004, line 5, delete "[1,2,4)" and insert -- [1,2,4] --, therefor.

In column 135-136, in Table, Example 051, line 2, delete "mopholin" and insert -- morpholin --, therefor.

In column 151, line 51, delete "(1 L)." and insert -- µL). --, therefor.

In column 151, line 58, delete "shaking" and insert -- shaking. --, therefor.

In column 153, line 44, in claim 1, delete "($C_1$-$C_8$)-" and insert -- ($C_1$-$C_6$)- --, therefor.

In column 153, line 48, in claim 1, delete "($C_3$-$C_8$)-" and insert -- ($C_3$-$C_6$)- --, therefor.

In column 153, line 60, in claim 1, delete "($C_3$-$C_8$)-" and insert -- ($C_3$-$C_6$)- --, therefor.

In column 154, line 41, in claim 1, delete "—$SO_2OH_3$" and insert -- —$SO_2CH_3$ --, therefor.

In column 156, line 3, in claim 2, delete "-β—" and insert -- -O— --, therefor.

In column 157, line 11, in claim 2, delete "—Si[$C_1$-$C_4$)-" and insert -- —Si[-($C_1$-$C_4$)- --, therefor.

In column 159, line 16, in claim 3, delete "-0(O)—" and insert -- -C(O)— --, therefor.

In column 160, line 62, in claim 4, delete "1,3,4-triazolyland" and insert -- 1,3,4-triazolyl and --, therefor.

In column 162, line 27, in claim 5, delete "triazolo-" and insert -- triazolo --, therefor.

In column 162, line 29-30, in claim 5, delete "trifluoromethyl phenyl)" and insert -- trifluoromethylphenyl) --, therefor.